United States Patent [19]

Nakamura et al.

[11] Patent Number: 5,354,501
[45] Date of Patent: Oct. 11, 1994

[54] MESOMORPHIC COMPOUND, LIQUID CRYSTAL COMPOSITION, LIQUID CRYSTAL DEVICE, DISPLAY APPARATUS AND DISPLAY METHOD

[75] Inventors: Shinichi Nakamura, Hadano; Takao Takiguchi, Tokyo; Kenji Shinjo, Atsugi; Takashi Iwaki, Machida; Takeshi Togano, Yokohama; Yoko Yamada, Isehara, all of Japan

[73] Assignee: Canon Kabushiki Kaisha, Tokyo, Japan

[21] Appl. No.: 15,826

[22] Filed: Feb. 10, 1993

[30] Foreign Application Priority Data

Feb. 12, 1992 [JP] Japan ................. 4-057259
Feb. 10, 1993 [JP] Japan ................. 4-044356

[51] Int. Cl.$^5$ ............... C09K 19/32; C09K 19/52; C07C 13/45; G02F 1/13
[52] U.S. Cl. ............... 252/299.62; 252/299.01; 252/299.61; 252/299.63; 252/299.64; 252/299.65; 252/299.66; 252/299.67; 585/26; 359/103
[58] Field of Search ........... 252/299.01, 299.62, 252/299.63, 299.64, 299.65, 299.66, 299.67; 585/25, 26; 544/242, 298, 335; 546/26; 548/122, 123, 124, 125, 217, 218, 219, 220; 549/1, 29, 64

[56] References Cited

U.S. PATENT DOCUMENTS

| | | | |
|---|---|---|---|
| 3,956,363 | 5/1976 | Shen et al. | 260/479 R |
| 4,367,924 | 1/1983 | Clark et al. | 359/103 |
| 5,075,030 | 12/1991 | Togano et al. | 252/299.61 |
| 5,091,109 | 2/1992 | Takiguchi et al. | 252/299.61 |
| 5,116,530 | 5/1992 | Togano et al. | 252/299.61 |
| 5,118,441 | 6/1992 | Mori et al. | 252/299.61 |
| 5,188,762 | 2/1993 | Iwaki et al. | 252/299.62 |
| 5,190,690 | 3/1993 | Takiguchi et al. | 252/299.61 |
| 5,194,177 | 3/1993 | Nohira et al. | 252/299.61 |
| 5,213,709 | 5/1993 | Takiguchi et al. | 252/299.61 |

FOREIGN PATENT DOCUMENTS

| | | |
|---|---|---|
| 0325035 | 7/1989 | European Pat. Off. . |
| 0136020 | 6/1991 | Japan . |
| 0107216 | 8/1991 | Japan . |

OTHER PUBLICATIONS

CA70(1):3587c, 1968.
CA113(3):2428b, 1989.
CA90(21):167803j, 1978.
Schadt, et al., Applied Physics Letters, vol. 18, No. 1 (1971) 127-8.
Derwent Abstract AN 81-59674 (JP-A-56 079,647).
Patent Abstract Japan, vol. 16, No. 114 (1992).
Juby et al., J. Medical Chemistry, vol. 15, No. 2 (1972) 1297-1306.
Pinder, Journal Chem. Soc., No. 1 (1970) 114-5.
Minssen-Guette, et al., Bulletin Soc.Chem.Fr., No. 5 (1968) 2111-7.
Chemical Abstract, vol. 106, No. 5 (1987) 32847.

*Primary Examiner*—Shean Wu
*Attorney, Agent, or Firm*—Fitzpatrick, Cella, Harper & Scinto

[57] ABSTRACT

A mesomorphic compound of the formula (I) according to Claim 1 and an optically active compound of the formula (II) according to Claim 2 are suitable as a component for a liquid crystal composition providing improved response characteristics and having an improved helical pitch at a cholesteric phase or a chiral smectic C phase. The above liquid crystal composition is useful as an element of a liquid crystal device providing a good display characteristics including a gradation display.

72 Claims, 5 Drawing Sheets

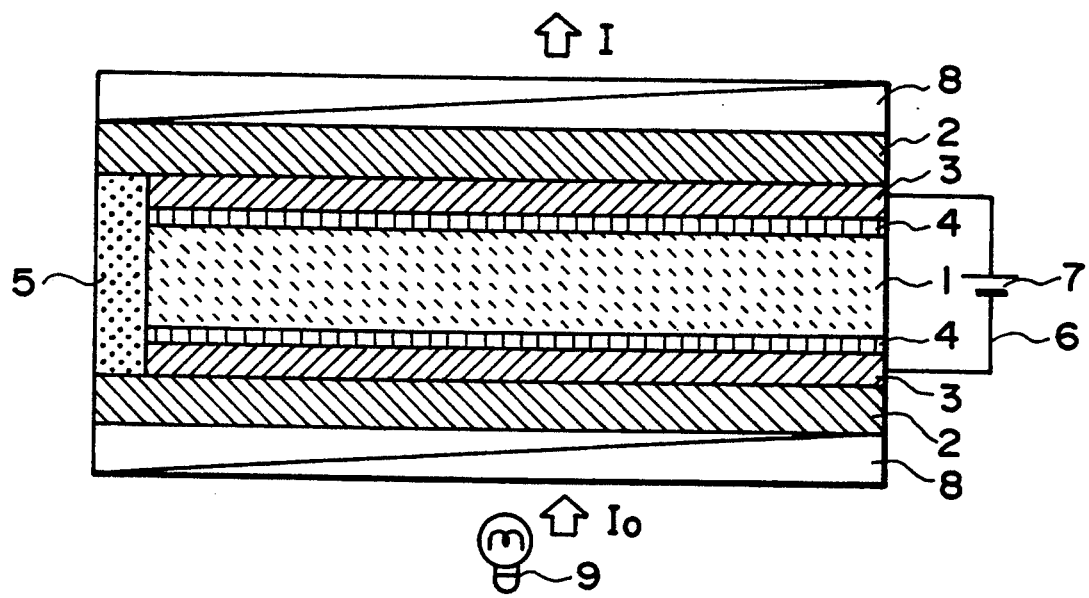
F I G. 1

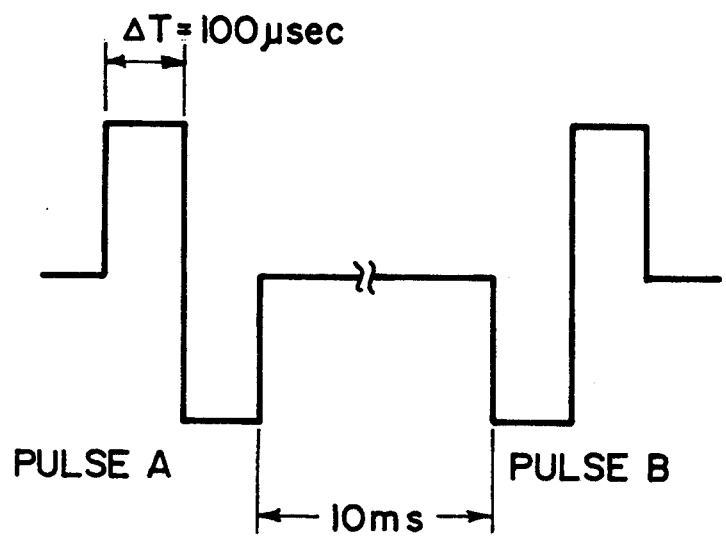
F I G. 6
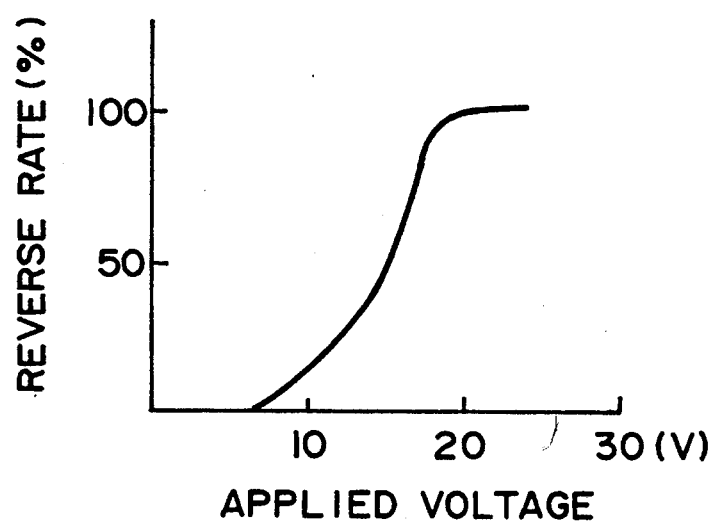
F I G. 7

MESOMORPHIC COMPOUND, LIQUID CRYSTAL COMPOSITION, LIQUID CRYSTAL DEVICE, DISPLAY APPARATUS AND DISPLAY METHOD

FIELD OF THE INVENTION AND RELATED ART

The present invention relates to a mesomorphic compound, a liquid crystal composition, a liquid crystal device, a display apparatus and a display method, and more particularly to a mesomorphic compound, a liquid crystal composition containing the mesomorphic compound with improved responsiveness to an electric field, a liquid crystal device using the liquid crystal composition for use in a display device, a liquid crystal-optical shutter, etc., a display apparatus using the device, and a display method of using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of $\mu$sec, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 107216/1981; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the abovementioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, etc. Among a response time $\gamma$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, if it is assumed that the operation temperature of an actual display device is 5°–40 ° C., the response speed changes by a factor of about 20, so that it actually exceeds the range controllable by driving voltage and frequency.

Thus, as described hereinabove, commercialization of a ferroelectric liquid crystal device requires a liquid crystal composition assuming a chiral smectic phase which has a high-speed responsiveness and a small temperature-dependence of response speed.

The ferroelectric liquid crystal composition is required to show a uniform alignment characteristic over a large picture area.

In the present invention, it is preferable that an aligning method capable of aligning molecular layers, constituted by liquid crystal molecules forming a smectic liquid crystal, in the uniaxial direction along a normal of the molecular layers over a large picture area and also capable of aligning the liquid crystal molecules by a rubbing treatment providing a simple production process is applied.

In order to readily align the liquid crystal molecules, a ferroelectric liquid crystal composition is generally required to show a cholesteric phase and have a larger helical pitch at the cholesteric phase. Generally speaking, the ferroelectric liquid crystal comprises at least one chiral (or optically active) compound. When a content of the chiral compound is increased in order to obtain an intended property, a helical pitch at a cholesteric phase (hereinafter, simply referred to as "Ch pitch" or "cholesteric pitch") becomes small, thus falling to provide a uniform alignment characteristic in many cases. Hitherto, in order to improve an alignment characteristic, a chiral compound having a helical structure opposite to that of the chiral compound contained in the ferroelectric liquid crystal composition has been added to the composition to control the Ch pitch (i.e., to provide a longer Ch pitch).

However, in this instance, it has been difficult to provide a ferroelectric liquid crystal composition having intended properties. Accordingly, it is required to provide a chiral compound capable of controlling a Ch pitch without impairing properties of a resultant ferroelectric liquid crystal composition.

In recent years, there has been discovered a novel property of a chiral compound by controlling a helical pitch at a chiral smectic C phase (hereinafter, simply referred to as "SmC* pitch" or "chiral smectic C pitch") in addition to a Ch pitch with respect to a liquid crystal composition containing the chiral compound, and it is expected that the novel property of the chiral compound is widely applied. For example, Japanese Laid-Open Patent Application No. 136020/1991 by L. A. BERESNEV et al. has disclosed a liquid crystal device including a liquid crystal composition with a considerably short SmC* pitch and the liquid crystal device can effect a gradation display.

Heretofore, ferroelectric liquid crystal devices have merely provided two display states of a light (or white) state and a dark (or black) state, thus failing to effect a gradation display. It is expected that the ferroelectric liquid crystal device is widely applied to a display device if the gradation display is realized.

A compound with a short helical pitch constituting a liquid crystal device for use in a display device or apparatus capable of effecting the above-mentioned gradation display generally makes features of not only the short helical pitch but also a considerably large spontaneous polarization. The compound provides a ferroelectric liquid crystal composition having a spontaneous polarization of 10 $nC/cm^2$ or above, thus enabling a gradation display.

However, when such a ferroelectric liquid crystal composition is used as a (liquid crystal) display device, the display device encounters a serious problem of occurrence of a switching failure (i.e., a display state is not effectively reversed or inversed) in addition to the above-mentioned defect of an increase in viscosity (e.g., 13-th Liquid Crystal Form (Preprint, p. 142)). Further, when a spontaneous polarization is large, a premittivity is increased to invite heat generation and deformation or transformation of an applied waveform.

Since the conventional compound having a short helical pitch constituting a conventional liquid crystal device has a large spontaneous polarization, it is difficult to control a value of a helical pitch (or spontaneous polarization) while fixing a value of a spontaneous polarization (or helical pitch).

Thus, the ferroelectric liquid crystal device (or composition) requires a compound capable of effectively controlling a helical pitch alone without impairing other liquid crystal characteristics.

SUMMARY OF THE INVENTION

An object of the present invention is to provide a mesomorphic compound effective for providing high response speed and a decreased temperature-dependence of response speed, a liquid crystal composition, particularly a chiral smectic liquid crystal composition containing the mesomorphic compound for providing a practical ferroelectric liquid crystal device as described above, a liquid crystal device including the liquid crystal composition, a display apparatus including the device, and a display method of using the composition or device.

Another object of the present invention is to provide an optically active compound effective for controlling a cholesteric pitch or a chiral smectic C pitch of a liquid crystal composition, a liquid crystal composition containing the optically active compound, particularly a chiral smectic liquid crystal composition having ferroelectricity, a liquid crystal device including the liquid crystal composition, a display apparatus including the liquid crystal device, and a display method of using the liquid crystal composition or the liquid crystal device.

According to the present invention, there is provided a mesomorphic compound represented by the following formula (I):

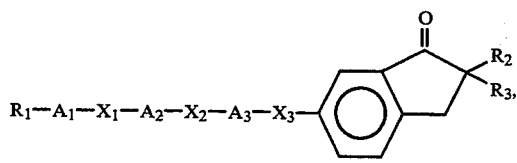 (I)

wherein

R$_1$, R$_2$ and R$_3$ independently denote hydrogen, halogen, —CN,

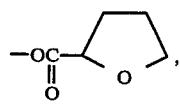

or a linear or branched alkyl group having 1–18 carbon atoms capable of including one or non-neighboring two or more —CH$_2$— groups which can be replaced with —O—, —S—,

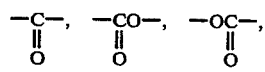

—CH=CH— or —C≡C—, the linear or branched alkyl group being capable of including hydrogen which can be replaced with fluorine;

X$_1$, X$_2$ and X$_3$ independently denote a single bond,

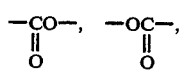

—CH$_2$O— or —OCH$_2$—;

A$_2$ and A$_3$ independently denote a single bond,

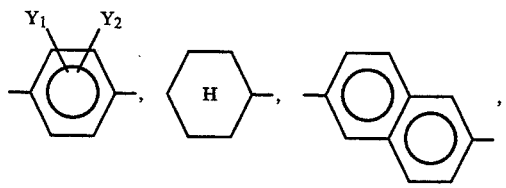

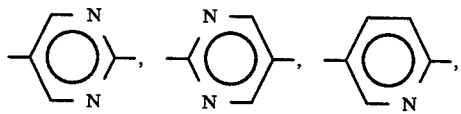

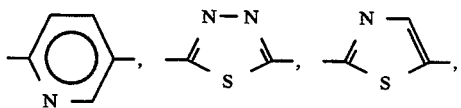

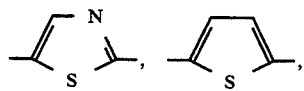

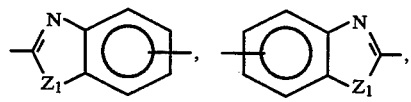

wherein Y$_1$ and Y$_2$ independently denote H, F, Cl, Br, CH$_3$, CF$_3$ or CN, and. Z$_1$ denotes O or S; and A$_1$ denotes

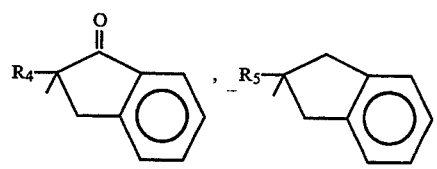

or A$_2$, wherein R$_4$ and R$_5$ independently denote hydrogen, or a linear or branched alkyl group having 1–18 carbon atoms.

The present invention provides an optically active compound represented by the following formula (II):

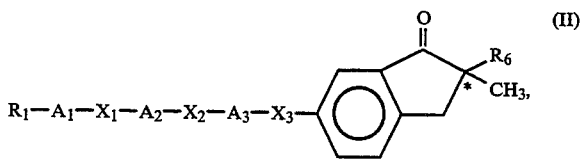 (II)

wherein

R$_1$ denotes hydrogen, halogen, —CN,

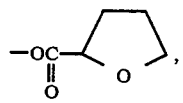

or a linear or branched alkyl group having 1–18 carbon atoms capable of including one or non-neighboring two or more —CH$_2$— groups which can be replaced with —O—, —S—,

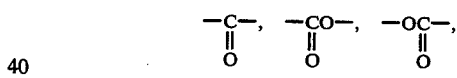

—CH=CH— or —C≡C—, the linear or branched alkyl group being capable of including hydrogen which can be replaced with fluorine;

R$_6$ denotes a linear alkyl group having 2–16 carbon atoms;

X$_1$, X$_2$ and X$_3$ independently denote a single bond,

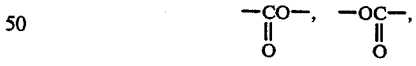

—CH$_2$O— or —OCH$_2$—;

A$_2$ and A$_3$ independently denote a single bond,

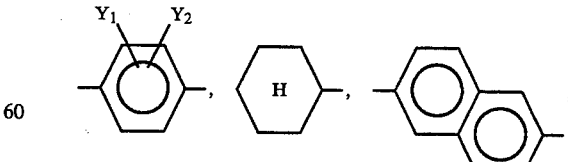

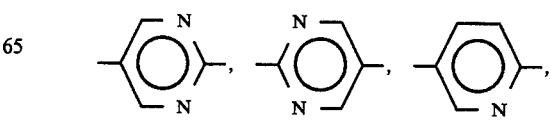

-continued

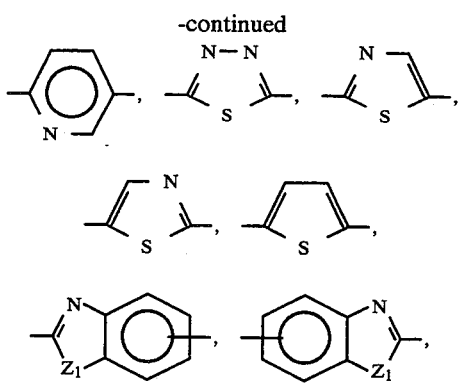

wherein $Y_1$ and $Y_2$ independently denote H, F, Cl, Br, CH$_3$, CF$_3$ or CN, and $Z_1$ denotes O or S;

$A_1$ denotes

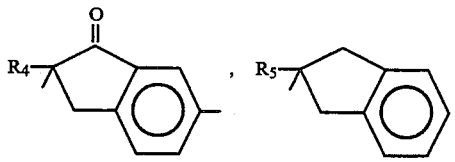

or $A_2$, wherein $R_4$ and $R_5$ independently denote hydrogen, or a linear or branched alkyl group having 1–18 carbon atoms; and

* denotes a location of an optically active center.

According to the present invention, there is further provided a liquid crystal composition containing at least one species of the above-mentioned mesomorphic compounds or optically active compounds.

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method of using the liquid crystal composition or the liquid crystal device described above and switching the alignment direction of liquid crystal molecules by applying voltages to the liquid crystal composition to effect display.

We have found that a mesomorphic compound represented by the formula (I) or (II) having an indanone skeleton is suitable as a component of a ferroelectric chiral smectic liquid crystal composition and a liquid crystal device including the liquid crystal composition which provide good display characteristics based on improvements in various characteristics such as an alignment characteristic, high speed responsiveness, and a temperature-dependence of response speed.

We have also found that the mesomorphic compound of the formula (I) or (II) is effective in readily controlling a Ch pitch and/or an SmC* pitch. More specifically, we have found that it is possible to control a helical pitch of a liquid crystal composition without substantially changing liquid crystal characteristics such as phase transition series and a spontaneous polarization by mixing the mesomorphic compound of the present invention in a small amount since the mesomorphic compound has a very short Ch pitch. Based on the above property of the mesomorphic compound of the present invention, there is provided a liquid crystal composition with a good alignment characteristic and an elongated Ch pitch without impairing liquid crystal characteristics by mixing a small amount of the mesomorphic compound of the present invention with a liquid crystal composition containing at least one another chiral compound. As to the SmC* pitch, we have found that it is possible to readily control the SmC* by mixing the mesomorphic or optically active compound of the present invention in a small amount similarly as in the case of the Ch pitch. By using the optically active compound of the present invention, the SmC* pitch is readily shortened while fixing a value of a spontaneous polarization (Ps). A liquid crystal device including the resultant liquid crystal composition containing the optically active compound can provide a gradation display. Particularly, it is possible to effect a gradation display by a liquid crystal device including a liquid crystal composition having a small Ps (e.g., Ps < 10 nC/cm$^2$) and a shortened SmC* pitch due to the addition of the optically active compound according to the present invention.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 1 is a schematic sectional view of a liquid crystal display device using a liquid crystal composition assuming a chiral smectic phase;

FIG. 6 shows an applied waveform used in Example 44 according to the present invention.

FIG. 7 is a graph showing a relationship between an applied voltage and rate of a reverse domain.

DETAILED DESCRIPTION OF THE INVENTION

Figure 2:
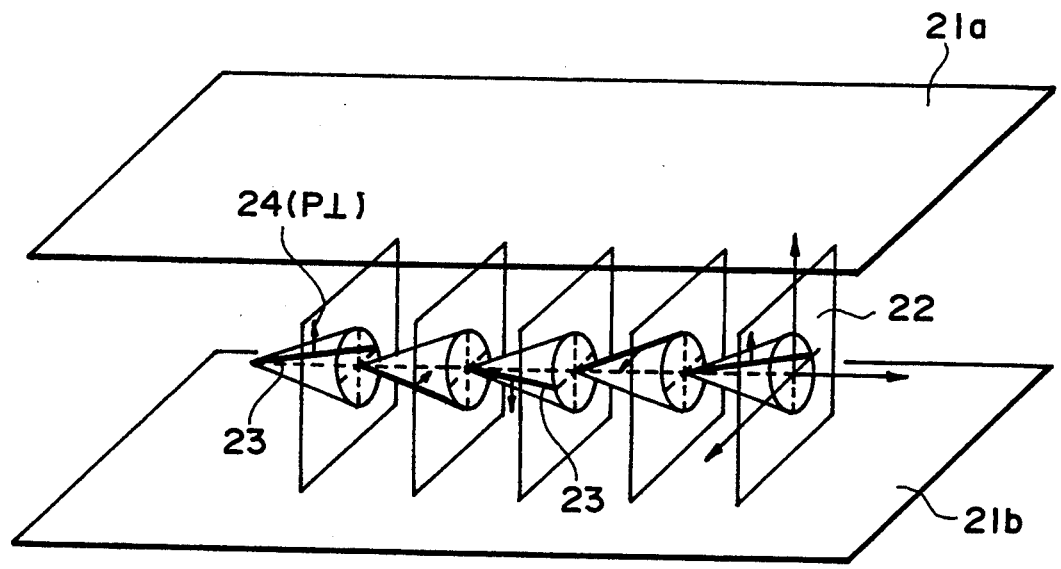
FIGS. 2 and 3 are schematic perspective views of a device cell embodiment for illustrating the operation principle of a liquid crystal device utilizing ferroelectricity of a liquid crystal composition.

The mesomorphic compound of the formula (I) may include an optically active compound and an optically inactive compound.

In a mesogen group of a mesomorphic compound, an increase in the number of linkage groups having a polarity is liable to increase a viscosity of the resultant liquid crystal composition. In order to obtain a liquid crystal composition having a low viscosity, it is desirable that the number of linkage groups of a mesomorphic compound is minimized.

Preferred examples of the mesomorphic compound of the formula (I) may include those of the following formulas (Ia) to (Id) having one or two linkage groups:

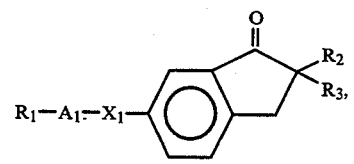 (Ia)

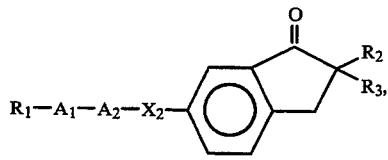 (Ib)

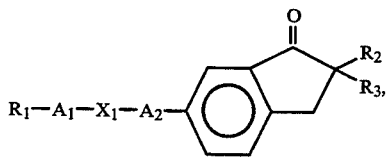 (Ic)

and

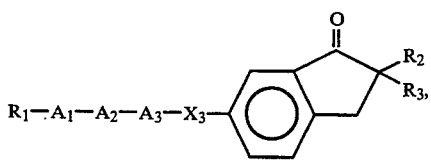 (Id)

wherein

R₁, R₂ and R₃ independently denote hydrogen, halogen, —CN,

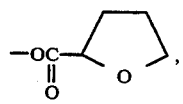

or a linear or branched alkyl group having 1-18 carbon atoms capable of including one or non-neighboring two or more —CH₂— groups which can be replaced with —O—, —S—,

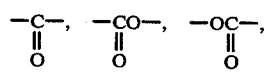

—CH=CH— or —C≡C—, the linear or branched alkyl group being capable of including hydrogen which can be replaced with fluorine:

X₁, X₂ and X₃ independently denote a single bond, $-\overset{\text{O}}{\underset{\|}{C}}-$, $-\overset{\text{O}}{\underset{\|}{C}}O-$, $-O\overset{\text{O}}{\underset{\|}{C}}-$, —CH₂O— or —OCH₂—;

A₂ and A₃ independently denote a single bond,

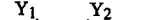

wherein Y₁ and Y₂ independently denote H, F, Cl, Br, CH₃, CF₃ or CN, and Z₁ denotes O or S; and
A₁ denotes

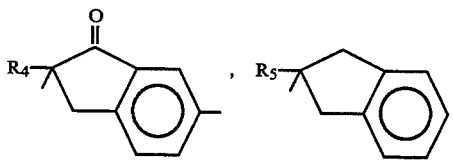

or A₂, wherein R₄ and R₅ independently denote hydrogen, or a linear or branched alkyl group having 1-18 carbon atoms.

In view of various properties such as viscosity, a temperature range of a mesomorphic phase, compatibility, and an alignment characteristic, further preferred examples of the mesomorphic compound of the formula (I) may include those of the following formulas (Iaa) to (Idc):

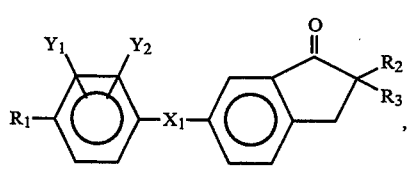 (Iaa)

-continued
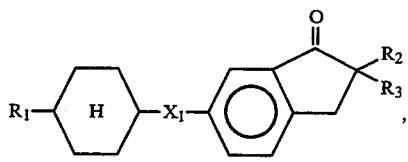
(Iab)
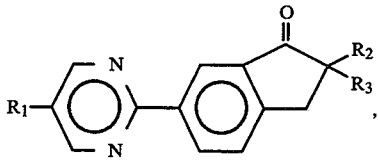
(Iac)
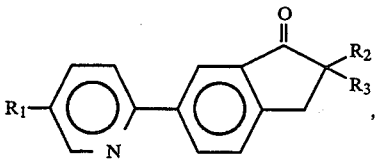
(Iad)
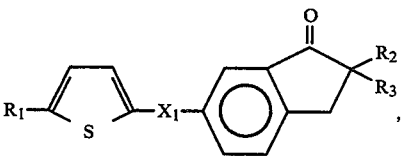
(Iae)
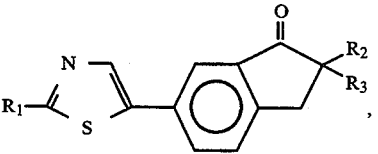
(Iaf)
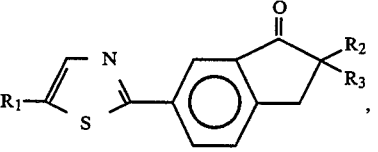
(Iag)
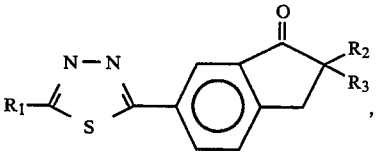
(Iah)
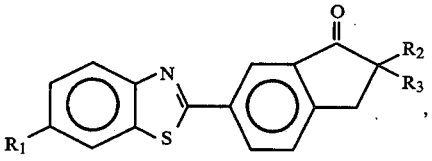
(Iai)
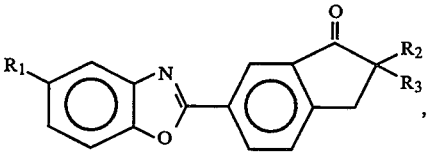
(Iaj)
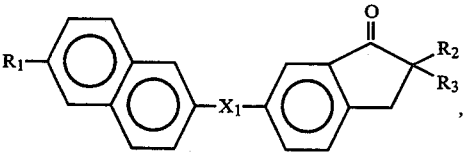
(Iak)

-continued
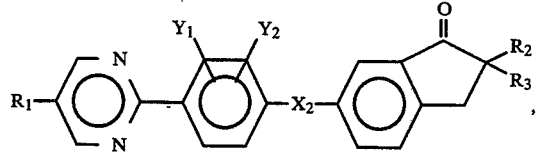 (Iba)
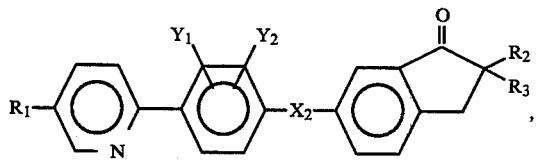 (Ibb)
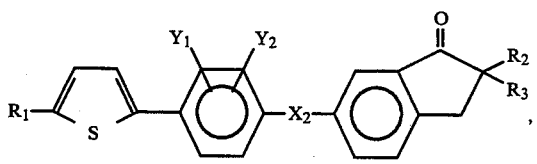 (Ibc)
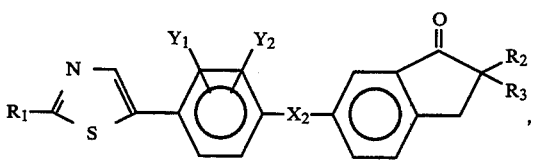 (Ibd)
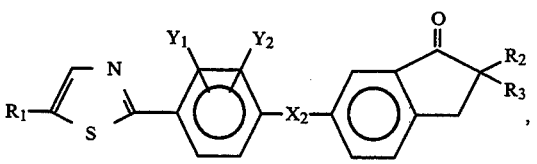 (Ibe)
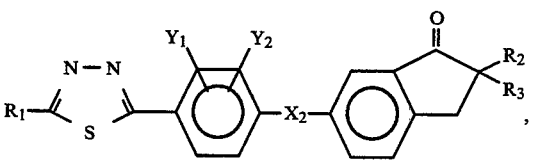 (Ibf)
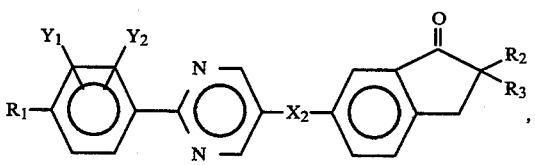 (Ibg)
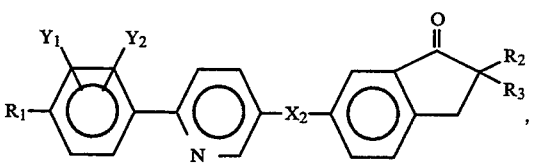 (Ibh)
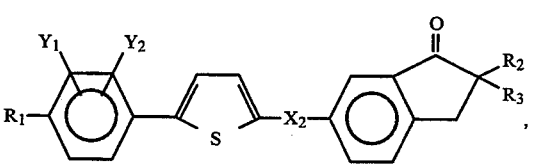 (Ibi)
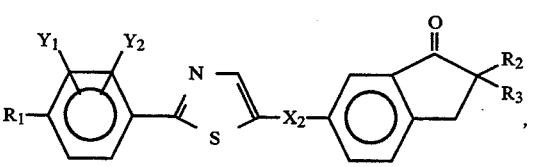 (Ibj)

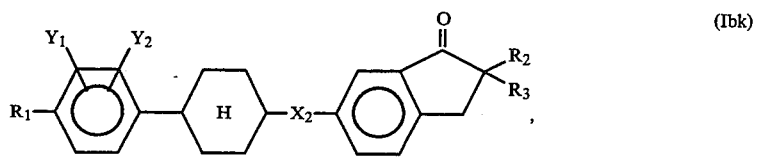
(Ibk)
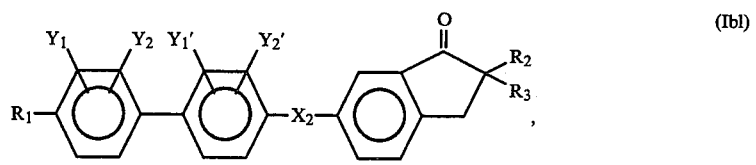
(Ibl)
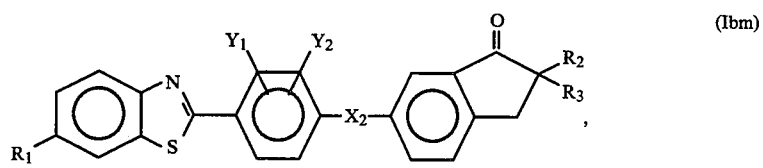
(Ibm)
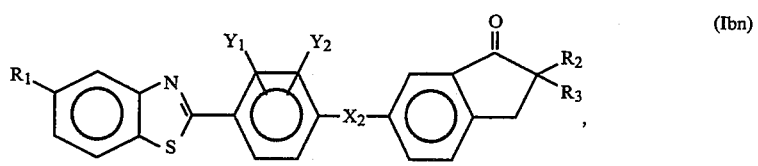
(Ibn)
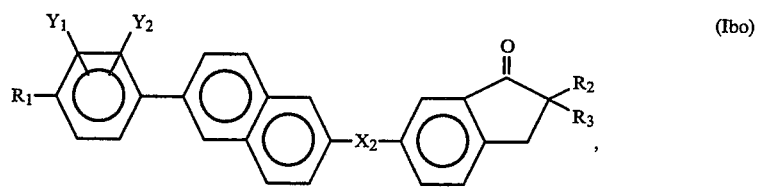
(Ibo)
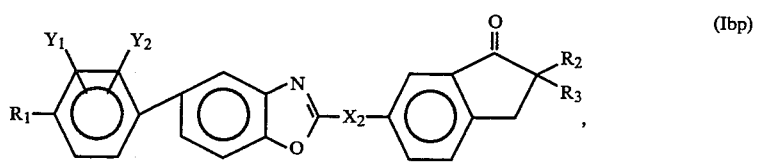
(Ibp)
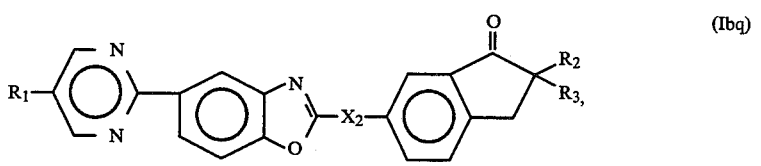
(Ibq)
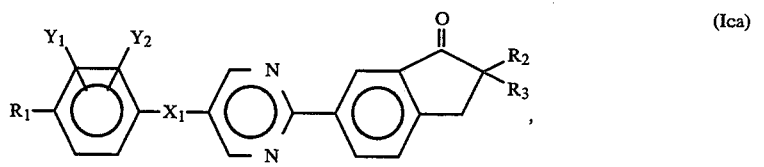
(Ica)
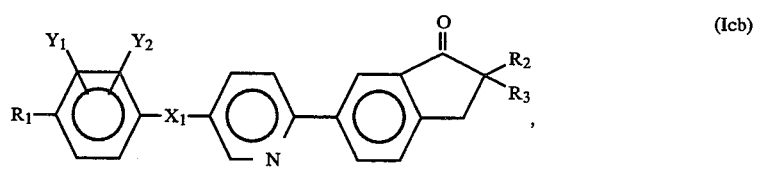
(Icb)

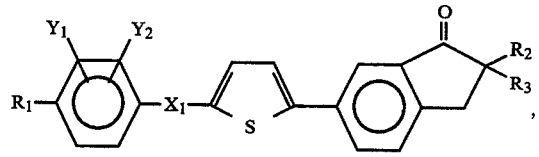 (Icc)
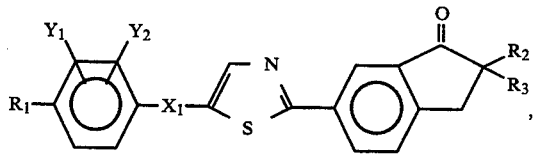 (Icd)
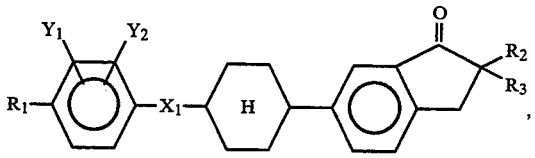 (Ice)
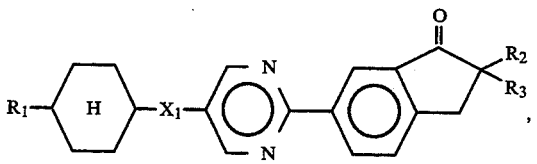 (Icf)
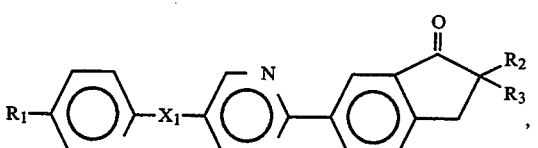 (Icg)
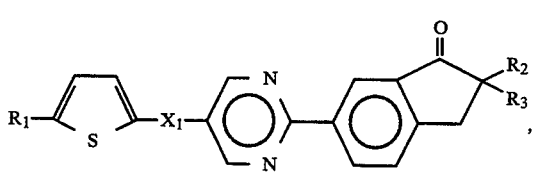 (Ich)
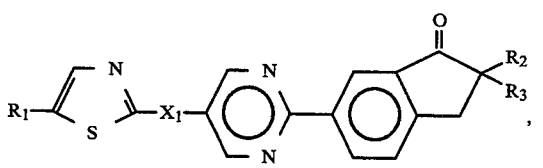 (Ici)
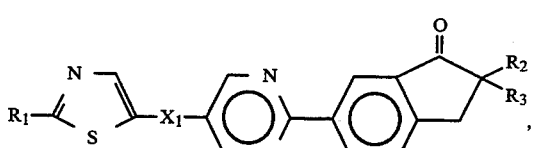 (Icj)
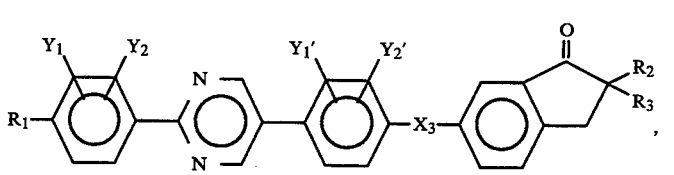 (Ida)
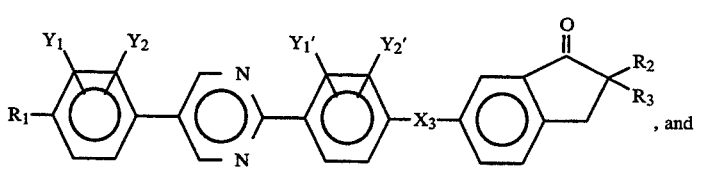 (Idb)
, and

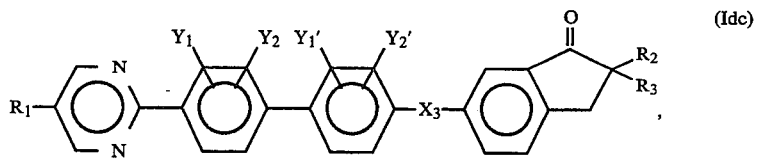
(Idc)

wherein
$R_1$, $R_2$ and $R_3$ independently denote hydrogen, halogen, —CN,

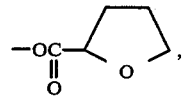

or a linear or branched alkyl group having 1–18 carbon atoms capable of including one or non-neighboring two or more —CH$_2$— groups which can be replaced with —O—, —S—,

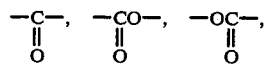

—CH=CH— or —C≡C—, the linear or branched alkyl group being capable of including hydrogen which can be replaced with fluorine;
$X_1$, $X_2$ and $X_3$ independently denote a single bond,

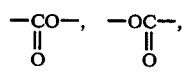

—CH$_2$O— or —OCH$_2$—; and $Y_1$, $Y_2$, $Y_1'$ and $Y_2'$ independently denote H, F, Cl, Br, CH$_3$, CF$_3$ or CN.

In the above formulas (Iaa) to (Idc), $Y_1$, $Y_2$, $Y_1'$ and $Y_2'$ may preferably be H, F, Cl, Br or CF$_3$, particularly H or F.

$R_1$, $R_2$ and $R_3$ in the formula (I) may preferably be selected from the following groups (i) to (vii):

(i) n—C$_a$H$_{2a+1}$—X$_4$—,

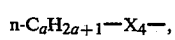  (i)

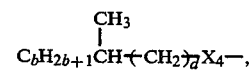  (ii)

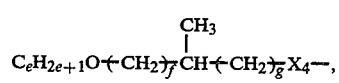  (iii)

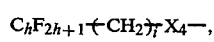  (iv)

  (v)

H—, and  (vi)

F—,  (vii)

(vi) H—, and
(vii) F—,
wherein a is an integer of 1–16; d, g and i are an integer of 0–7; b, e and h are an integer of 1–8, f and k are 0 or 1, j is an integer of 1–15; and $X_4$ denotes a single bond, —O—,

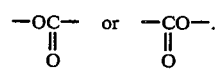

Further, $R_3$ in the formula (I) may more preferably be hydrogen or a linear alkyl group having 1–5 carbon atoms.

Preferred examples of the optically active compound of the formula (II) may include those of the following formulas (IIa) to (IId) having one or two linkage groups:

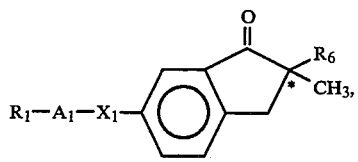  (IIa)

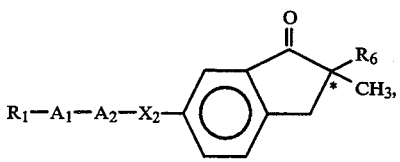  (IIb)

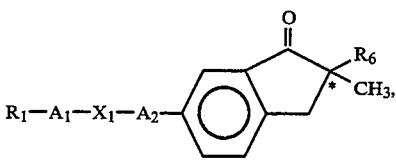  (IIc)

and

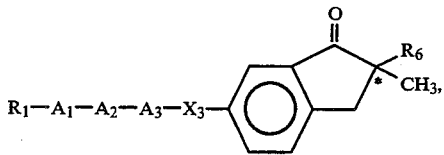  (IId)

wherein
$R_1$ denotes hydrogen, halogen, —CN,

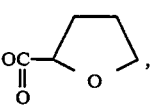

or a linear or branched alkyl group having 1–18 carbon atoms capable of including one or non-neighboring two or more —CH$_2$— groups which can be replaced with —O—, —S—,

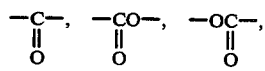

—CH=CH— or —C≡C—, the linear or branched alkyl group being capable of including hydrogen which can be replaced with fluorine;

$R_6$ denotes a linear alkyl group having 2-16 carbon atoms;

$X_1$, $X_2$ and $X_3$ independently denote a single bond,

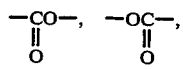

—CH$_2$O— or —OCH$_2$—;

$A_2$ and $A_3$ independently denote a single bond,

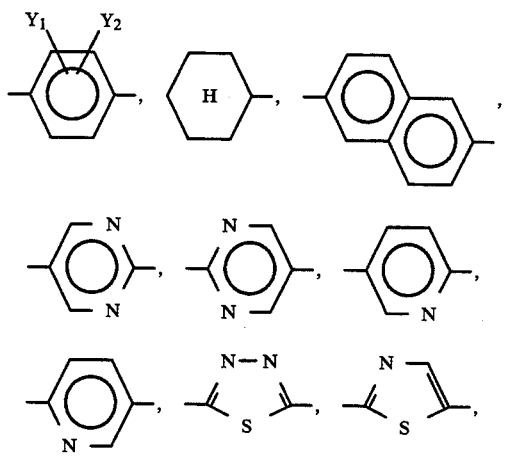

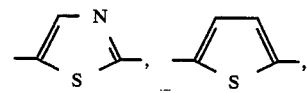

wherein $Y_1$ and $Y_2$ independently denote H, F, Cl, Br, CH$_3$, CF$_3$ or CN, and $Z_1$ denotes O or S; and $A_1$ denotes

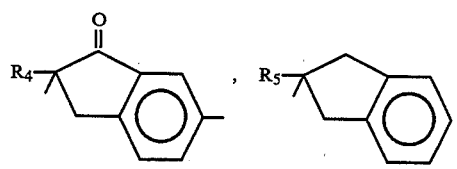

or $A_2$, wherein $R_4$ and $R_5$ independently denote hydrogen, or a linear or branched alkyl group having 1-18 carbon atoms; and \* denotes a location of an optically active center.

In view of various properties such as viscosity, a temperature range of a mesomorphic phase, compatibility, and an alignment characteristic, further preferred examples of the optically active compound of the formula (II) may include those of the following formulas (IIaa) to (IIdc):

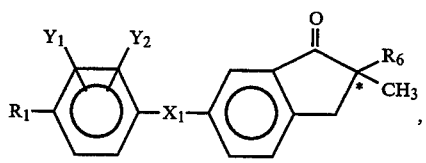 (IIaa)

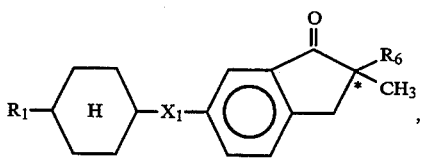 (IIab)

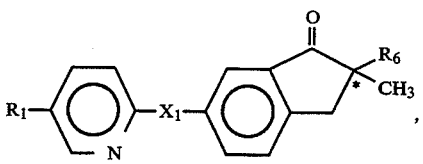 (IIac)

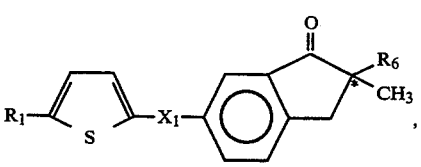 (IIad)

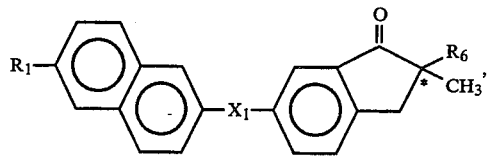
(IIae)
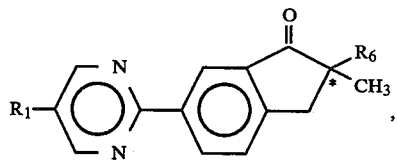
(IIaf)
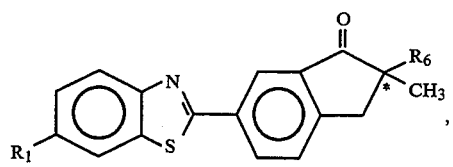
(IIag)
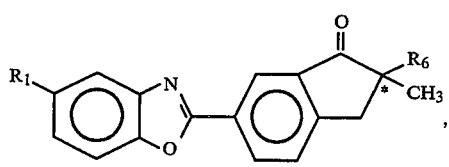
(IIah)
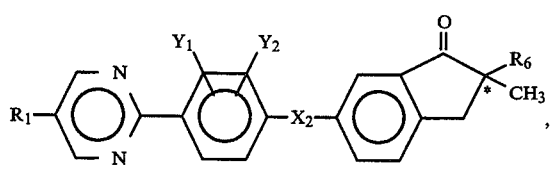
(IIba)
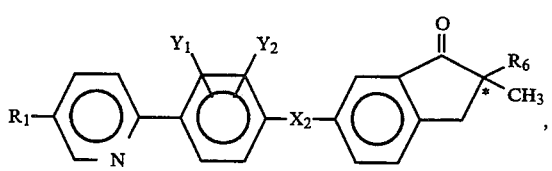
(IIbb)
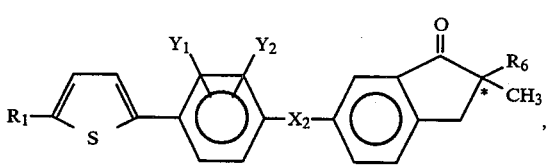
(IIbc)
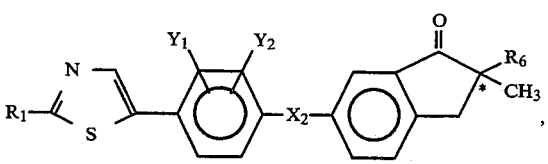
(IIbd)
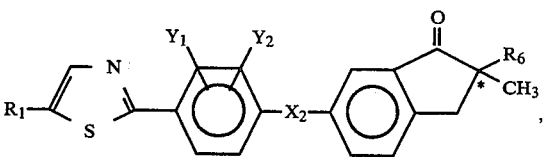
(IIbe)
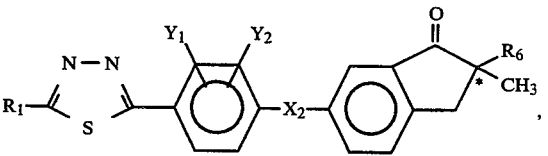
(IIbf)

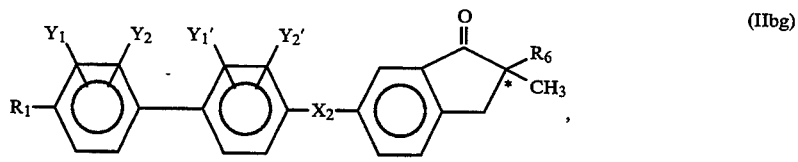 (IIbg)
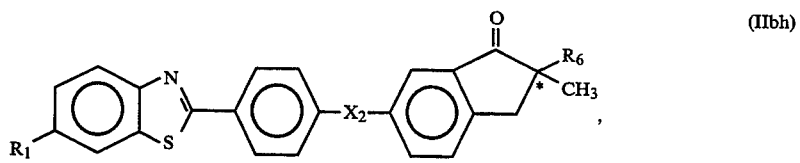 (IIbh)
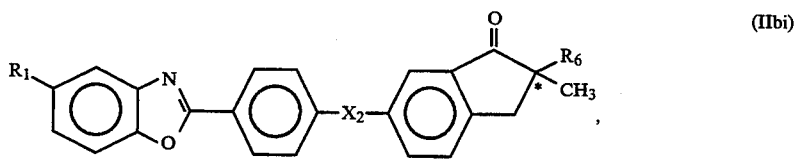 (IIbi)
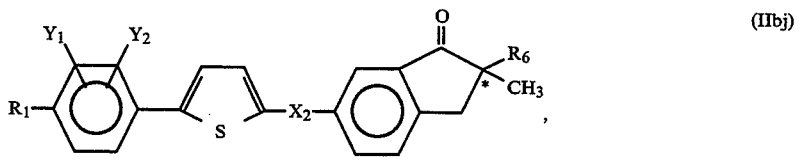 (IIbj)
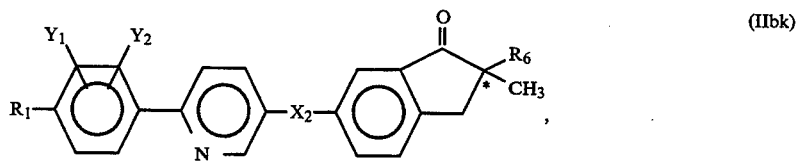 (IIbk)
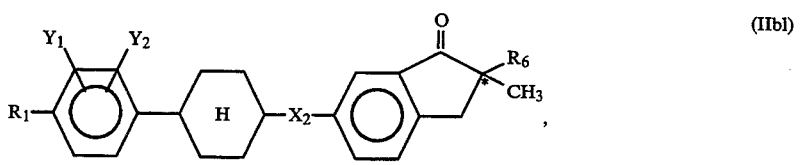 (IIbl)
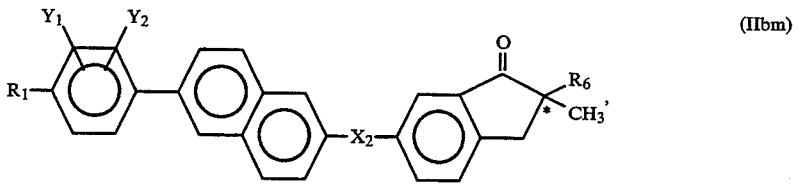 (IIbm)
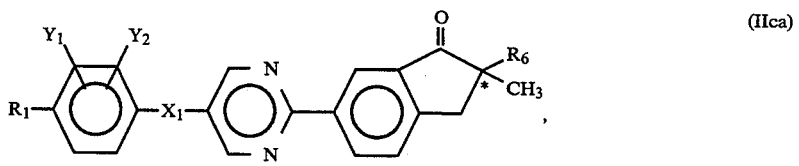 (IIca)
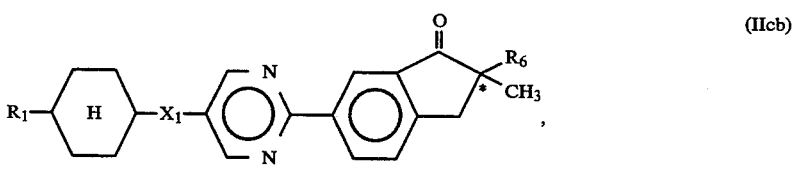 (IIcb)

-continued
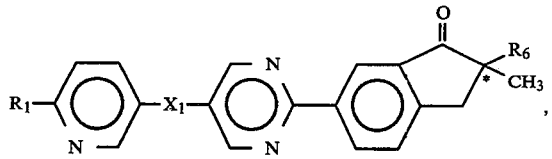 (IIcc)
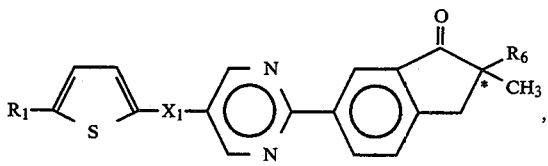 (IIcd)
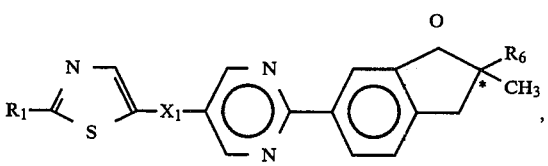 (IIce)
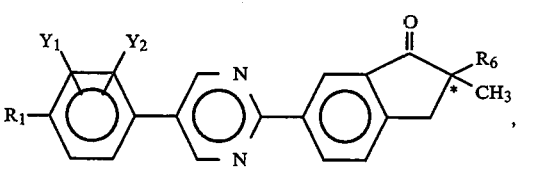 (IIcf)
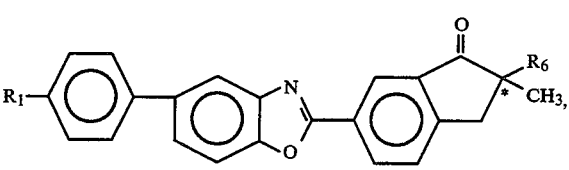 (IIcg)
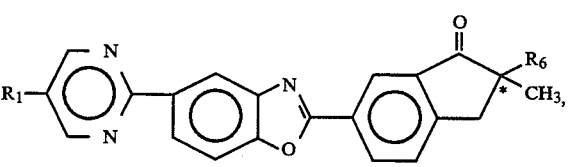 (IIch)
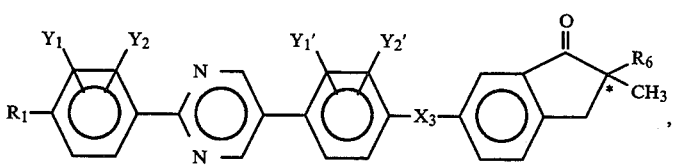 (IIda)
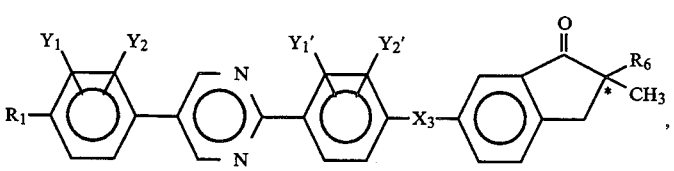 (IIdb)
and
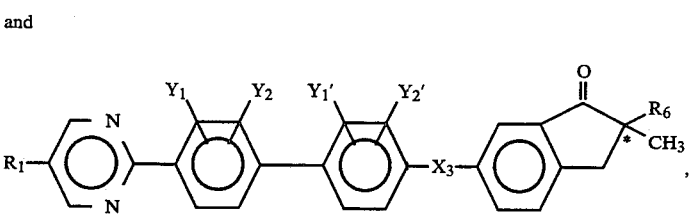 (IIdc)
wherein
$R_1$ denotes hydrogen, halogen, —CN,

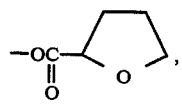

or a linear or branched alkyl group having 1–18 carbon atoms capable of including one or non-neighboring two or more —CH$_2$— groups which can be replaced with —O—, —S—,

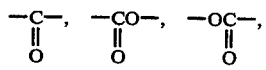

—CH=CH— or —C≡C—, the linear or branched alkyl group being capable of including hydrogen which can be replaced with fluorine;

R$_6$ denotes a linear alkyl group having 2–16 carbon atoms;

X$_1$, X$_2$ and X$_3$ independently denote a single bond,

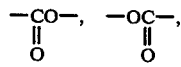

—CH$_2$O— or —OCH$_2$—;

Y$_1$, Y$_2$, Y$_1'$ and Y$_2'$ independently denote H, F, Cl, Br, CH$_3$, CF$_3$ or CN; and

* denotes a location of an optically active center.

In the above formulas (IIaa) to (IIdc), Y$_1$, Y$_2$, Y$_1'$ and Y$_2'$ may preferably be H, F, Cl, Br or CF$_3$, particularly H or F.

R$_1$ in the formula (II) may preferably be selected from the following groups (i) to (vii):

(i) n—C$_a$H$_{2a+1}$—X$_4$—, $$\text{n-}C_aH_{2a+1}\text{—}X_4\text{—,} \qquad \text{(i)}$$

$$C_bH_{2b+1}\underset{|}{\overset{CH_3}{CH}}(CH_2)_dX_4\text{—,} \qquad \text{(ii)}$$

$$C_eH_{2e+1}O(CH_2)_f\underset{|}{\overset{CH_3}{CH}}(CH_2)_gX_4\text{—,} \qquad \text{(iii)}$$

$$C_hF_{2h+1}(CH_2)_iX_4\text{—,} \qquad \text{(iv)}$$

$$C_jH_{2j+1}\underset{|}{\overset{F}{CH}}(CH_2)_kX_4\text{—,} \text{ and} \qquad \text{(v)}$$

$$\text{H—, and} \qquad \text{(vi)}$$

$$\text{F—,} \qquad \text{(vii)}$$

(vi) H—, and
(vii) F—,
wherein a is an integer of 1–16; d, g and i are an integer of 0–7; b, e and h are an integer of 1–8, f and k are 0 or 1, j is an integer of 1–15; and X$_4$ denotes a single bond, —O—,

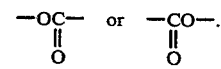

The mesomorphic compound of the abovementioned formula (I) may generally be synthesized through the following reaction schemes A and B.

Scheme A

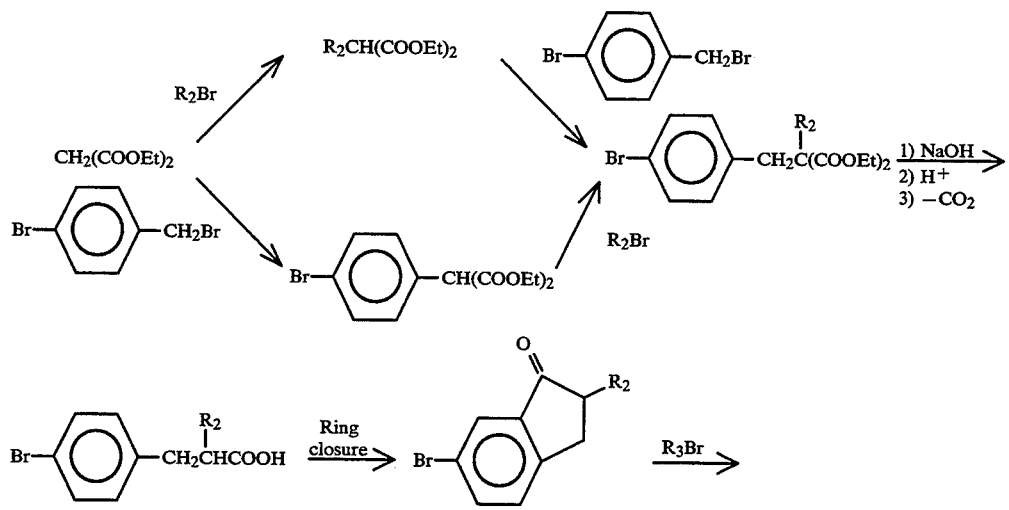

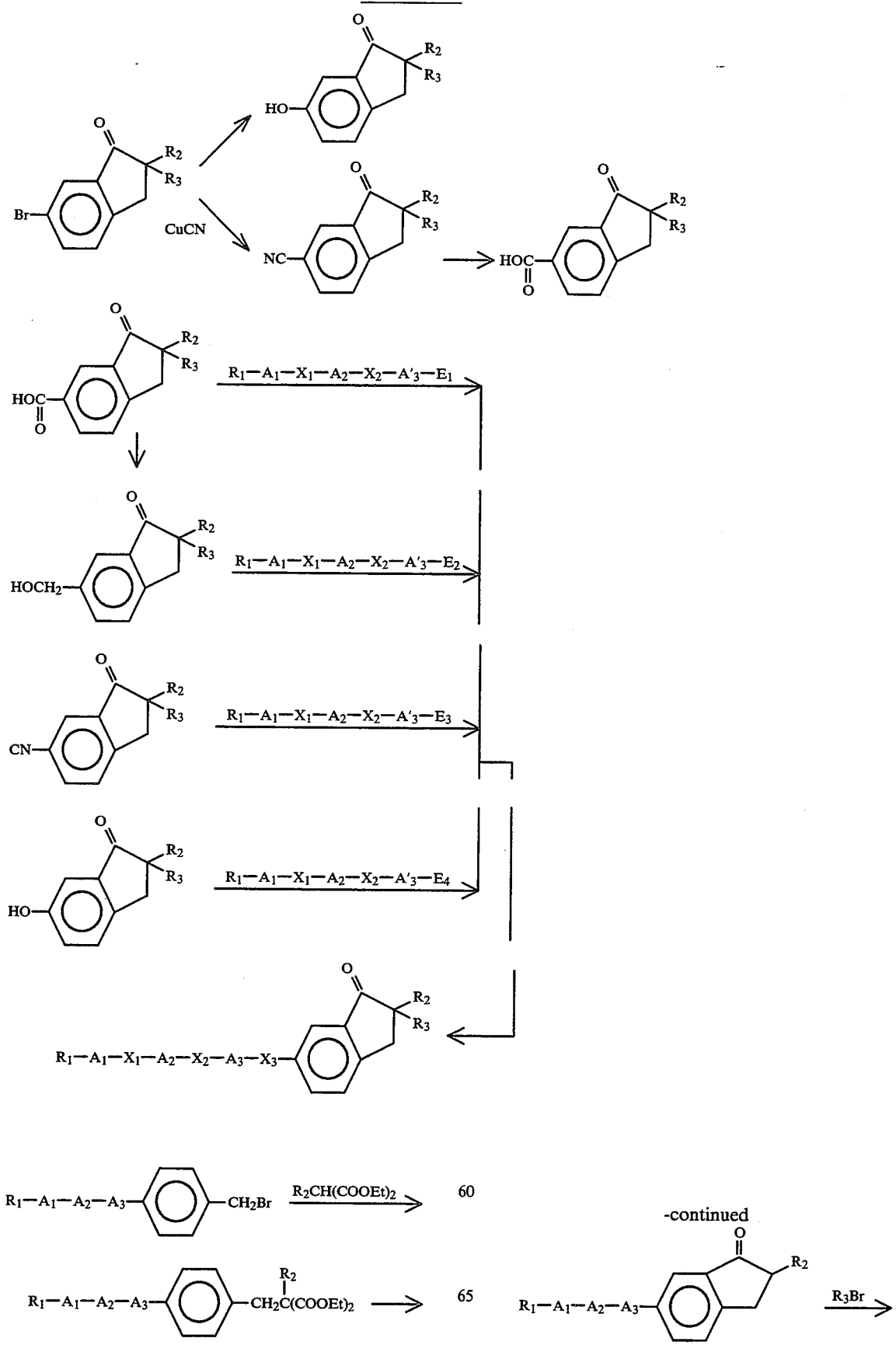
-continued
Scheme A

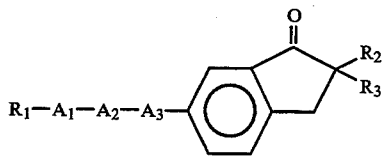

In the above reaction schemes A and B, $R_1$, $R_2$, $R_3$, $A_1$, $A_2$, $A_3$, $Z_1$, $X_2$ and $X_3$ have the meanings given above. In a case where $X_3$ is not a single bond, $E_1$ to $E_4$ are appropriate groups, such as —OH, —COOH, —Br and —I, for forming $X_3$ and $A_3'$ denotes $A_3$. In a case where $X_3$ is a single bond and $A_3$ is a heterocycle, $E_1$——$A_3'$— to $E_4$—$A_3'$— are appropriate groups, such as

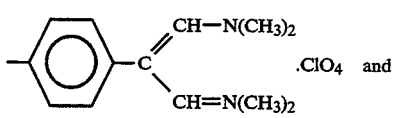

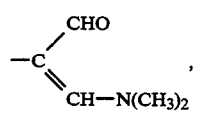

for forming $A_3$.

The optically active compound of the abovementioned formula (II) may be obtained from optically active 2-alkyl-2-methyl-1-indanone-6-carboxylic acid (as disclosed in Japanese Patent Appln. No. 73004/1992 (Feb. 26, 1992 filed)), represented by the following formula:

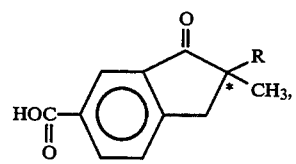

wherein R denotes a linear alkyl group having 2–16 carbon atoms and * denotes a location of an optically active center.

The optically active compound of the formula (II) may generally be synthesized through the following reaction scheme.

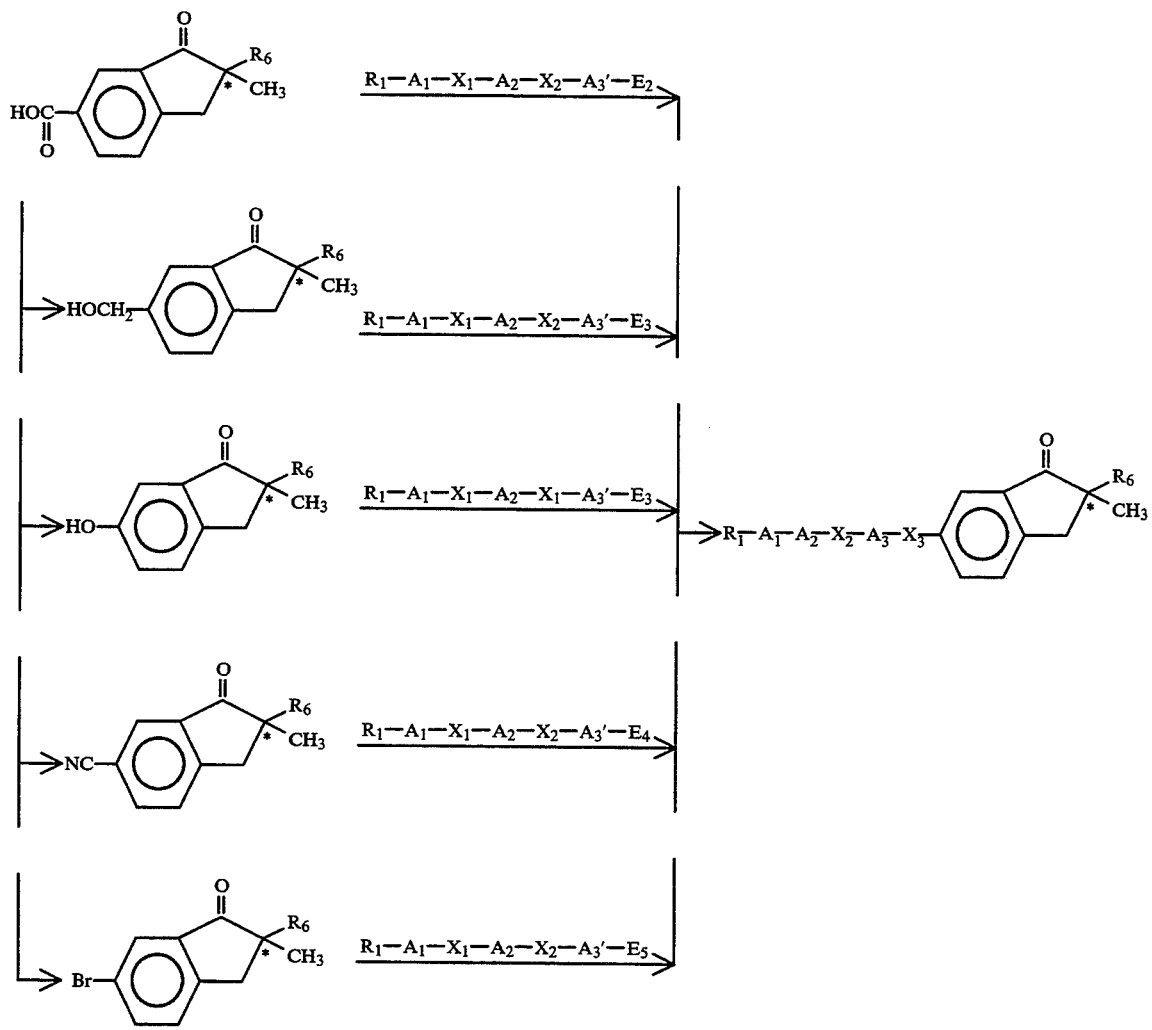

In the above reaction scheme $R_1$, $R_6$, $A_1$, $A_2$, $A_3$, $X_1$, $X_2$ and $X_3$ have the meanings given above. In a case where $X_3$ is not a single bond, $E_1$ to $E_5$ are appropriate groups, such as —OH, —COOH, —Br and —I, for forming $X_3$ and $A_3'$ denotes $A_3$. In a case where $X_1$ is a single bond $E_1-A_3'-$ to $E_5-A_3'-$ are appropriate groups, such as
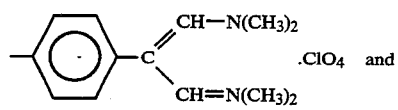   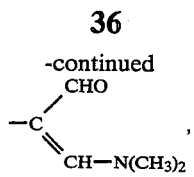
for forming $A_3$.
Specific examples of the mesomorphic (or optically active) compounds represented by the formula (I) or (II) may include those shown in the following structural formulas.
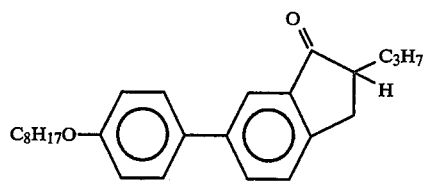  (1)
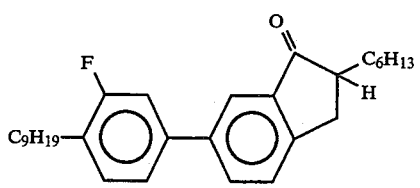  (2)
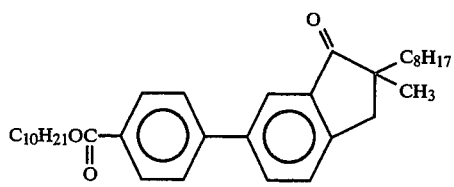  (3)
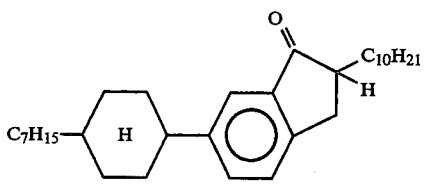  (4)
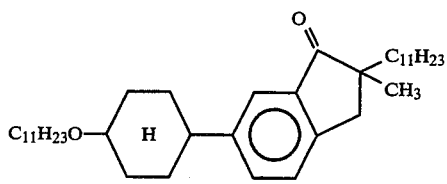  (5)
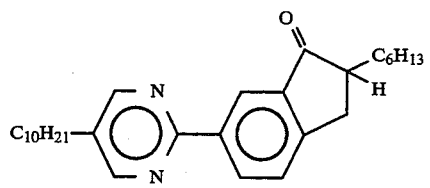  (6)
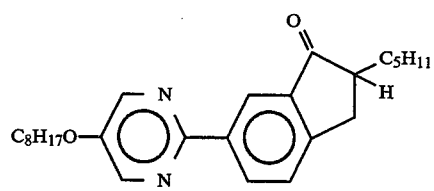  (7)

-continued
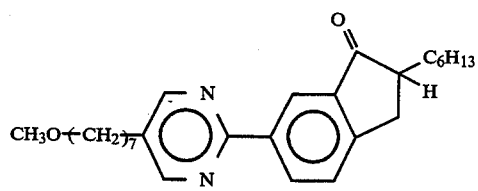 (8)
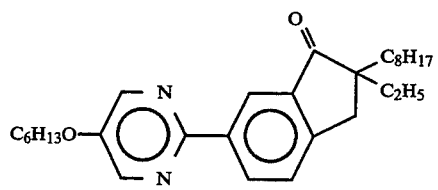 (9)
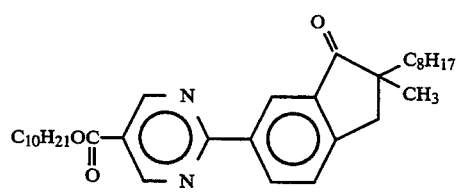 (10)
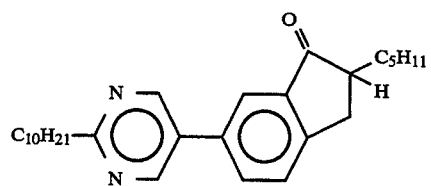 (11)
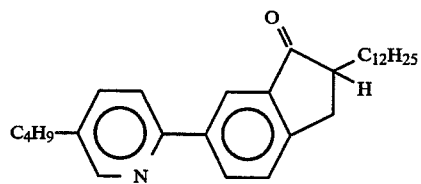 (12)
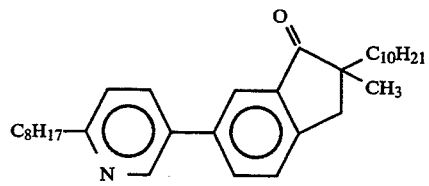 (13)
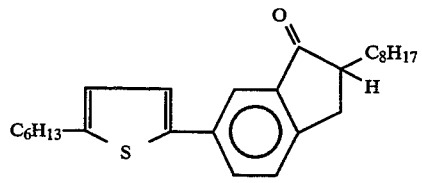 (14)
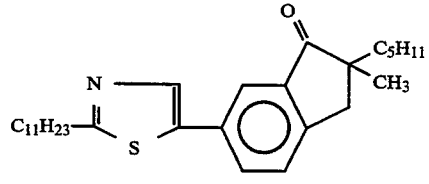 (15)

-continued
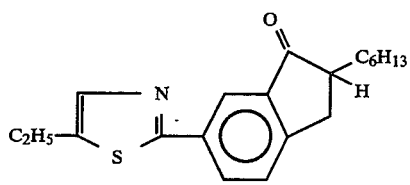 (16)
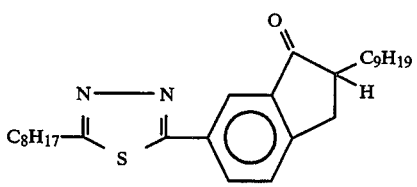 (17)
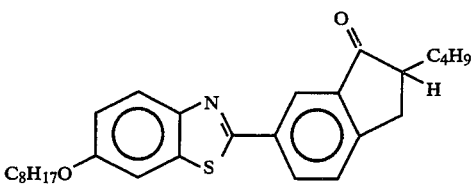 (18)
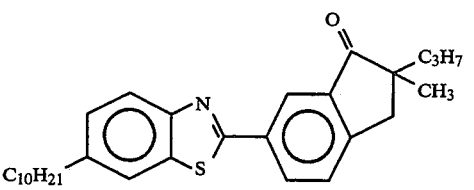 (19)
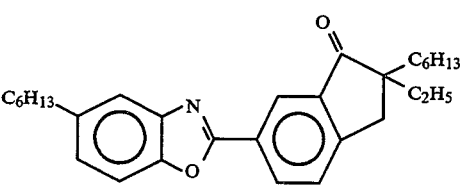 (20)
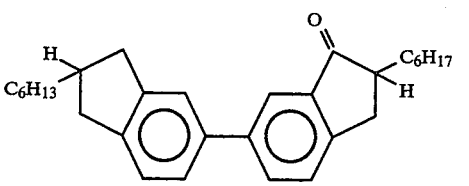 (21)
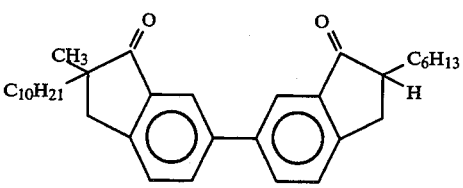 (22)
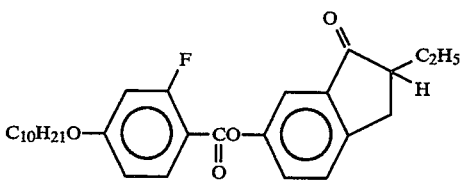 (23)
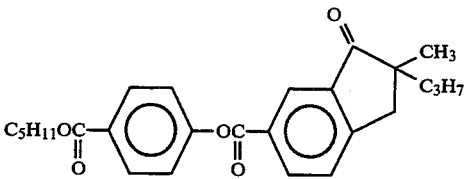 (24)

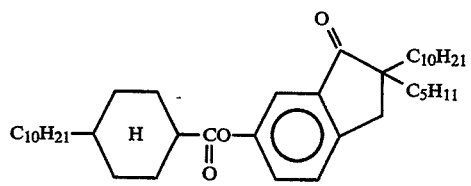 (25)
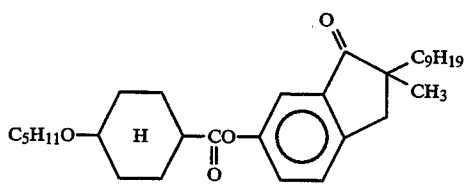 (26)
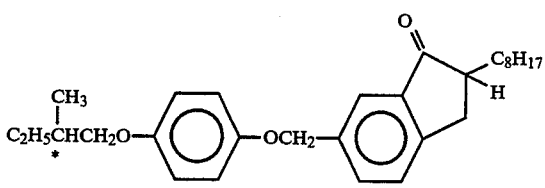 (27)
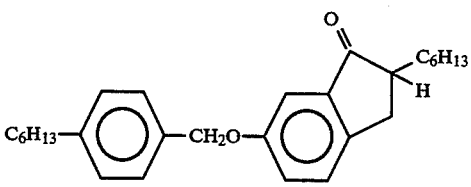 (28)
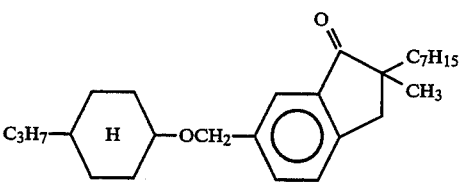 (29)
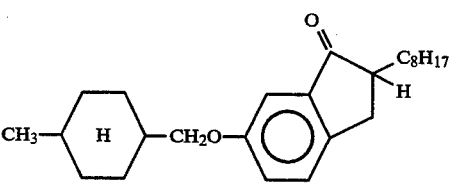 (30)
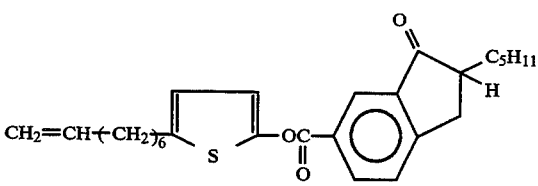 (31)
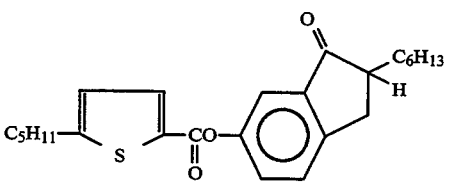 (32)
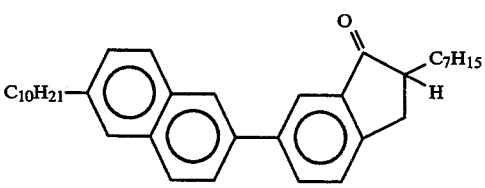 (33)

-continued
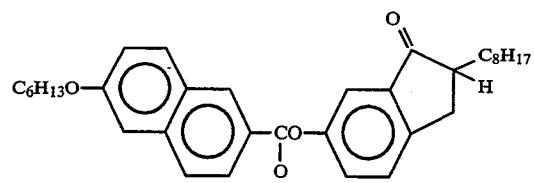 (34)
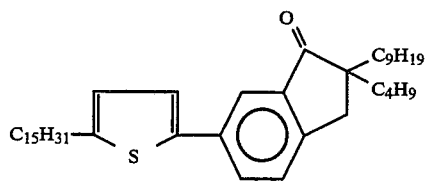 (35)
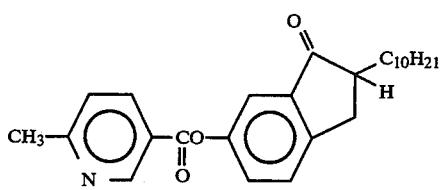 (36)
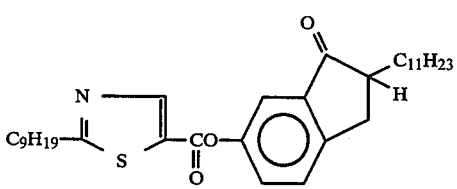 (37)
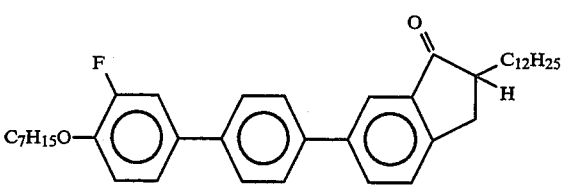 (38)
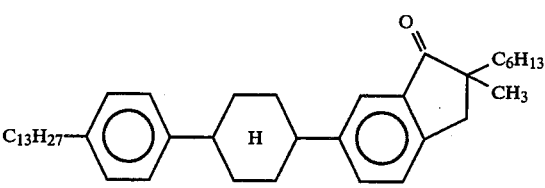 (39)
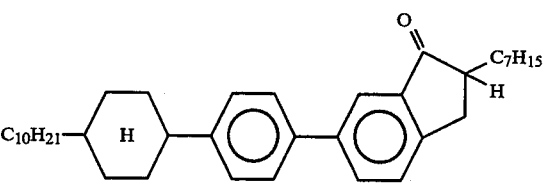 (40)
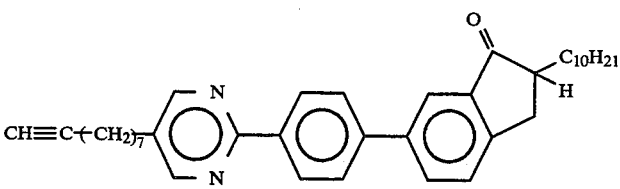 (41)

-continued
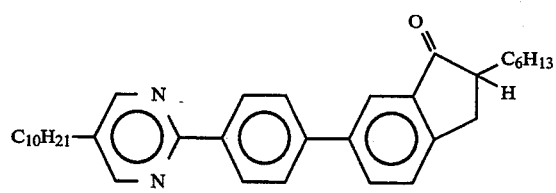
(42)
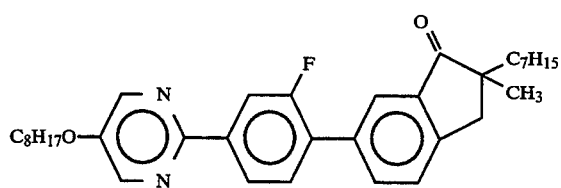
(43)
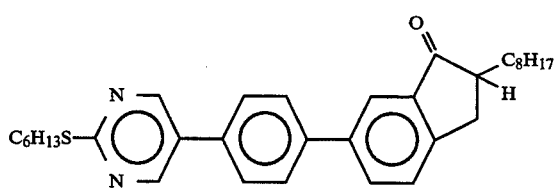
(44)
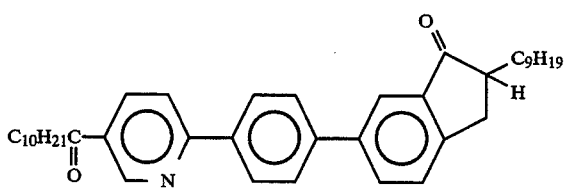
(45)
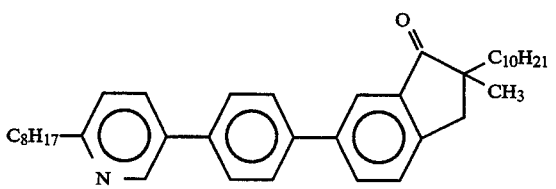
(46)
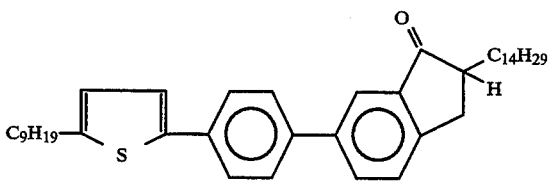
(47)
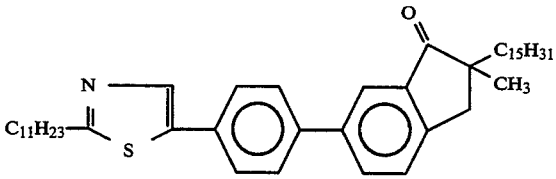
(48)
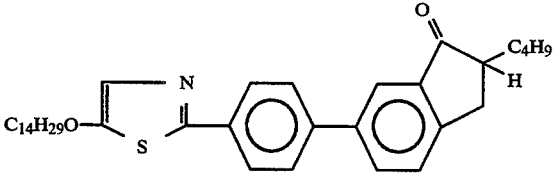
(49)

-continued
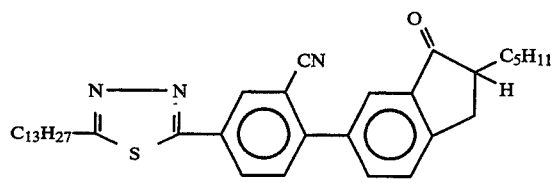 (50)
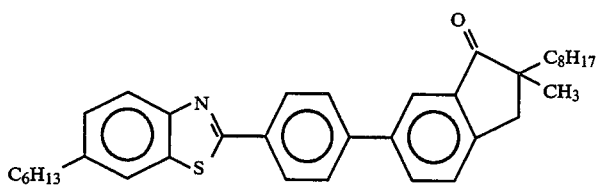 (51)
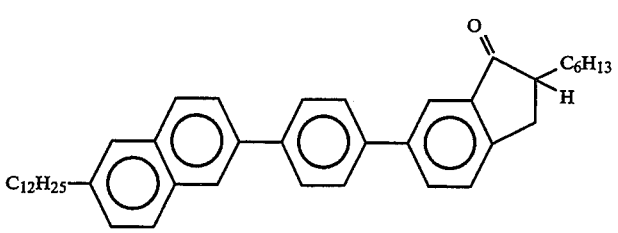 (52)
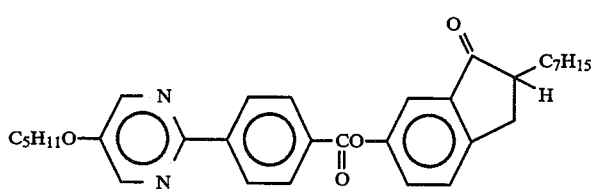 (53)
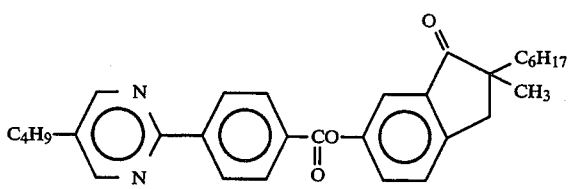 (54)
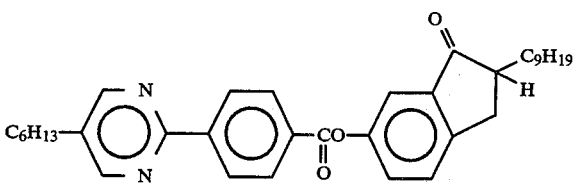 (55)
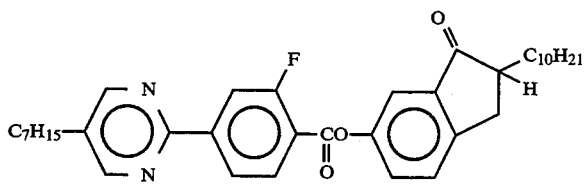 (56)
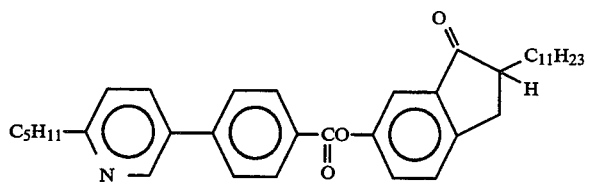 (57)

-continued
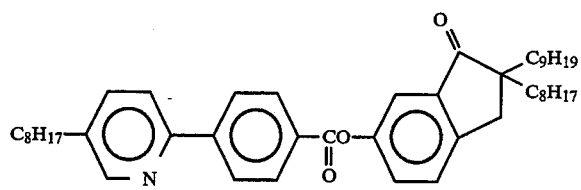 (58)
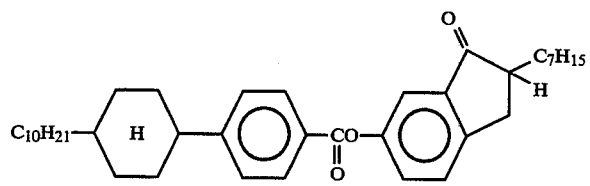 (59)
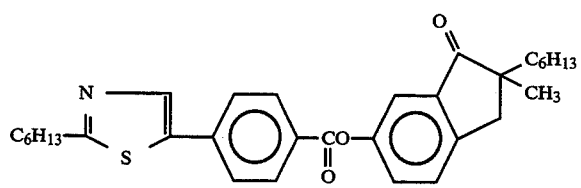 (60)
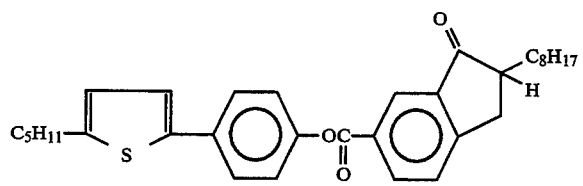 (61)
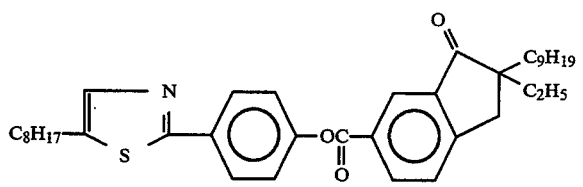 (62)
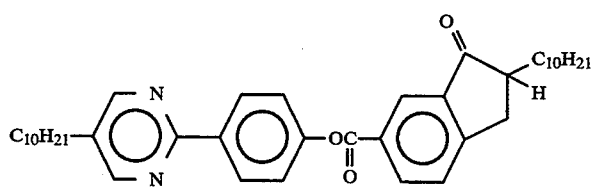 (63)
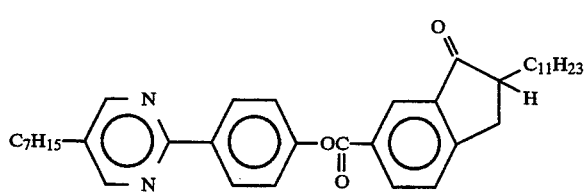 (64)
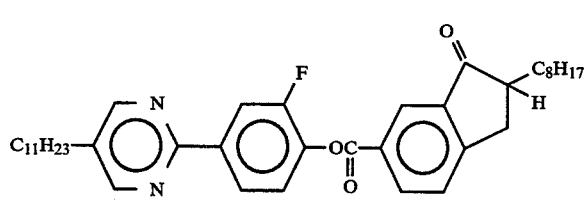 (65)

-continued
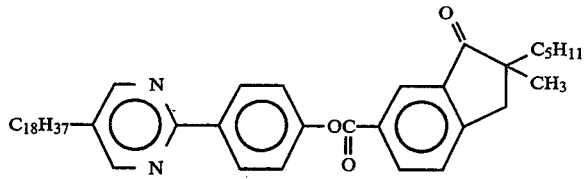
(66)
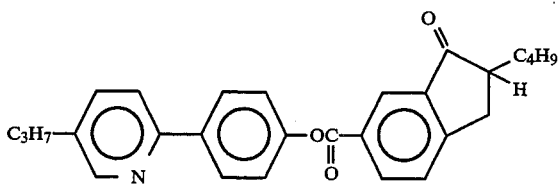
(67)
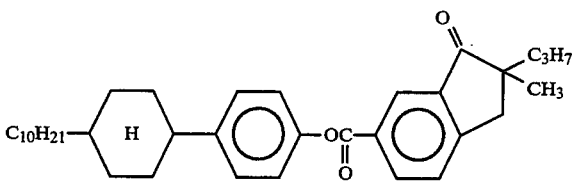
(68)
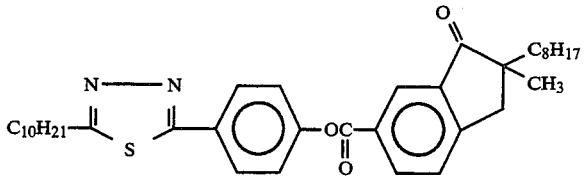
(69)
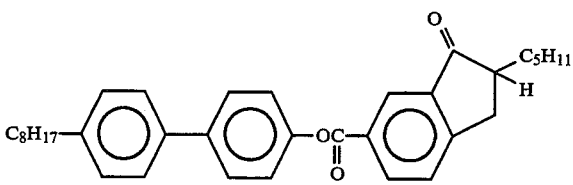
(70)
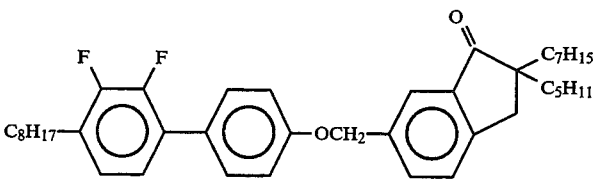
(71)
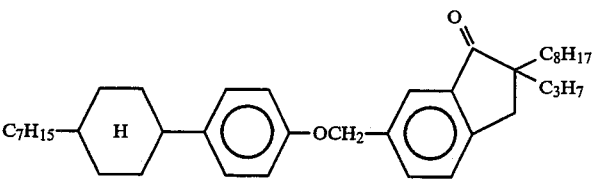
(72)
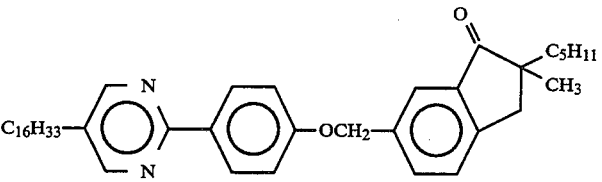
(73)
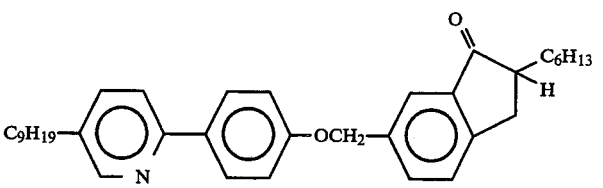
(74)

-continued
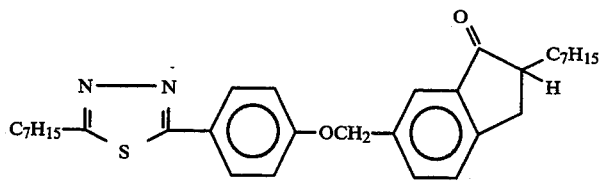 (75)
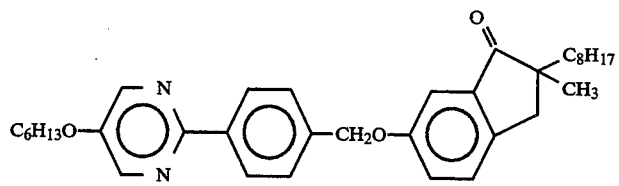 (76)
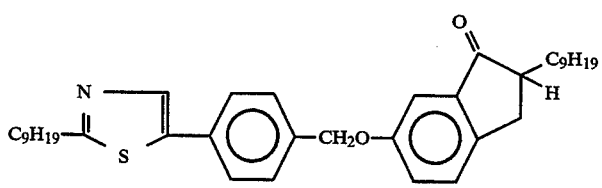 (77)
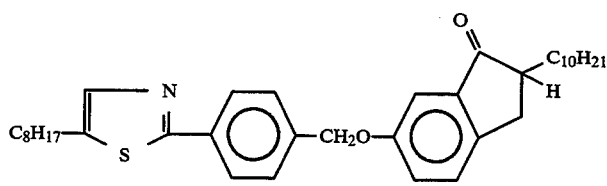 (78)
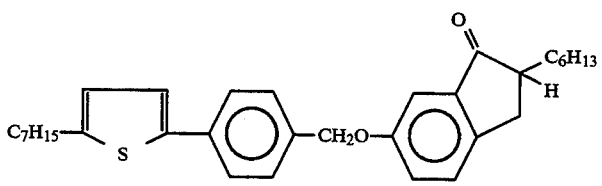 (79)
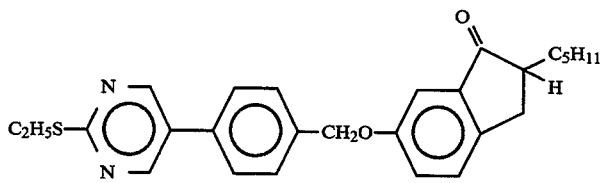 (80)
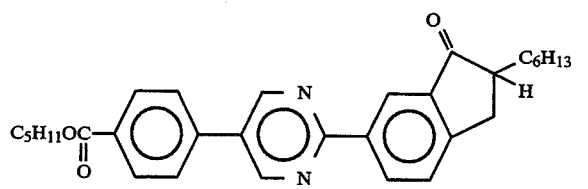 (81)
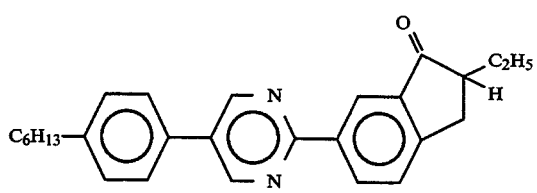 (82)

-continued
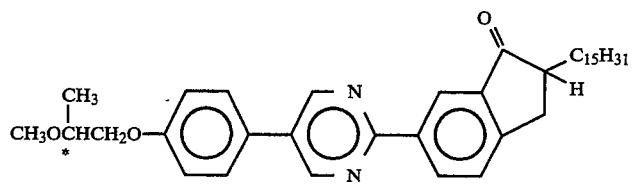 (83)
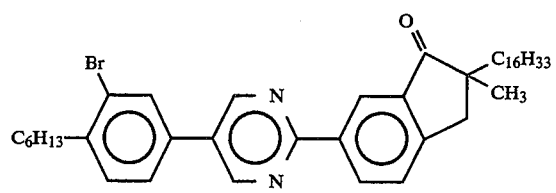 (84)
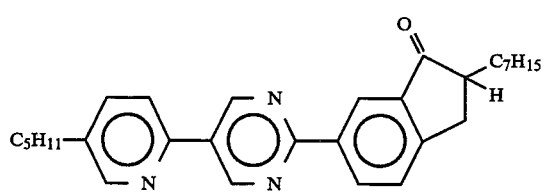 (85)
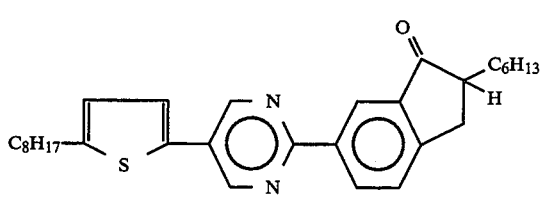 (86)
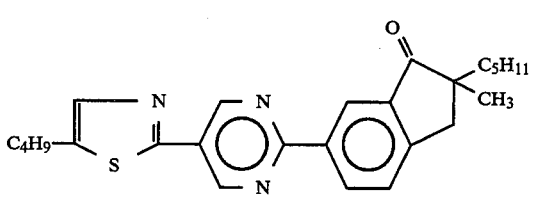 (87)
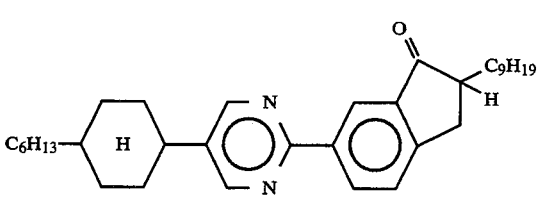 (88)
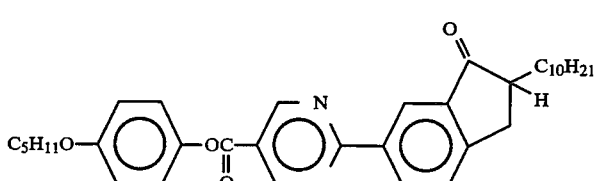 (89)
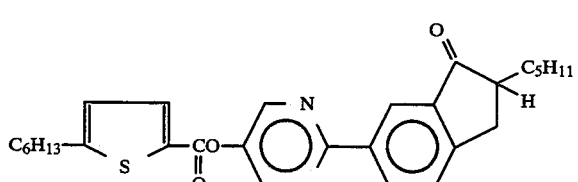 (90)

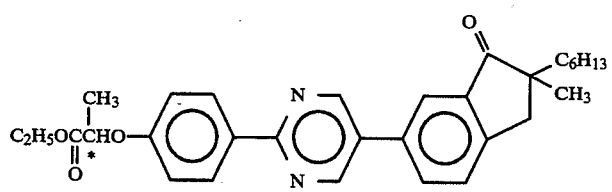 (91)
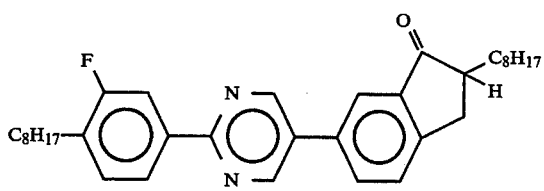 (92)
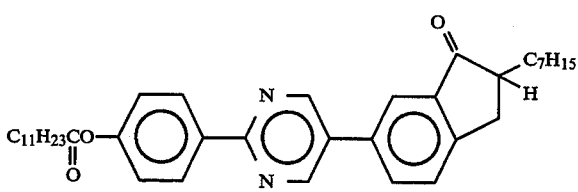 (93)
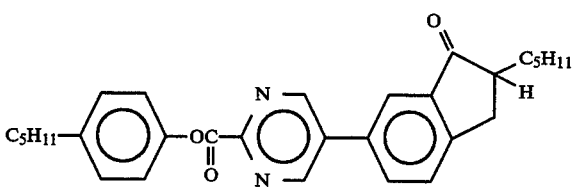 (94)
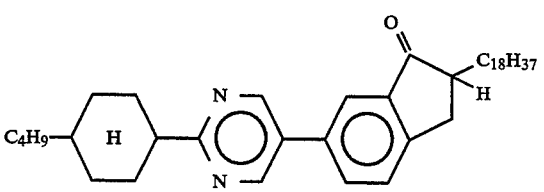 (95)
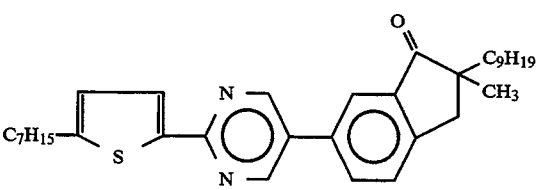 (96)
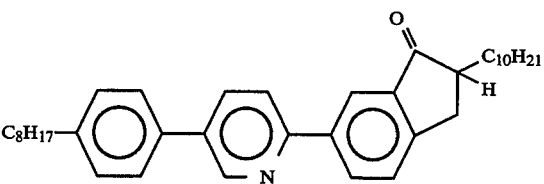 (97)
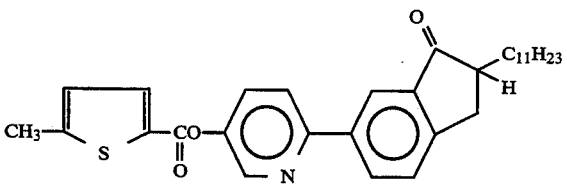 (98)

-continued
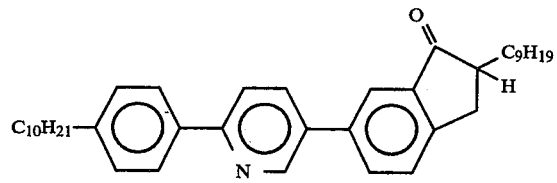 (99)
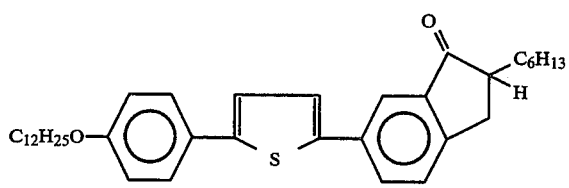 (100)
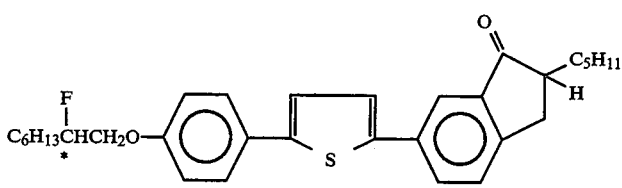 (101)
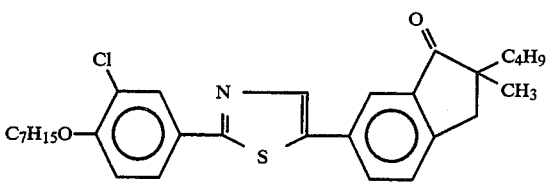 (102)
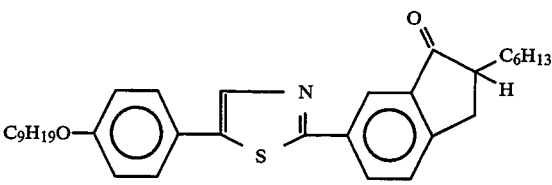 (103)
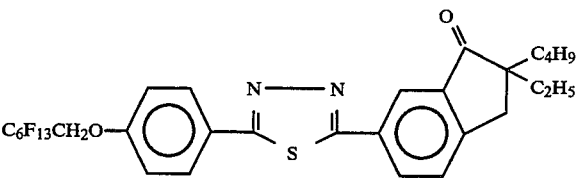 (104)
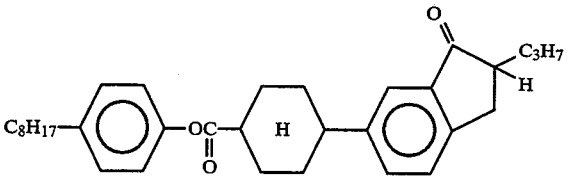 (105)
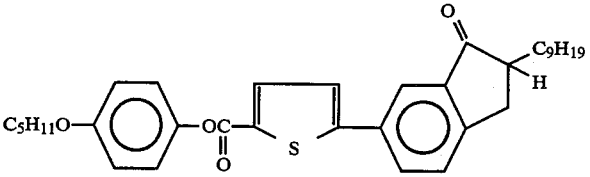 (106)
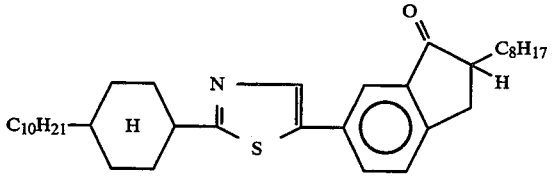 (107)

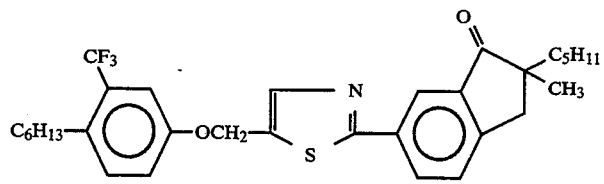
(108)
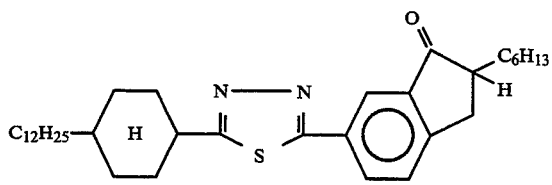
(109)
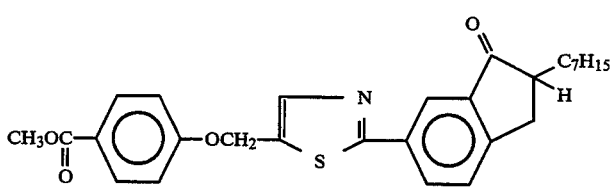
(110)
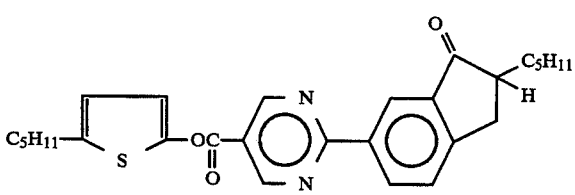
(111)
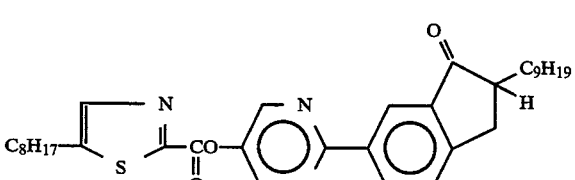
(112)
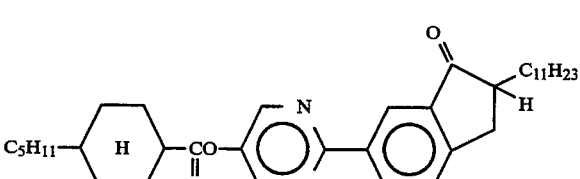
(113)
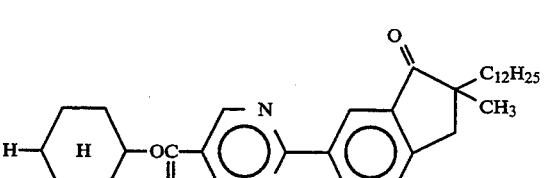
(114)
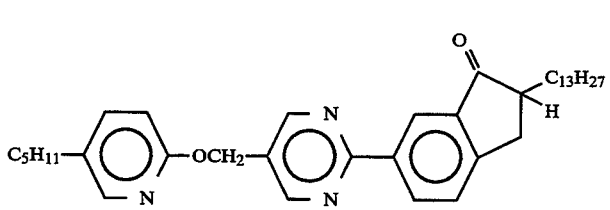
(115)

-continued
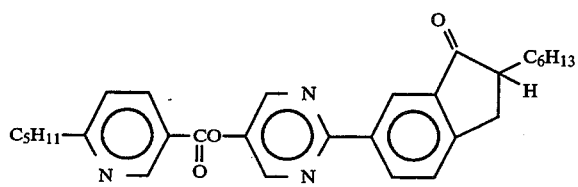 (116)
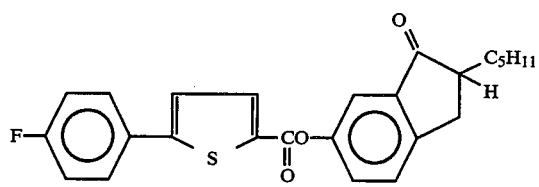 (117)
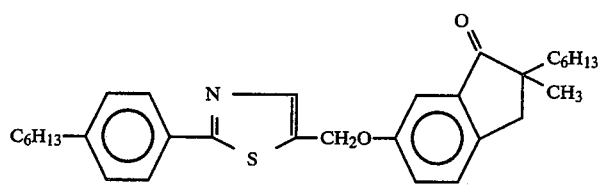 (118)
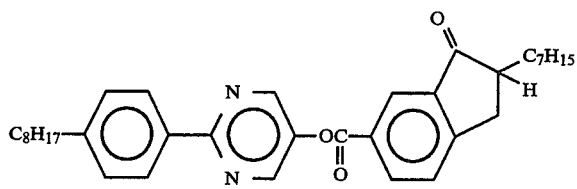 (119)
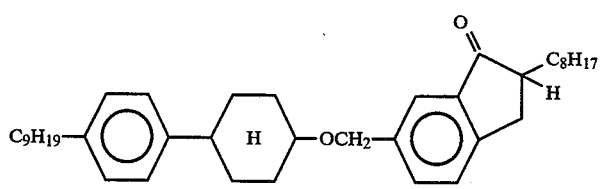 (120)
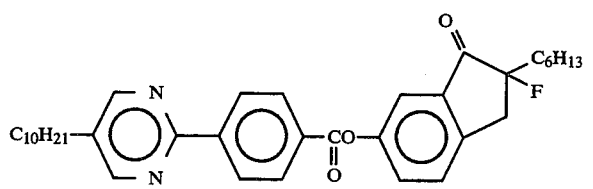 (121)
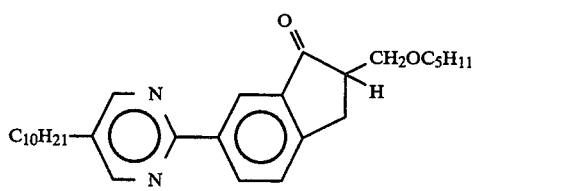 (122)
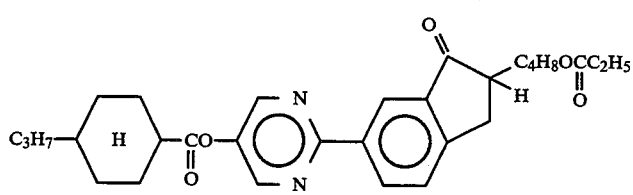 (123)

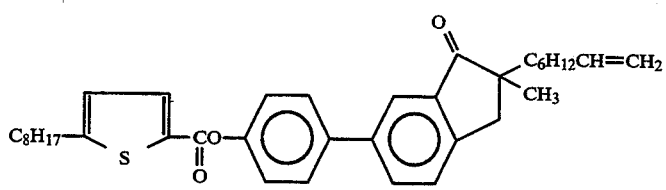 (124)
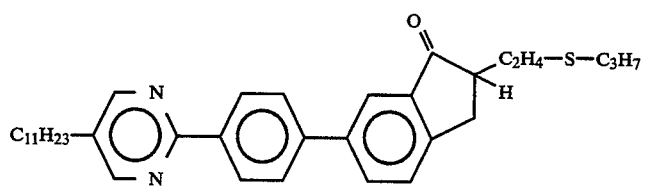 (125)
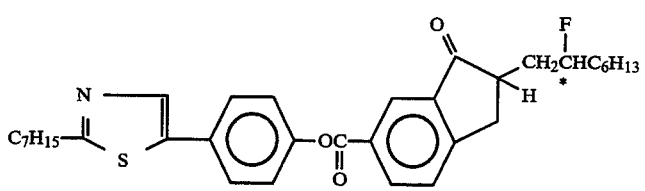 (126)
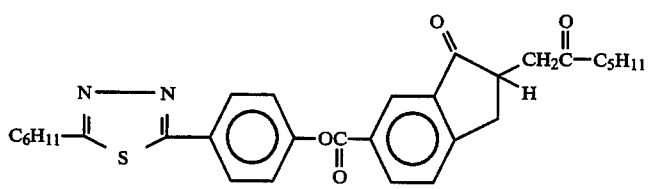 (127)
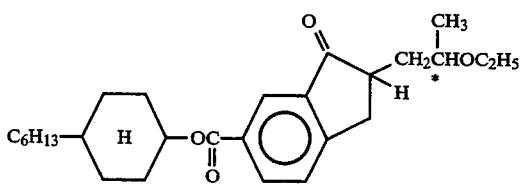 (128)
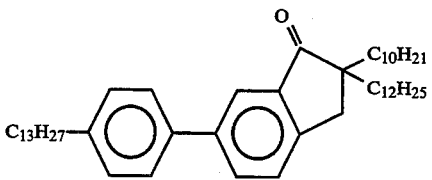 (129)
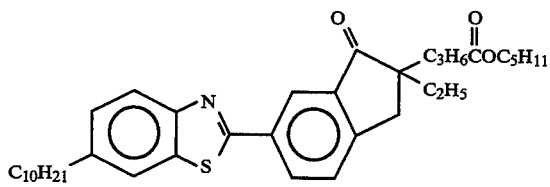 (130)
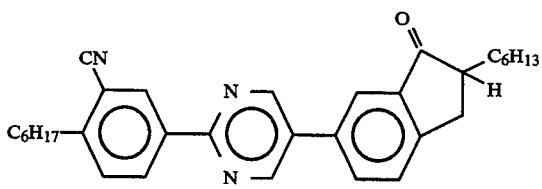 (131)

-continued
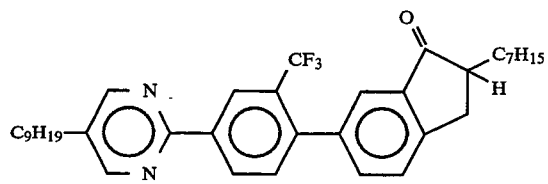(132)
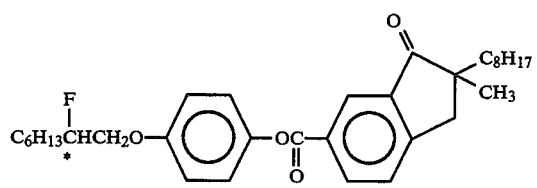(133)
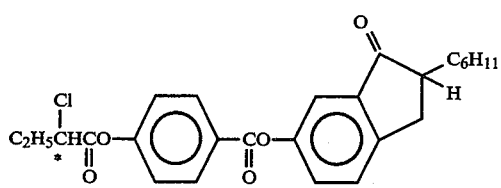(134)
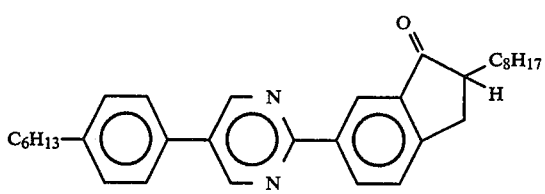(135)
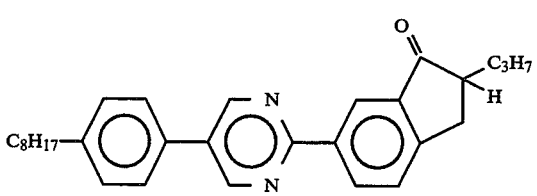(136)
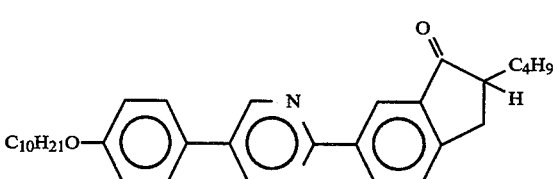(137)
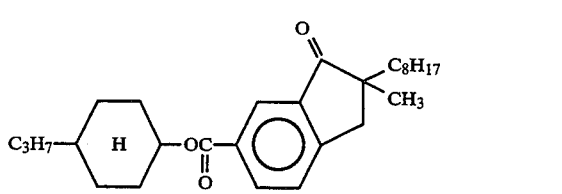(138)
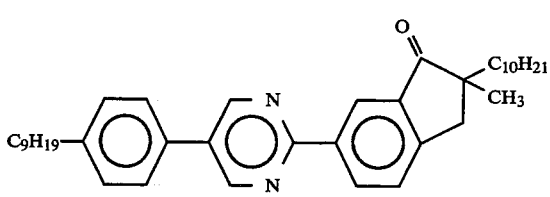(139)

-continued
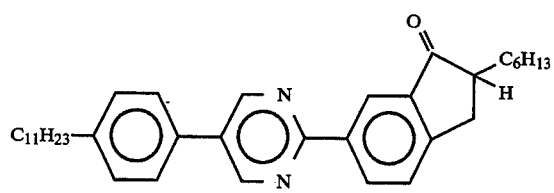
(140)
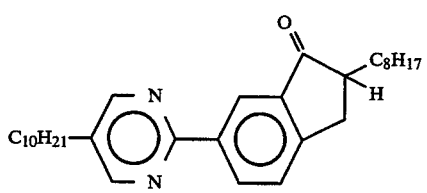
(141)
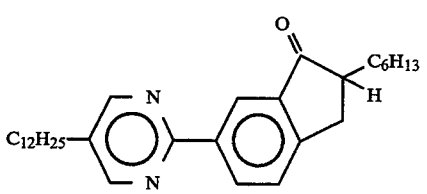
(142)
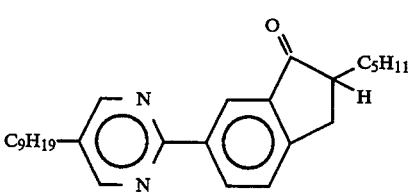
(143)
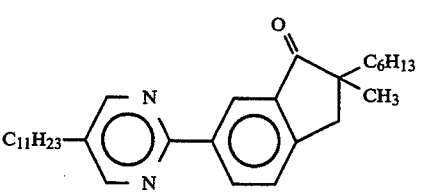
(144)
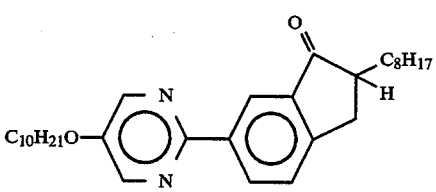
(145)
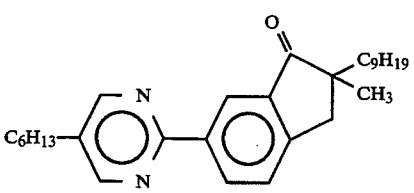
(146)
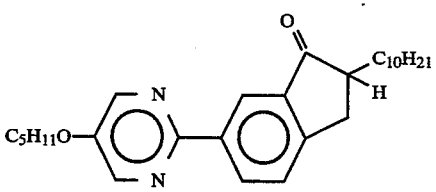
(147)

-continued
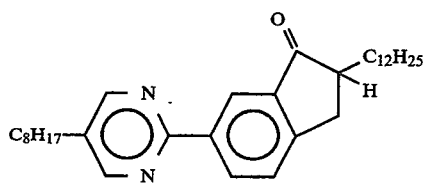 (148)
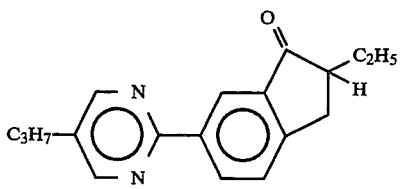 (149)
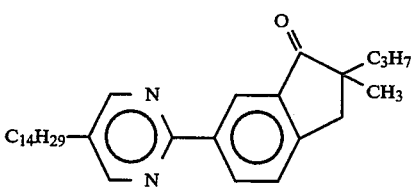 (150)
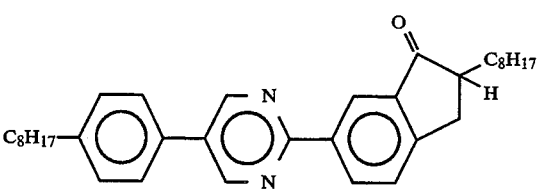 (151)
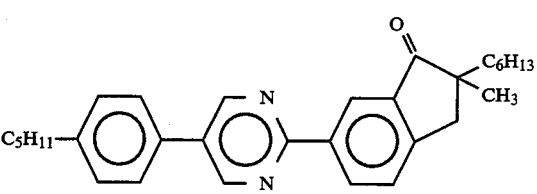 (152)
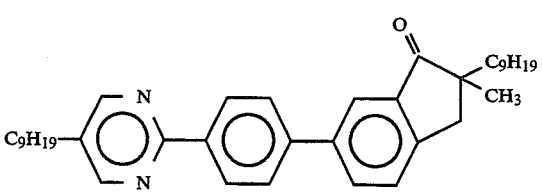 (153)
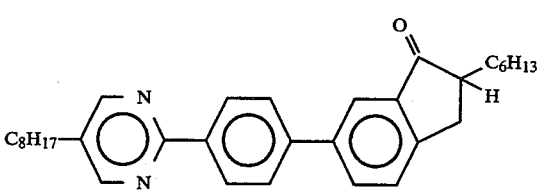 (154)
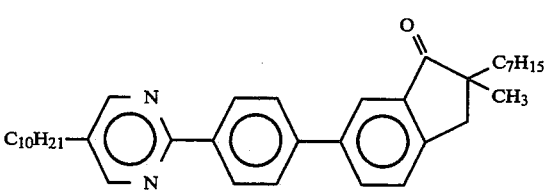 (155)

-continued
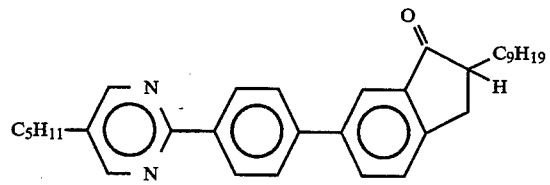 (156)
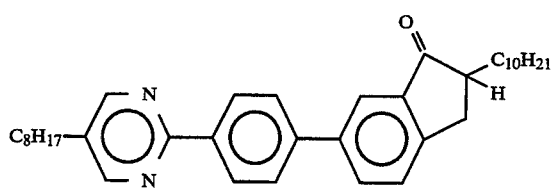 (157)
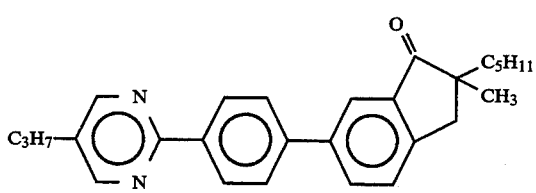 (158)
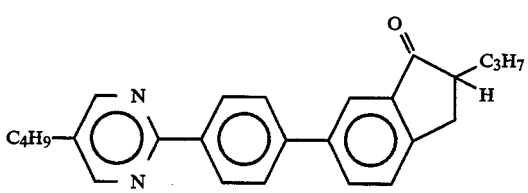 (159)
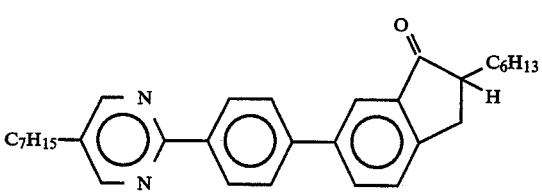 (160)
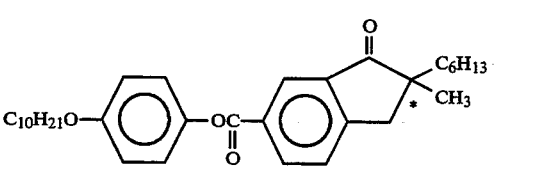 (161)
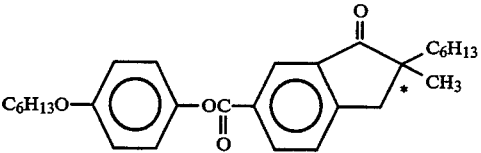 (162)
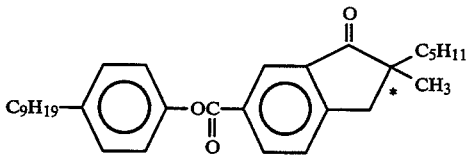 (163)
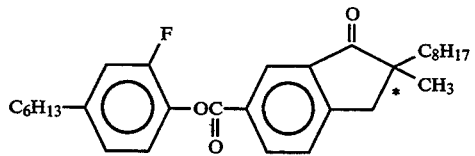 (164)

-continued
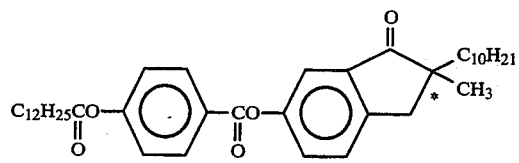 (165)
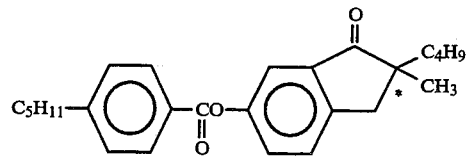 (166)
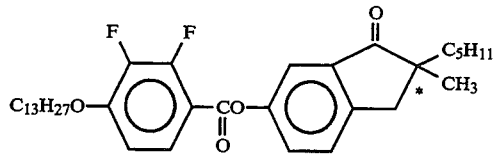 (167)
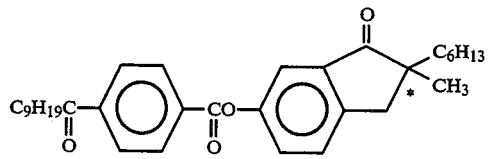 (168)
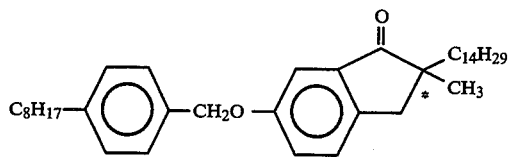 (169)
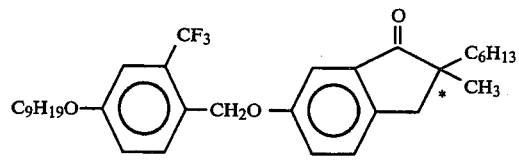 (170)
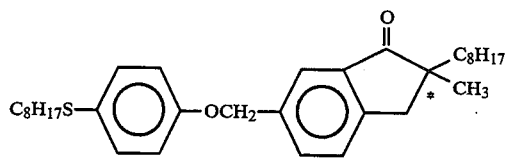 (171)
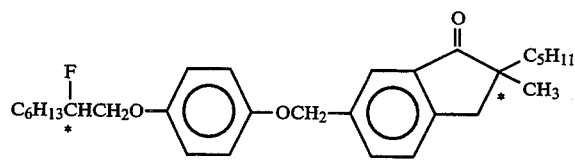 (172)
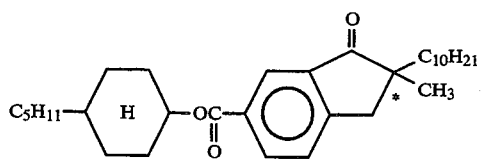 (173)
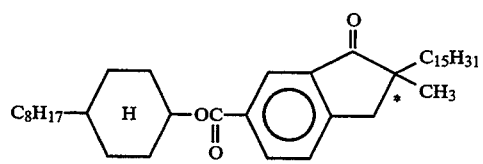 (174)

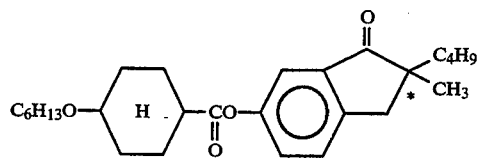 (175)
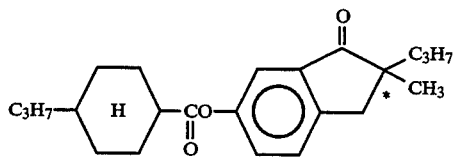 (176)
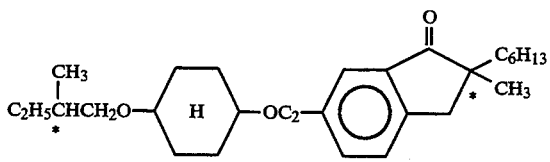 (177)
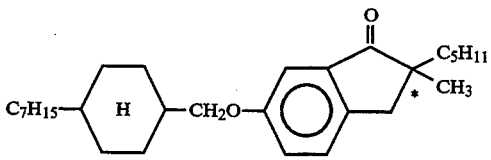 (178)
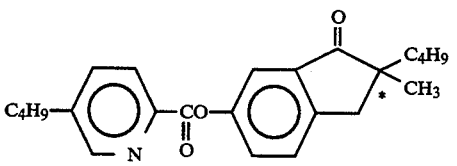 (179)
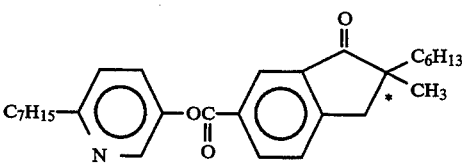 (180)
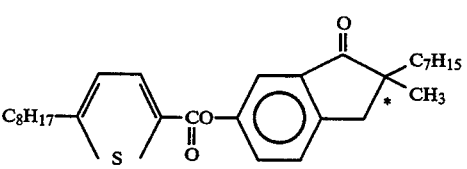 (181)
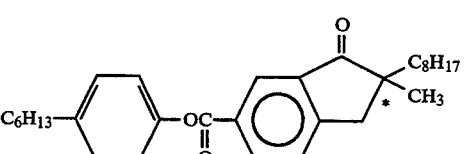 (182)
(183)
(184)

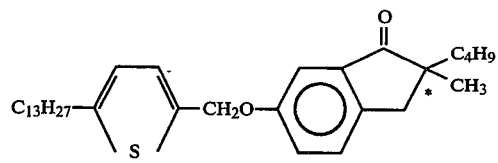 (185)
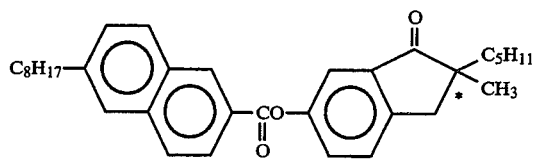 (186)
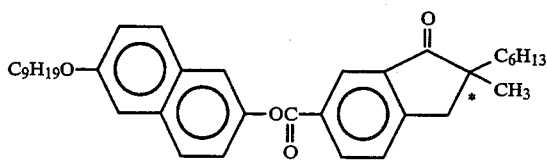 (187)
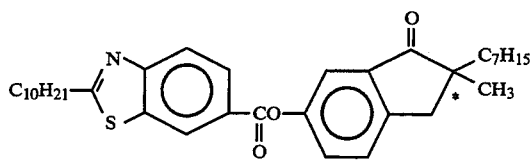 (188)
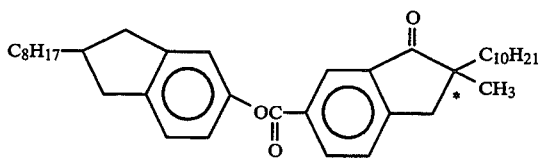 (189)
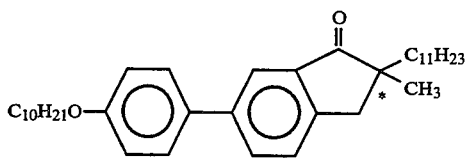 (190)
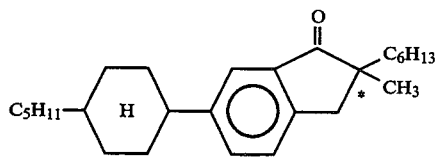 (191)
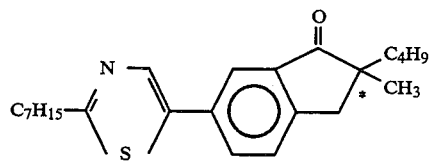 (192)
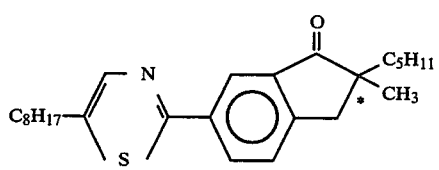 (193)

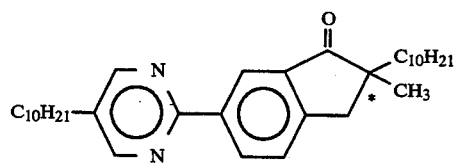
(194)
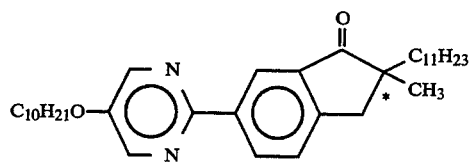
(195)
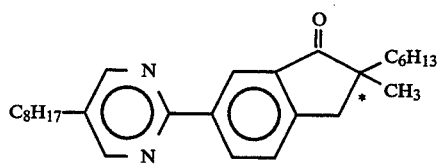
(196)
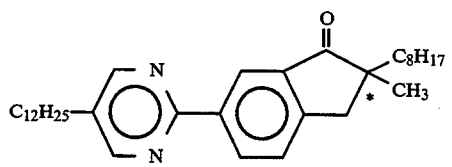
(197)
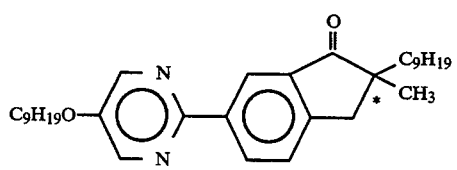
(198)
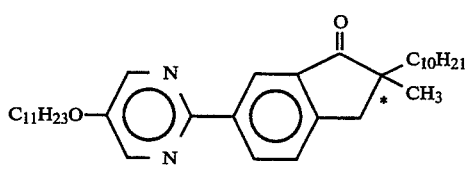
(199)
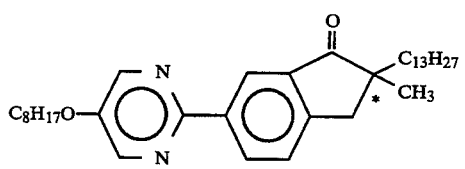
(200)
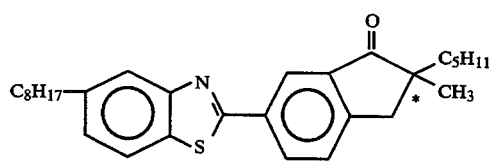
(201)
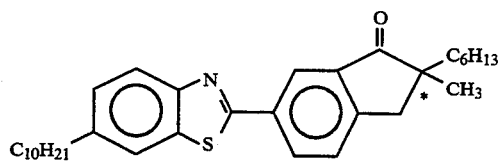
(202)

-continued
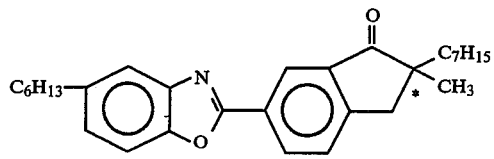 (203)
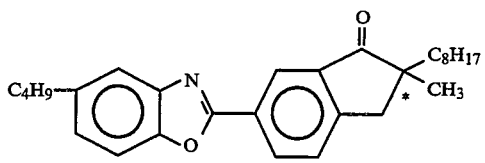 (204)
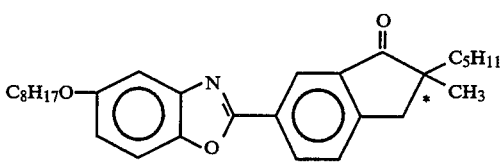 (205)
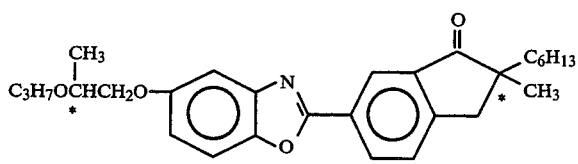 (206)
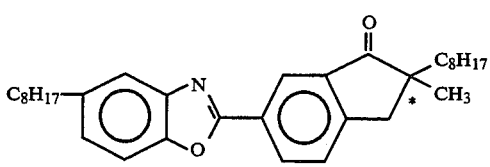 (207)
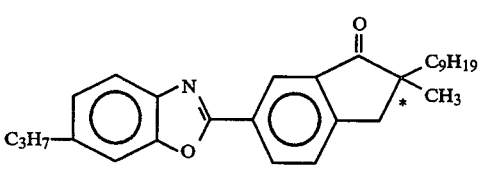 (208)
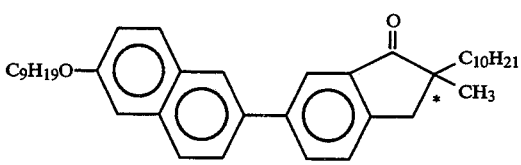 (209)
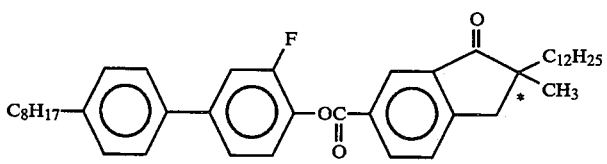 (210)
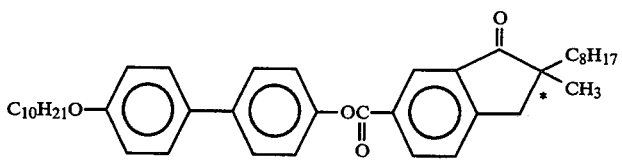 (211)

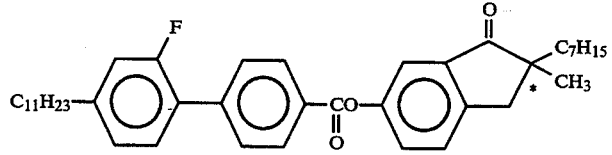 (212)
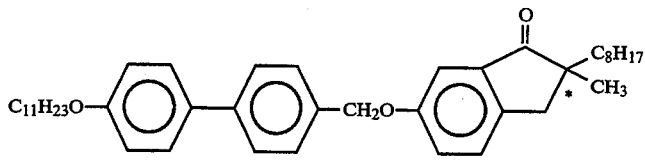 (213)
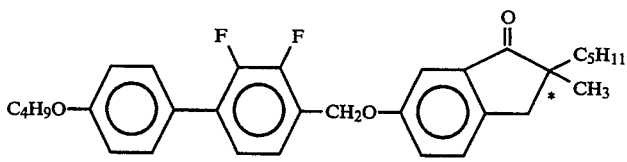 (214)
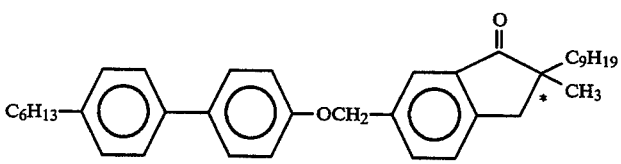 (215)
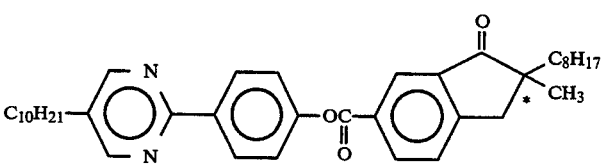 (216)
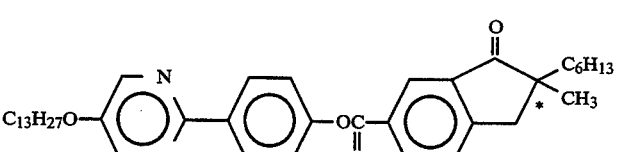 (217)
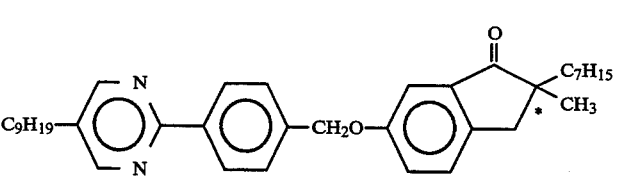 (218)
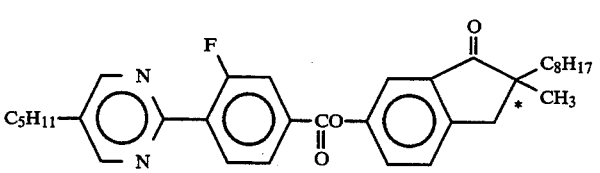 (219)
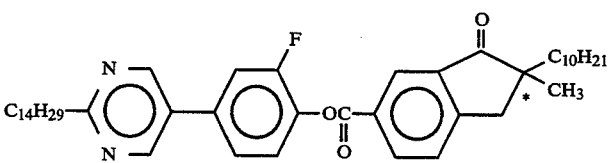 (220)
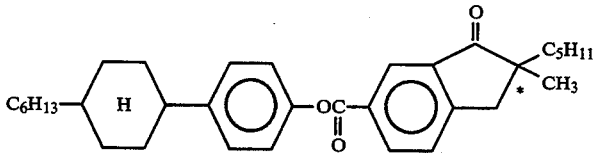 (221)

-continued
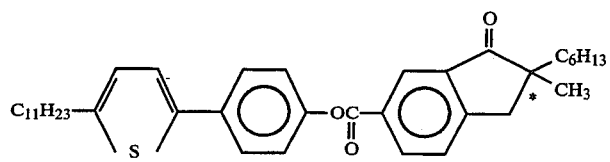 (222)
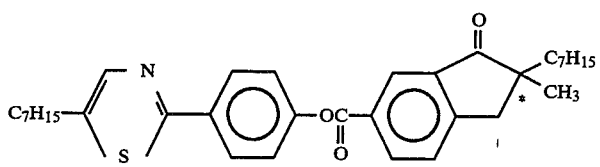 (223)
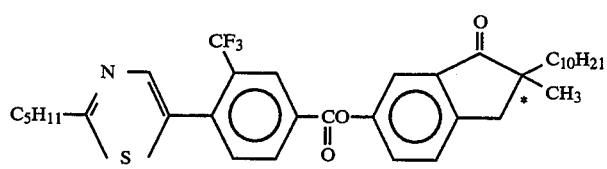 (224)
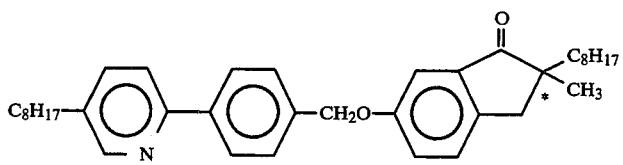 (225)
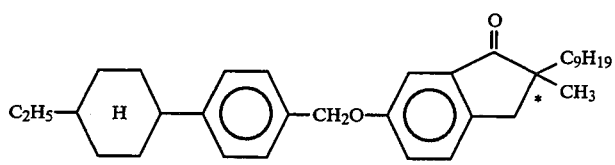 (226)
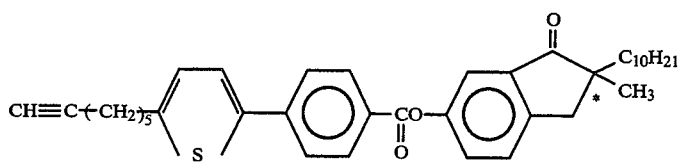 (227)
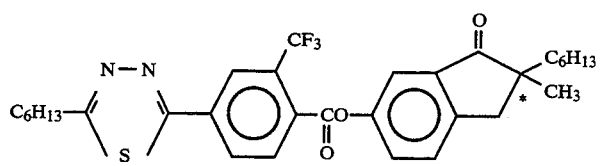 (228)
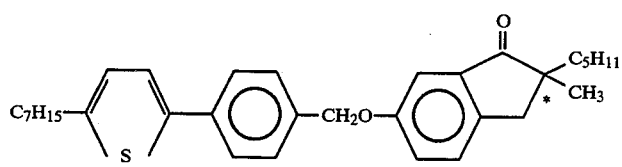 (229)
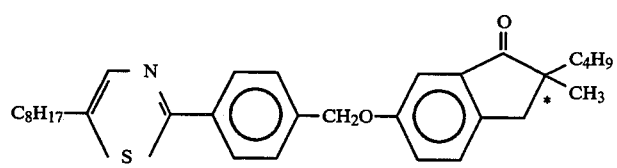 (230)

-continued
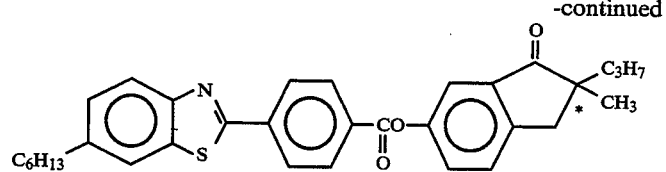 (231)
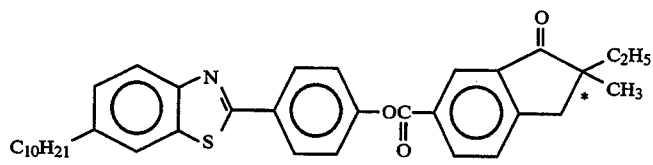 (232)
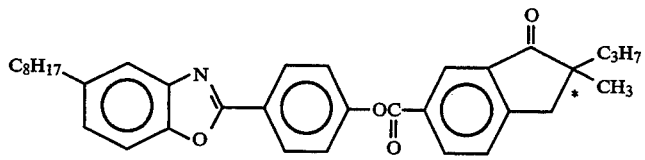 (233)
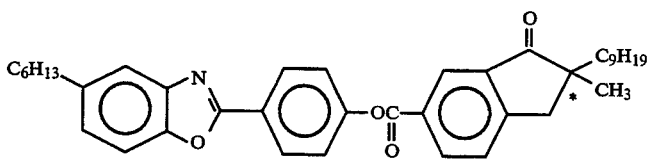 (234)
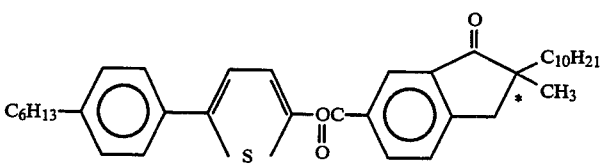 (235)
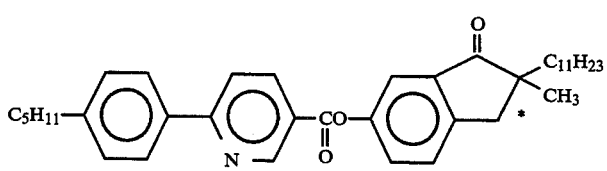 (236)
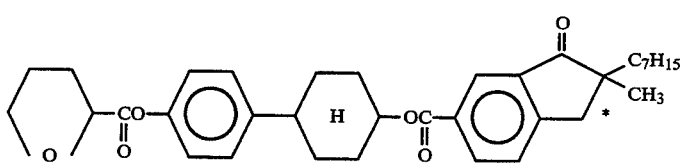 (237)
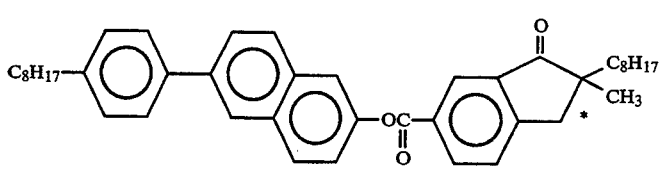 (238)
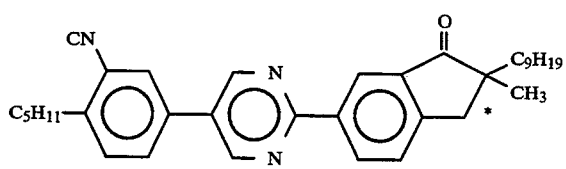 (239)
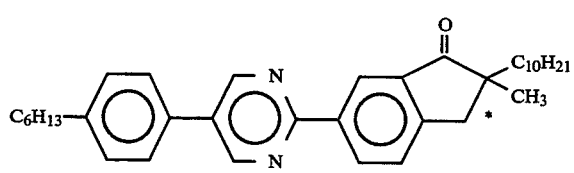 (240)

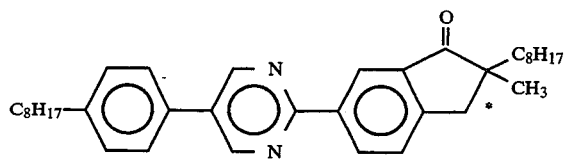
(241)
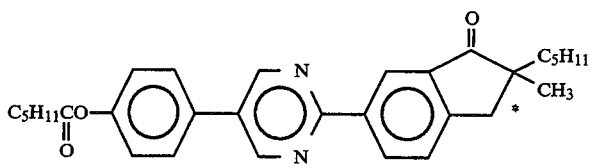
(242)
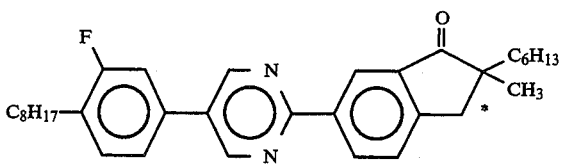
(243)
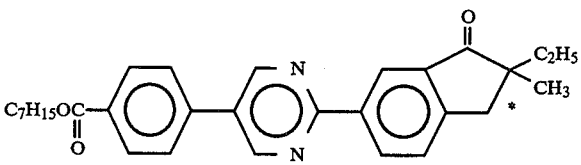
(244)
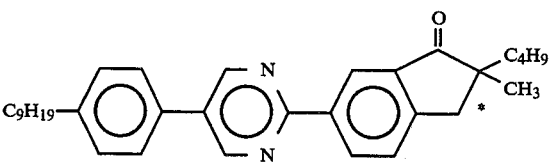
(245)
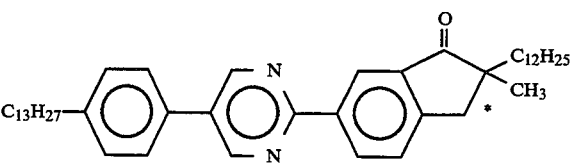
(246)
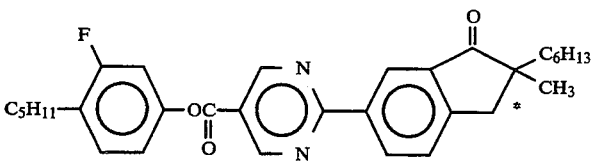
(247)
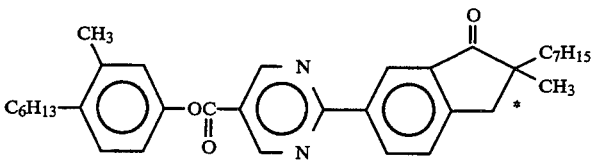
(248)
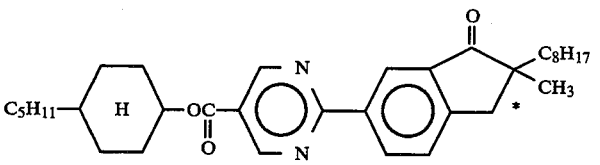
(249)

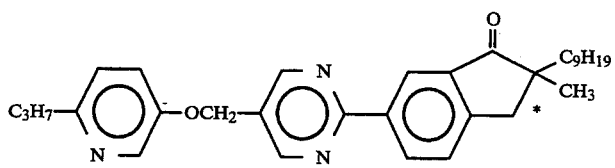
(250)
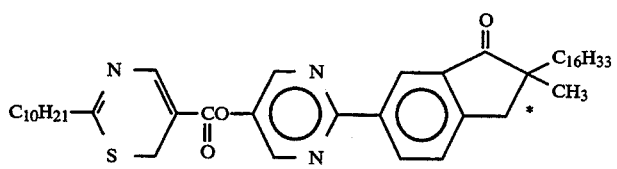
(251)
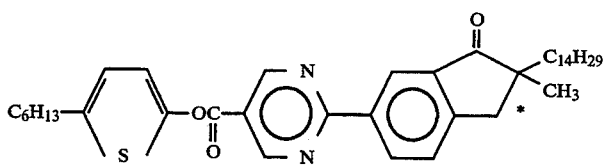
(252)
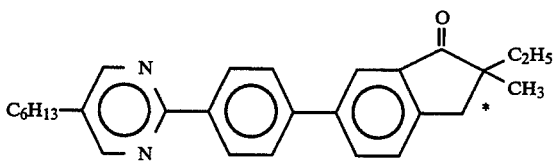
(253)
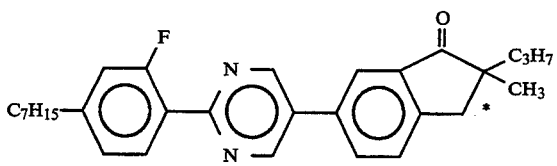
(254)
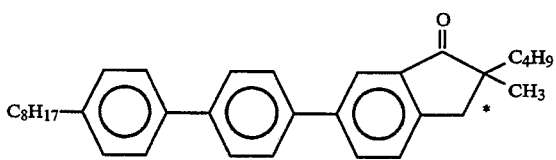
(255)
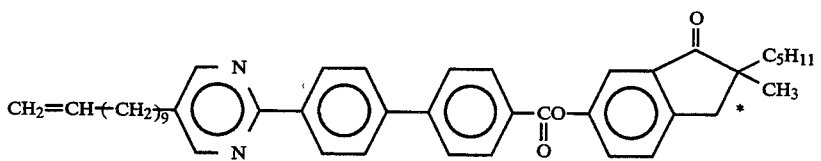
(256)
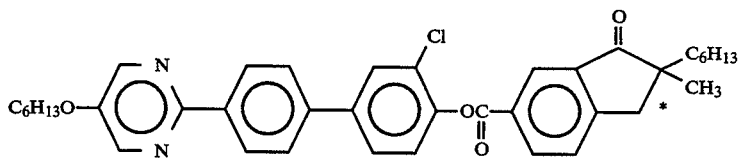
(257)
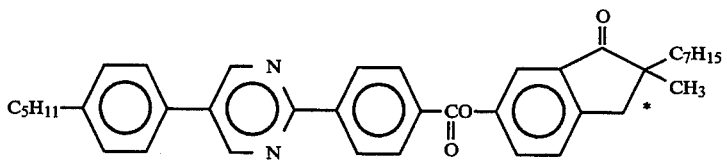
(258)

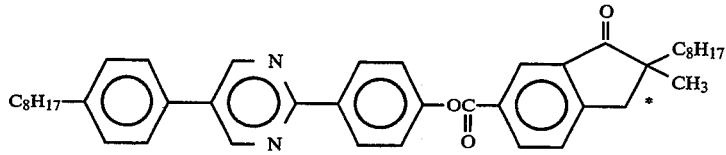 (259)
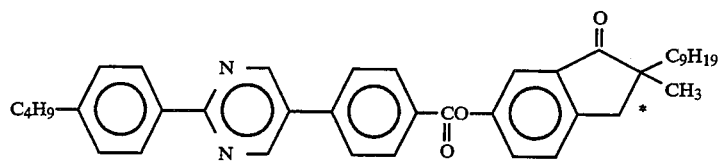 (260)
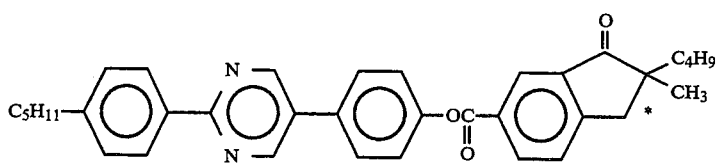 (261)
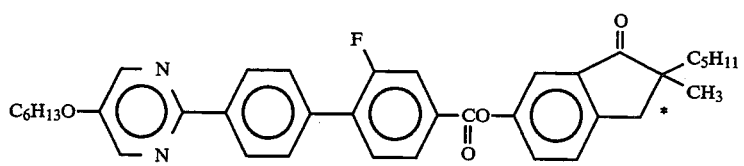 (262)
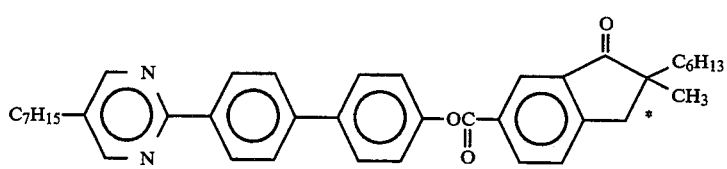 (263)
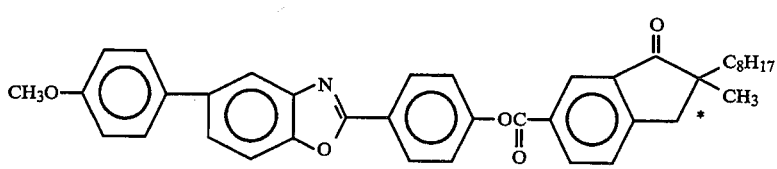 (264)
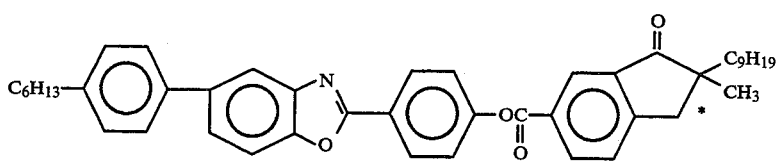 (265)
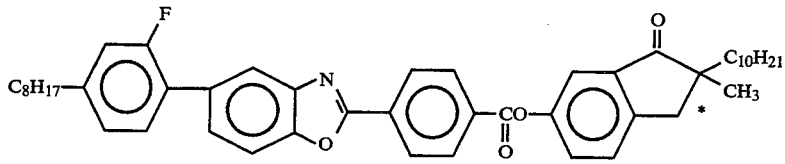 (266)
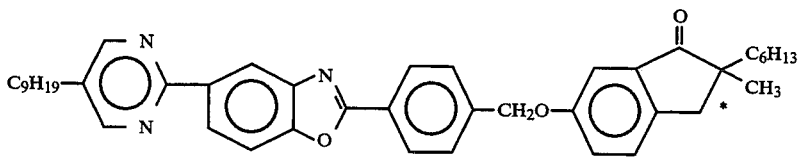 (267)
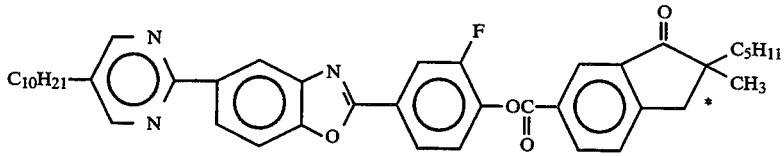 (268)

-continued
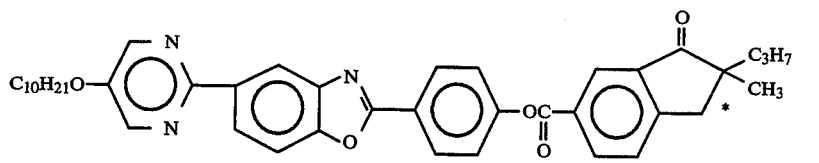
(269)
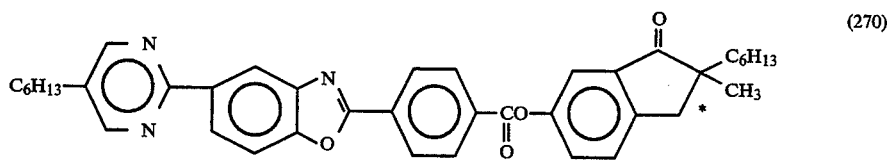
(270)
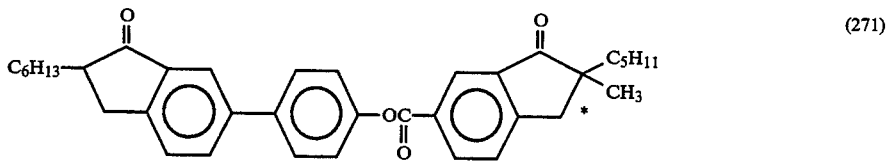
(271)
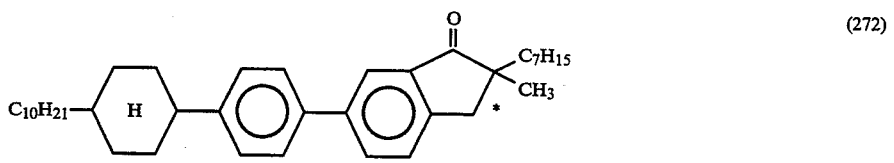
(272)
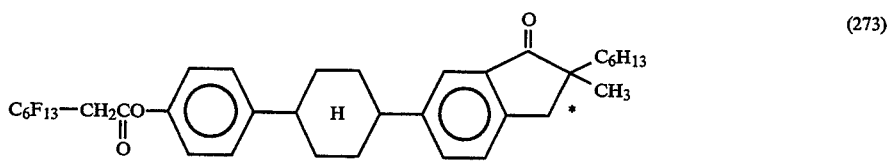
(273)
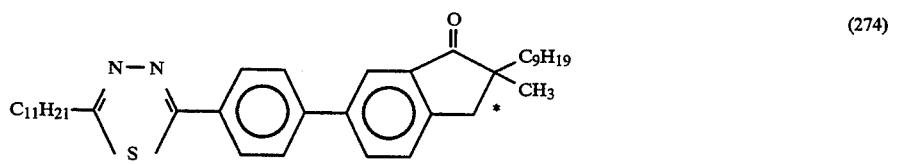
(274)
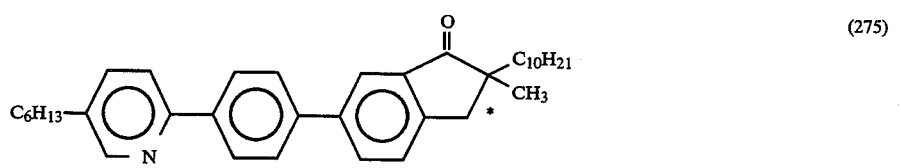
(275)
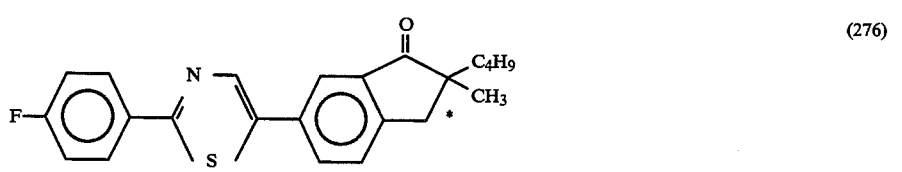
(276)
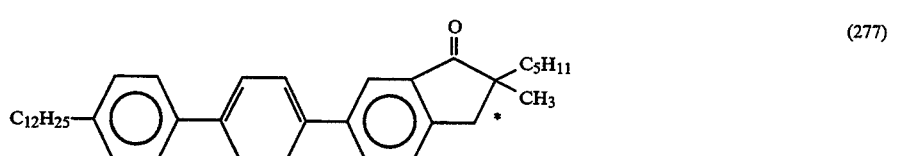
(277)

-continued
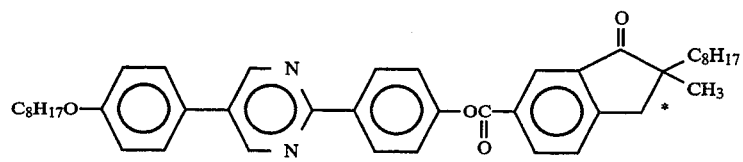 (278)
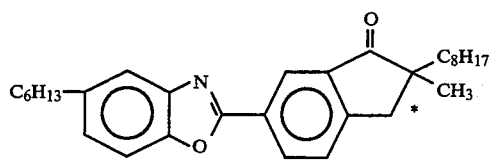 (279)
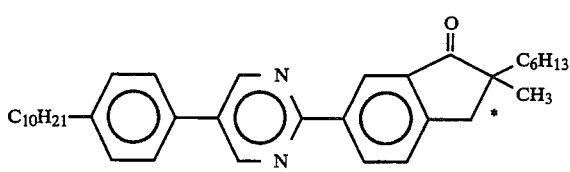 (280)
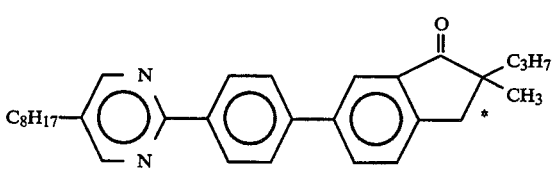 (281)
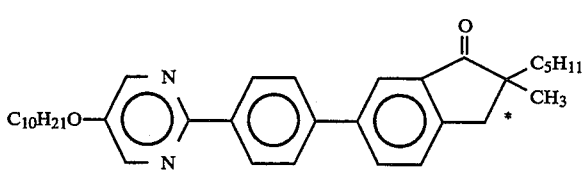 (282)
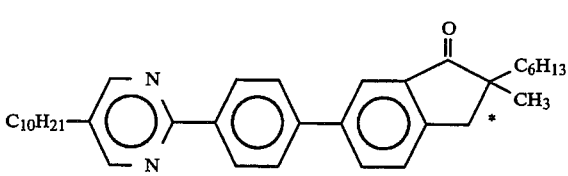 (283)
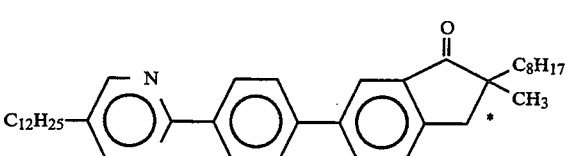 (284)
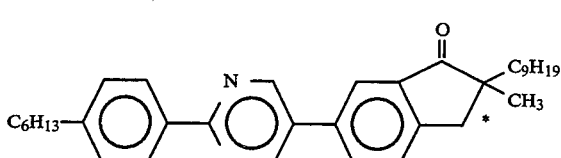 (285)
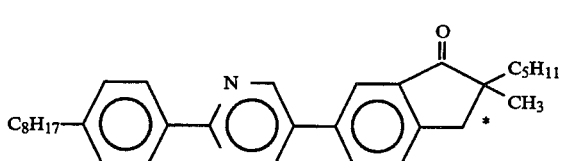 (286)

-continued
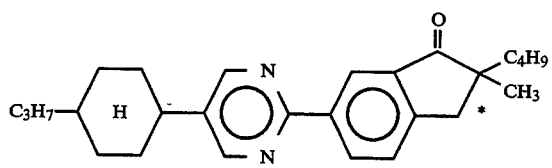 (287)
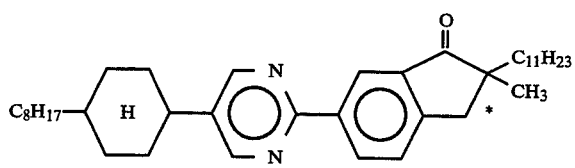 (288)
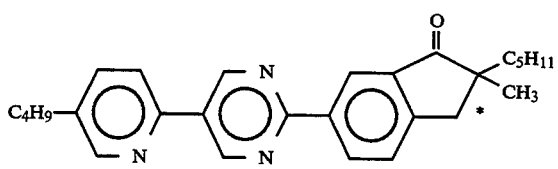 (289)
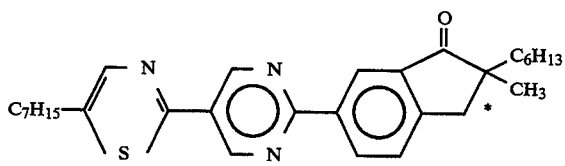 (290)
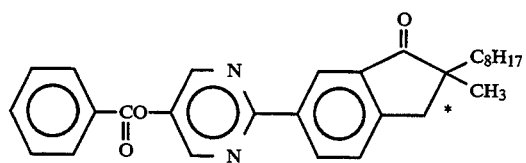 (291)
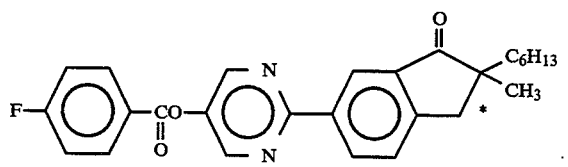 (292)
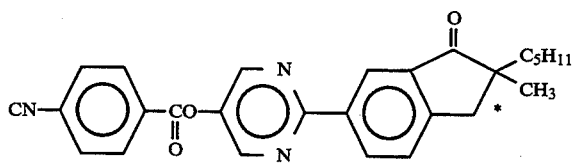 (293)
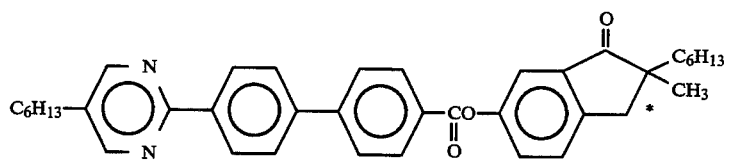 (294)
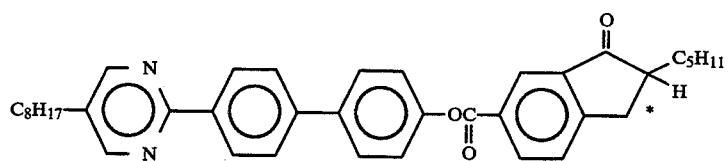 (295)

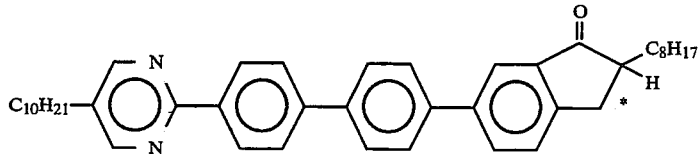 (296)

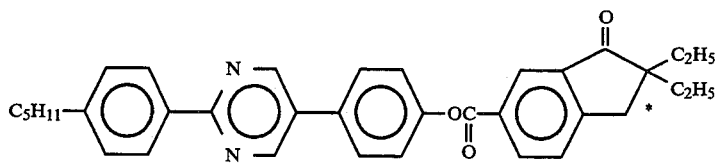 (297)

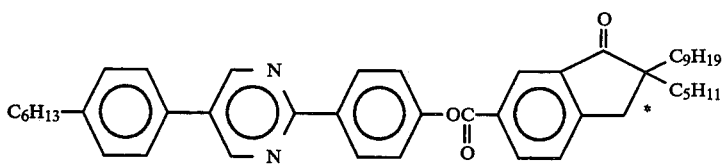 (298)

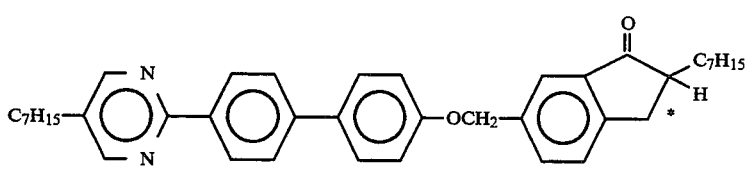 (299)

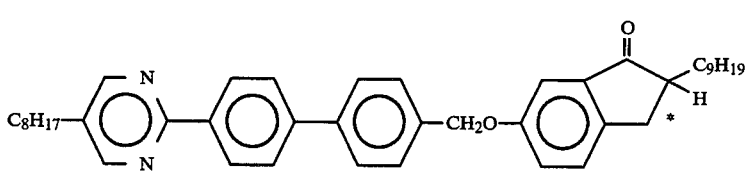 (300)

The liquid crystal composition according to the present invention may be obtained by mixing at least one species of the mesomorphic compound represented by the formula (I) and at least one species of another mesomorphic compound in appropriate proportions.

The liquid crystal composition according to the present invention may also be obtained by mixing at least one species of the optically active compound represented by the formula (II) and at least one species of another mesomorphic compound in appropriate proportions. In this instance, the liquid crystal composition may more preferably be obtained by mixing at least one species of the optically active compound represented by the formula (II), at least one species of another mesomorphic compound having an optically active group and at least one species of an optically inactive mesomorphic compound.

The liquid crystal composition according to the present invention may preferably be formulated as a liquid crystal composition capable of showing ferroelectricity, particularly a liquid crystal composition showing a chiral smectic phase.

Specific examples of another mesomorphic compound and/or optically inactive mesomorphic compound described above may include those denoted by the following formulas (III) to (XIII).

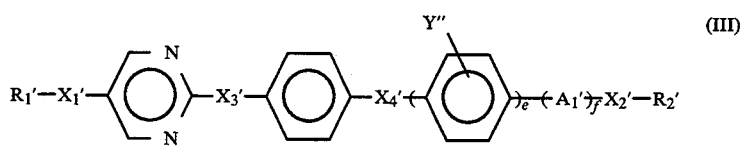 (III)

wherein e denotes 0 or 1 and f denotes 0 or 1 with proviso that $e+f=0$ or 1; Y''' denotes H, halogen, $CH_3$ or $CF_3$; $X_1'$ and $X_2'$ respectively denote a single bond,

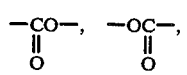

—O— or

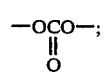

$X_3'$ and $X_4'$ respectively denote a single bond,

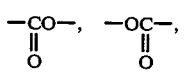

—OCH$_2$— or —CH$_2$O—; and $A_1'$ denotes

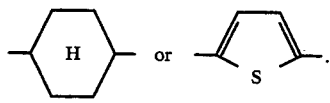 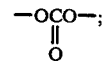

In the formula (III), preferred compounds thereof may include those represented by the following formulas (IIIa) to (IIIe):

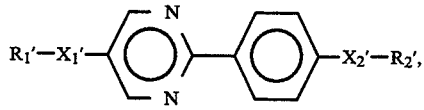 (IIIa)

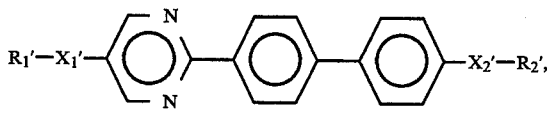 (IIIb)

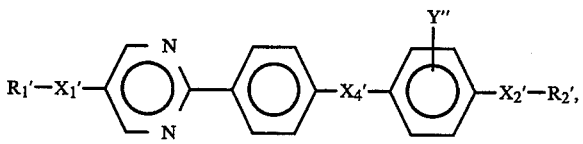 (IIIc)

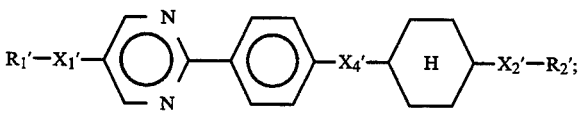 (IIId)

and

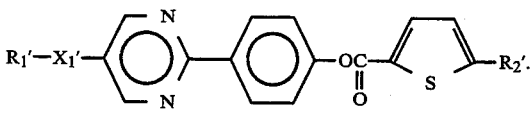 (IIIe)

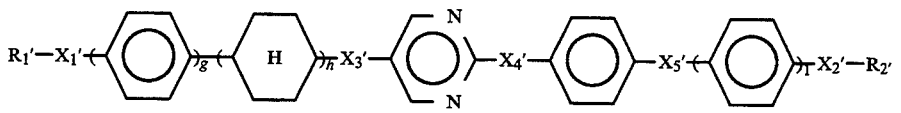 (IV)

wherein g and h respectively denote 0 or 1 with proviso that g+h=0 or 1: i denotes 0 or 1; $X_1'$ and $X_2'$ respectively denote a single bond,

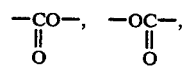

and $X_3'$, $X_4'$ and $X_5'$ respectively denote a single bond, —O— or

—OCO—;
 ||
 O

—CO—, —OC—,
 ||    ||
 O     O

—CH₂O— or —OCH₂—.

In the formula (IV), preferred compounds thereof may include those represented by the following formulas (IVa) to (IVc):

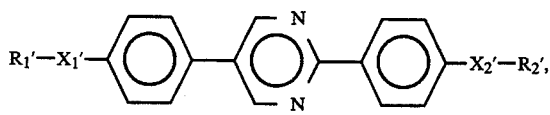 (IVa)

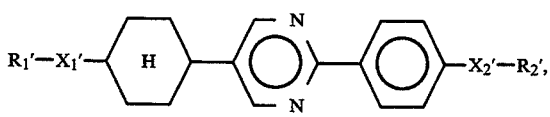 (IVb)

and

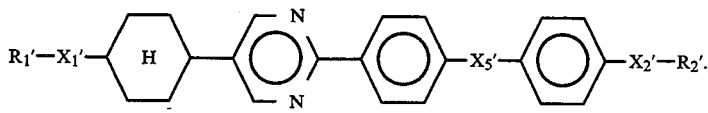 (IVc)

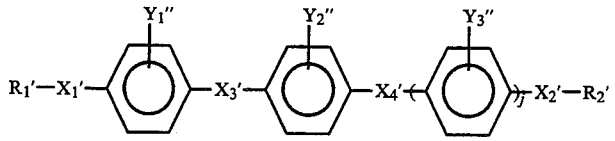 (V)

wherein j denotes 0 or 1; $Y_1''$, $Y_2''$ and $Y_3''$ respectively denote H, halogen, $CH_3$ or $CF_3$; $X_1'$ and $X_2'$ respectively denote a single bond,

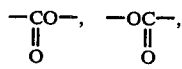

—O— and

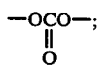

and $X_3'$ and $X_4'$ respectively denote a single bond,

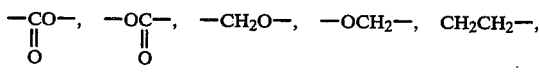

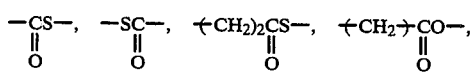

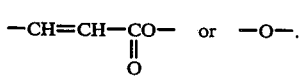

In the formula (V), preferred compounds thereof may include those represented by the following formulas (Va) and (Vb):

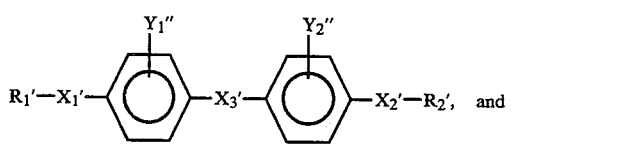 (Va), and

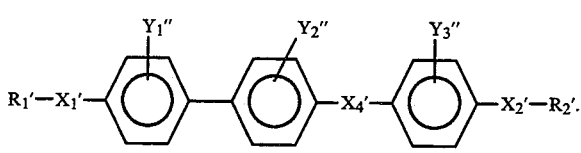 (Vb)

—O— or

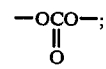

and $X_3'$ and $X_4'$ respectively denote a single bond,

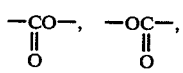

$—CH_2O—$ or $—OCH_2—$.

In the formula (VI), preferred compounds thereof may include those represented by the following formulas (VIa) to (VIf):

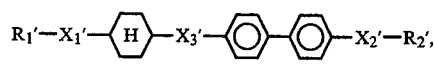 (VIa)

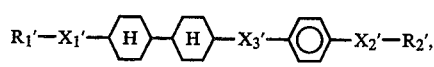 (VIb)

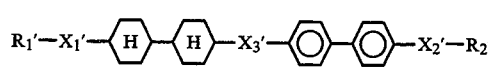 (VIc)

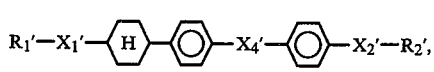 (VId)

(VI)

wherein k, l and m respectively denote 0 or 1 with proviso that k+l+m=0, 1 or 2; $X_1'$ and $X_2'$ respectively denote a single bond,

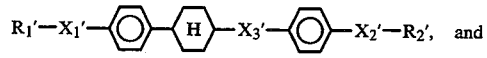 (VIe)

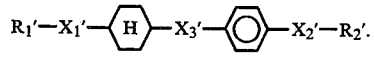 (VIf)

Herein, $R_1'$ and $R_2'$ respectively denote a linear or branched alkyl group having 1-18 carbon atoms capable of including one or non-neighboring two or more methylene groups which can be replaced with —CH halogen— and capable of further including one or two or more non-neighboring methylene groups other than those directly connected to $X_1'$ or $X_2'$ which can be replaced with at least one species of —O—,

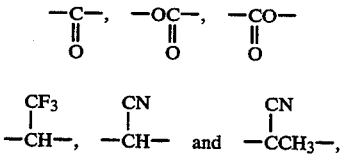

with proviso that $R_1'$ and $R_2'$ respectively do not connect to a ring structure by a single bond when $R_1'$ and $R_2'$ respectively denote a halogenated alkyl group containing one methylene group replaced with —CH halogen— or —CH(CF$_3$)—.

Further, preferred examples of $R_1'$ and $R_2'$ may respectively include those represented by the following groups (i) to (xi):

i) a linear alkyl group having 1-15 carbon atoms;

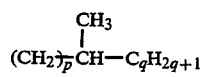

ii)

wherein p denotes an integer of 0-5 and q denotes an integer of 2-11 (optically active or inactive);

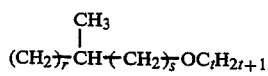

iii)

wherein r denotes an integer of 0-6, s denotes 0 or 1, and t denotes an integer of 1-14 (optically active or inactive);

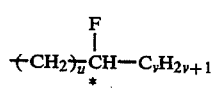

iv)

wherein u denotes 0 or 1 and v denotes an integer of 1-16;

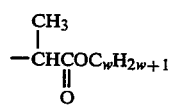

v)

wherein w denotes an integer of 1-15 (optically active or inactive);

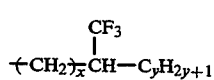

vi)

wherein x denotes an integer of 0-2 and y denotes an integer of 1-15.

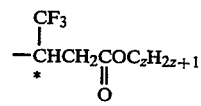

vii)

wherein z denotes an integer of 114 15.

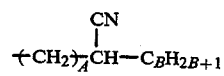

viii)

wherein A denotes an integer of 0-2 and B denotes an integer of 1-15 (optically active or inactive); and

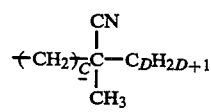

ix)

wherein C denotes an integer of 0-2 and D denotes an integer of 1-15 (optically active or inactive).

x) hydrogen (H), and
xi) fluorine (F).

In the above-mentioned formula (III), more preferred compounds thereof may include those represented by the formulas (IIIaa) to (IIIdc):

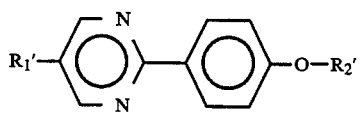

(IIIaa)

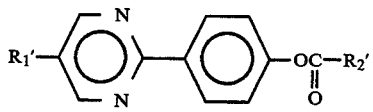

(IIIab)

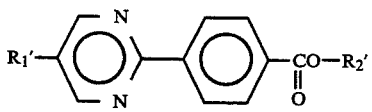

(IIIac)

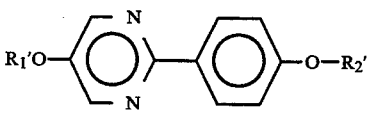

(IIIad)

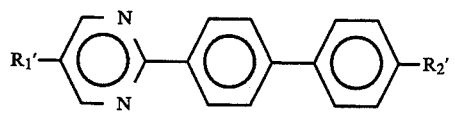

(IIIba)

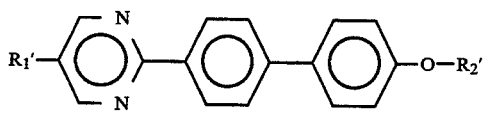

(IIIbb)

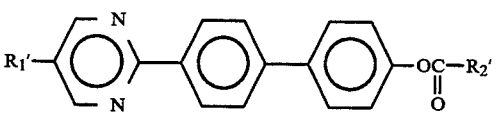

(IIIbc)

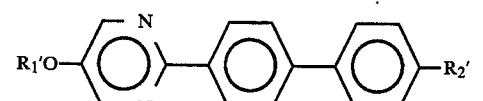

(IIIbd)

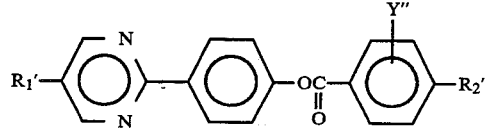
(IIIca)
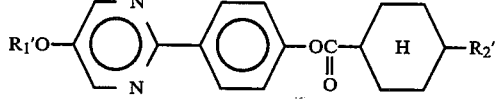
(IIIdc)
(IIIcb)
In the above-mentioned formula (IV), more preferred compounds thereof may include those represented by the formulas (IVaa) to (IVcd):
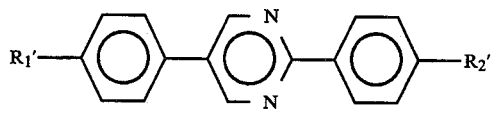
(IVaa)
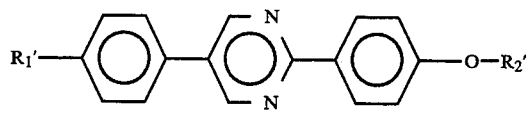
(IVab)
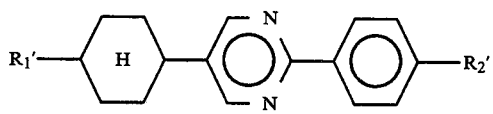
(IVba)
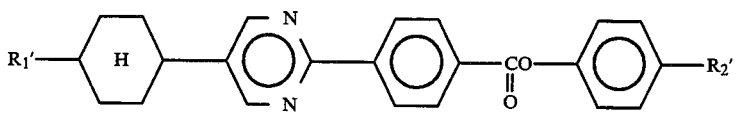
(IVca)
and
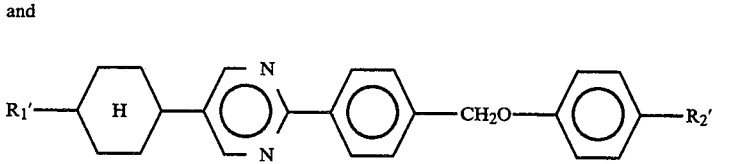
(IVcb)
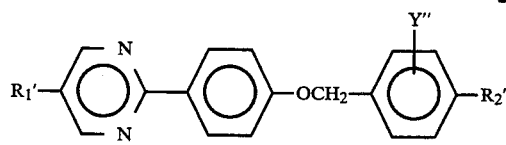
(IIIcc)
In the above-mentioned formula (V), more preferred compounds thereof may include those represented by the formulas (Vaa) to (Vbf):
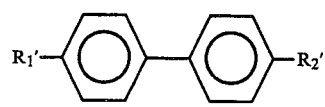
(Vaa)
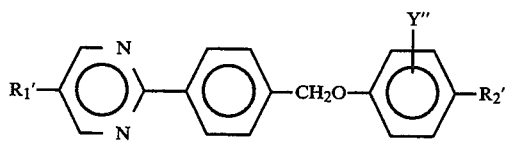
(IIIcd)
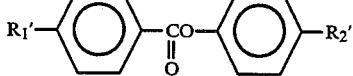
(Vab)
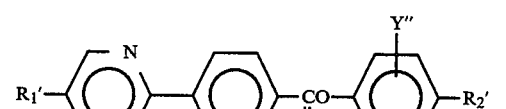
(IIIda)
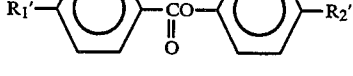
(Vac)
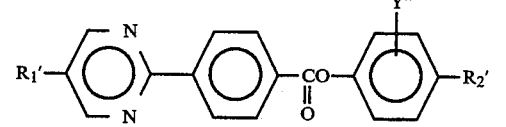
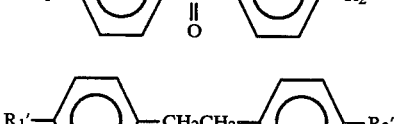
(Vad)
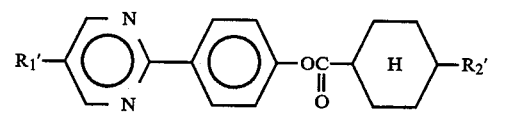
(IIIdb)
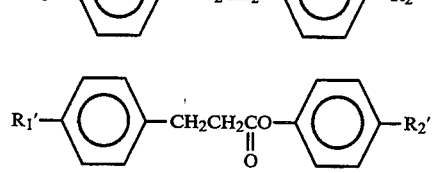
(Vae)
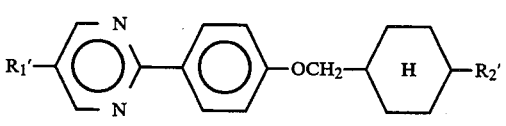
and

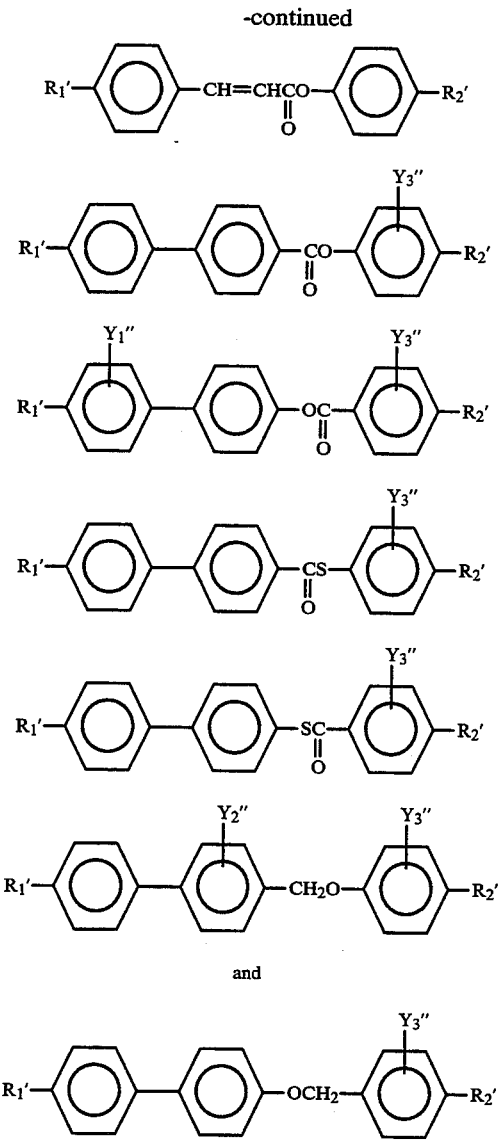

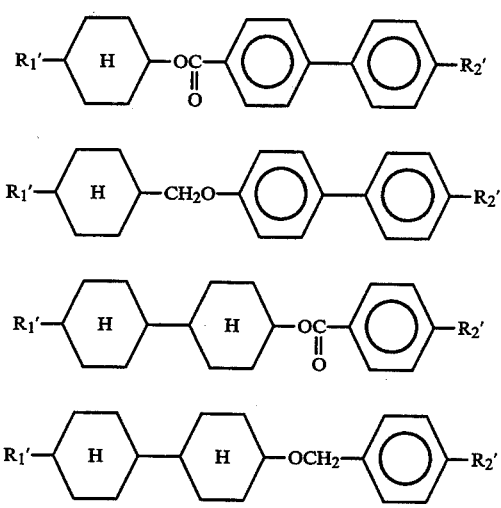

In the above-mentioned formula (VI), more preferred compounds thereof may include those represented by the formulas (VIaa) to (VIfa):

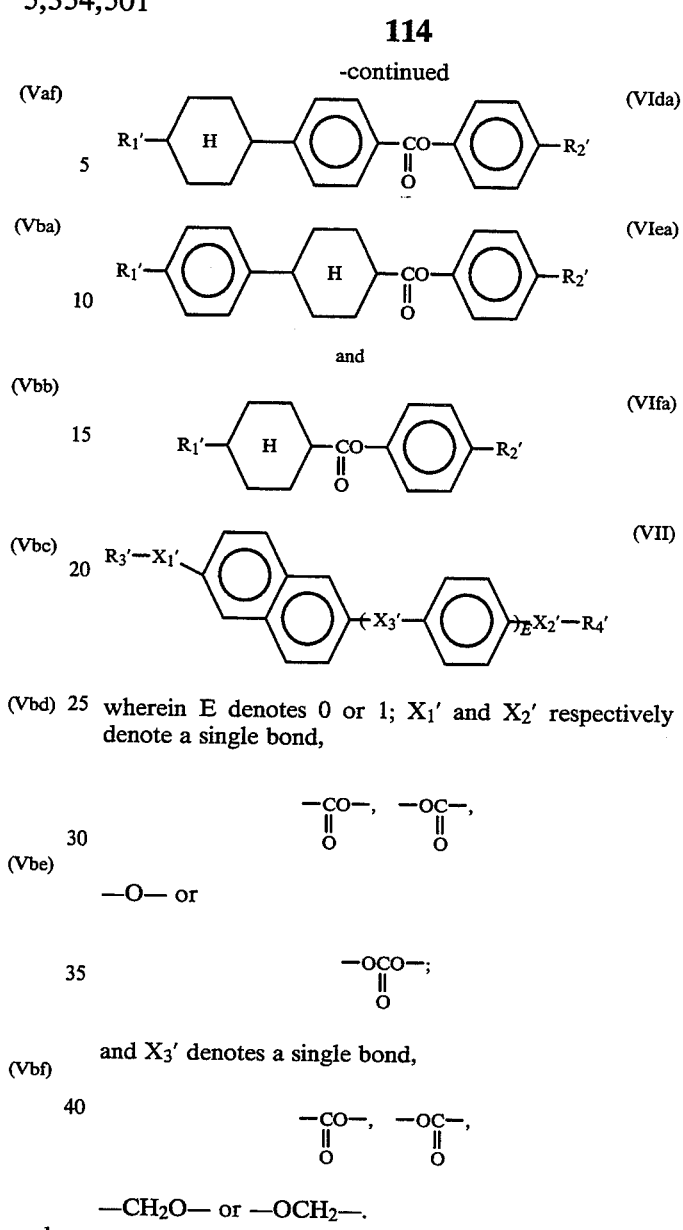

wherein E denotes 0 or 1; $X_1'$ and $X_2'$ respectively denote a single bond, $$-\underset{\underset{O}{\|}}{C}O-, \quad -O\underset{\underset{O}{\|}}{C}-,$$

—O— or $$-O\underset{\underset{O}{\|}}{C}O-;$$

and $X_3'$ denotes a single bond, $$-\underset{\underset{O}{\|}}{C}O-, \quad -O\underset{\underset{O}{\|}}{C}-,$$

—CH$_2$O— or —OCH$_2$—.

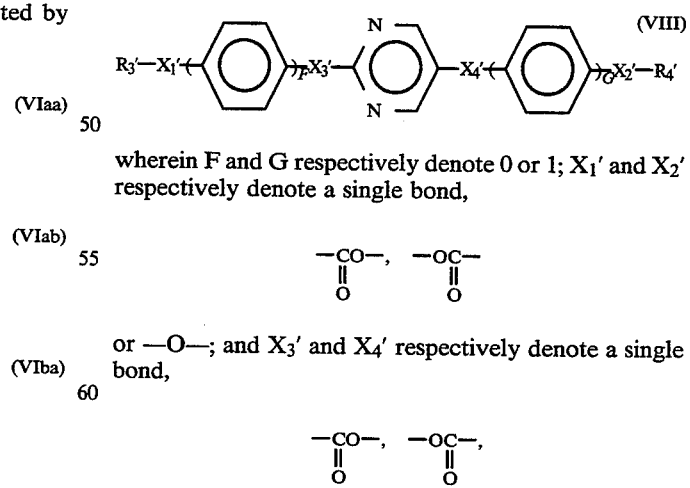

wherein F and G respectively denote 0 or 1; $X_1'$ and $X_2'$ respectively denote a single bond, $$-\underset{\underset{O}{\|}}{C}O-, \quad -O\underset{\underset{O}{\|}}{C}-$$

or —O—; and $X_3'$ and $X_4'$ respectively denote a single bond, $$-\underset{\underset{O}{\|}}{C}O-, \quad -O\underset{\underset{O}{\|}}{C}-,$$

—CH$_2$O— or —OCH$_2$—.

In the above formula (VII), preferred compounds thereof may include those represented by the following formulas (VIIa) and (VIIb):

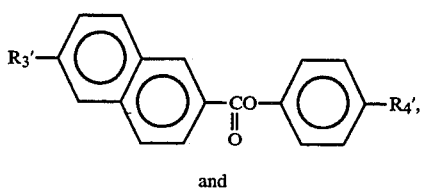
(VIIa)

and

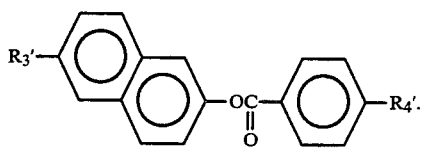
(VIIb)

In the above formula (VIII), preferred compounds thereof may include those represented by the follwoing formulas (VIIIa) and (VIIIb).

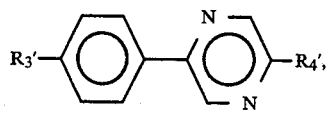
(VIIIa)

and

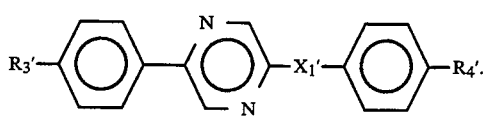
(VIIIb)

More preferred compounds of the formula (VIIIb) may include those represented by the formulas (VIIIba) to (VIIIbb):

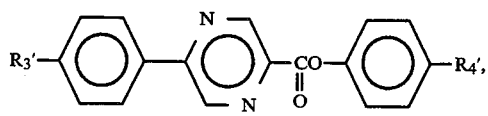
(VIIIba)

and

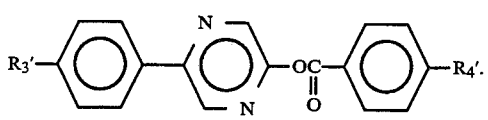
(VIIIbb)

Herein, $R_3'$ and $R_4'$ respectively denote a linear or branched alkyl group having 1-18 carbon atoms capable of including one or non-neighboring two or more methylene groups which can be replaced with —CH halogen— and capable of further including one or two or more non-neighboring methylene groups other than those directly connected to $X_1'$ or $X_2'$ which can be replaced with at least one species of —O—,

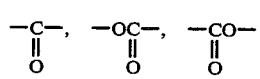

-continued
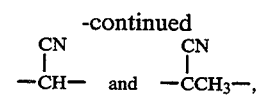

with proviso that $R_3'$ and $R_4'$ respectively do not connect to a ring structure by a single bond when $R_3'$ and $R_4'$ respectively denote a halogenated alkyl group containing one methylene group replaced with —CH halogen—.

Further, preferred examples of $R_3'$ and $R_4'$ may respectively include those represented by the following groups (i) to (vii):

i) a linear alkyl group having 1-15 carbon atoms;

$$\overset{\text{ii)}}{(CH_2)_{\overline{p}}CH\!-\!C_qH_{2q+1}}$$
$$\phantom{xxxxxxx}\overset{|}{CH_3}$$

wherein p denotes an integer of 0-5 and q denotes an integer of 2-11 (optically active or inactive);

$$\overset{\text{iii)}}{(CH_2)_{\overline{r}}CH\!\!-\!\!(CH_2)_{\overline{s}}OC_tH_{2t+1}}$$
$$\phantom{xxxxxxx}\overset{|}{CH_3}$$

wherein r denotes an integer of 0-6, s denotes 0 or 1, and t denotes an integer of 1-14 (optically active or inactive);

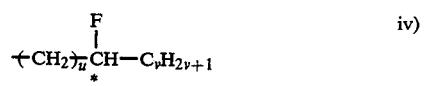

wherein u denotes an integer of 0 or 1 and v denotes an integer of 1-16;

wherein w denotes an integer of 1-15 (optically active or inactive);

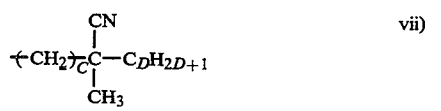

wherein A denotes an integer of 0-2 and B denotes an integer of 1-15 (optically active or inactive); and $$\overset{\text{vii)}}{+CH_2)_{\overline{C}}C\!\!-\!\!C_DH_{2D+1}}$$
$$\phantom{xxxxx}\overset{|}{CH_3}$$

wherein C denotes an integer of 0-2 and D denotes an integer of 1-15 (optically active or inactive).

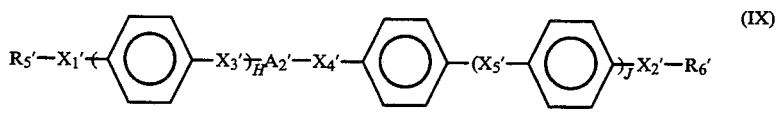
(IX)

wherein H and J respectively denote 0 or 1 with proviso that H+J=0 or 1; $X_1'$ and $X_2'$ respectively denote a single bond, $-CO-$, $-OC-$ (with =O), or $-O-$; $A_2'$ denotes

[structure: phenyl with N-N]

[structure: pyridyl]

or

[structure: pyridyl];

and $X_3'$ and $X_4'$ respectively denote a single bond, $-CO-$, $-OC-$ (with =O), $-CH_2O-$ or $-OCH_2-$.

$$R_5'-X_1'-A_3'-X_3'-\text{[phenyl]}-X_4'-\text{[H]}-X_2'-R_6' \quad (X)$$

wherein $X_1'$ and $X_2'$ respectively denote a single bond, $-CO-$, $-OC-$ (with =O)

or $-O-$; $A_3'$ denotes

[structure: pyridyl] or [structure: pyridyl];

and $X_3'$ and $X_4'$ respectively denote a single bond, $-CO-$, $-OC-$ (with =O), $-CH_2O-$ or $-OCH_2-$.

$$R_5'-X_1'-A_4'-X_3'-\text{[phenyl]}-\text{[pyrimidinyl N,N]}-X_2'-R_6' \quad (XI)$$

wherein $X_1'$ and $X_2'$ respectively denote a single bond, $-CO-$, $-OC-$ (with =O)

or $-O-$; $A_4'$ denotes

[structure: pyridyl] or [structure: pyridyl];

and $X_3'$ respectively denotes a single bond, $-CO-$, $-OC-$ (with =O), $-CH_2O-$ or $-OCH_2-$.

$$\text{(XII)}$$
[complex structure with $Y_4'$, $N-Z_1'$, $S$, $Y_5'$, $Y_6'$, K, L, M, H, and substituents $R_5'$, $R_6'$, $X_3'$, $X_1'$]

wherein K, L and M respectively denote 0 or 1 with the proviso that K+L+M=0 or 1; $X_1'$ denotes a single bond, $-CO-$, $-OC-$ (with =O)

or $-O-$; $X_3'$ denotes a single bond, $-CO-$, $-OC-$ (with =O), $-CH_2O-$ or $-OCH_2-$; $Y_4'$, $Y_5'$ and $Y_6'$ respectively denote H or F; and $Z_1'$ is CH or N.

$$R_5'-\text{[benzoxazole with }Z_2'\text{]}-A_5'-X_1'-R_6' \quad (XIII)$$

wherein $Z_2'$ denotes —— or $-S-$; and $A_5'$ denotes

[structure: phenyl] or [structure: naphthyl];

$X_1'$ denotes a single bond,

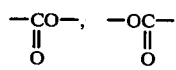

or —O—.

In the above formula (IX), preferred compounds thereof may include those represented by the following formulas (IXa) to (IXc):

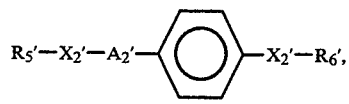
(IXa)

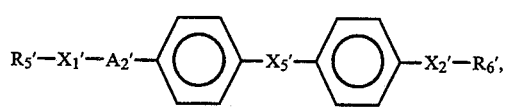
(IXb)

and

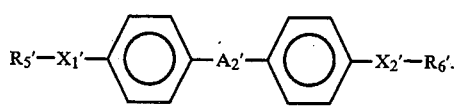
(IXc)

In the above formula (X), preferred compounds thereof may include those represented by the following formulas (Xa) and (Xb):

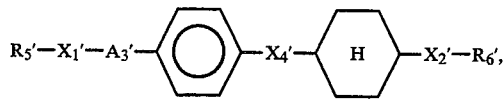
(Xa)

and

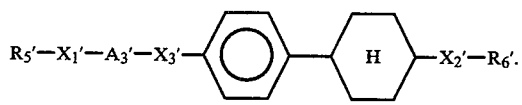
(Xb)

In the above formula (XII), preferred compounds thereof may include those represented by the following formulas (XIIa) and (XIIf):

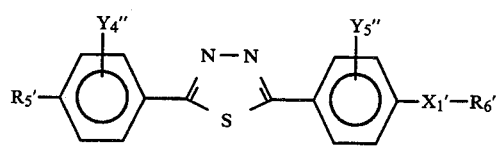
(XIIa)

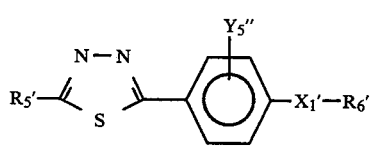
(XIIb)

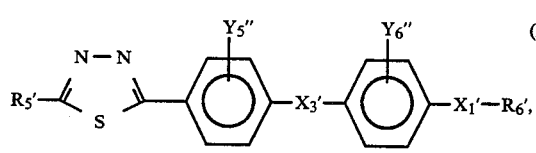
(XIIc)

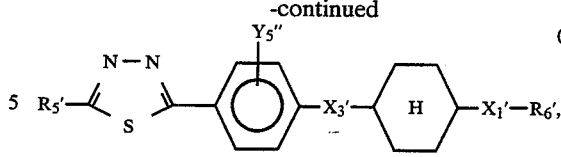
(XIId)

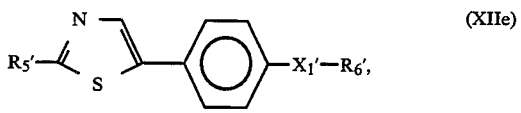
(XIIe)

and

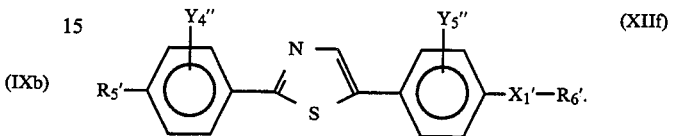
(XIIf)

In the above formula (XIII), preferred compounds thereof may include those represented by the following formulas (XIIIa) to (XIIIe):

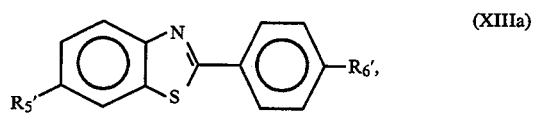
(XIIIa)

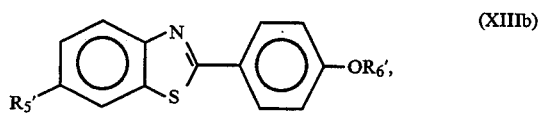
(XIIIb)

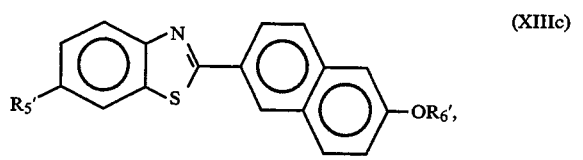
(XIIIc)

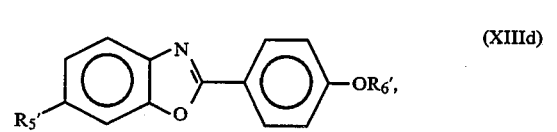
(XIIId)

and

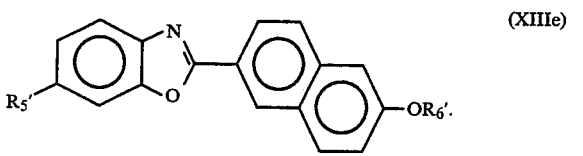
(XIIIe)

In the above-mentioned formula (IX), more preferred compounds thereof may include those represented by the formulas (IXaa) to (IXcc):

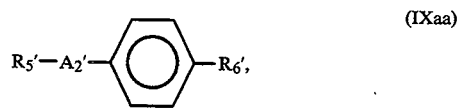
(IXaa)

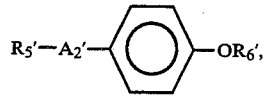
(IXab)

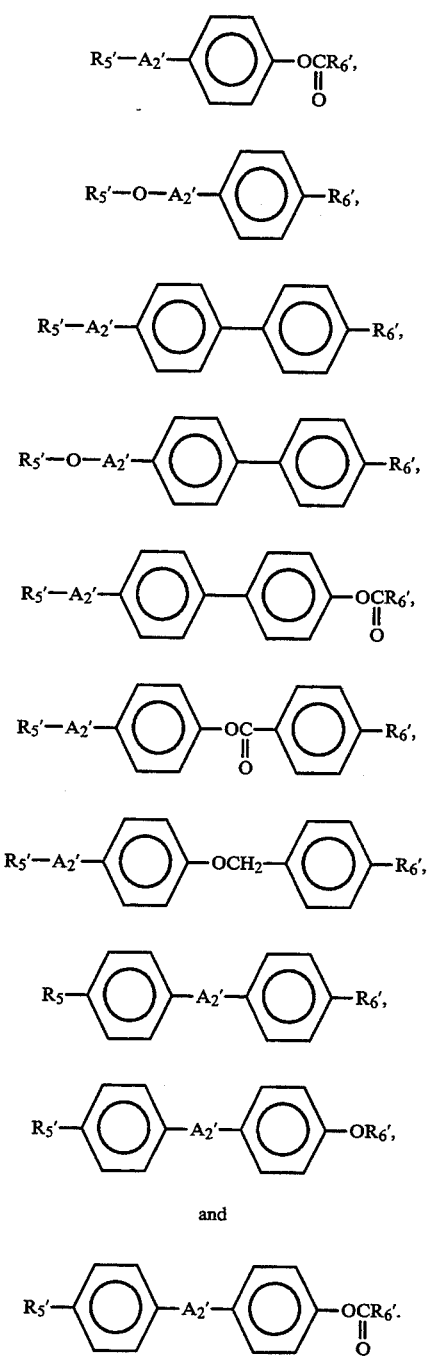

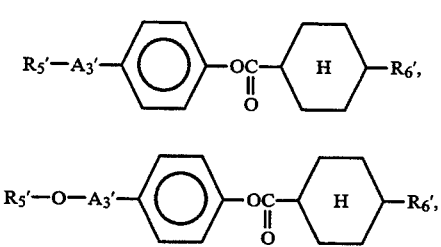

In the above-mentioned formula (X), more preferred compounds thereof may include those represented by the formulas (Xaa) to (Xbb):

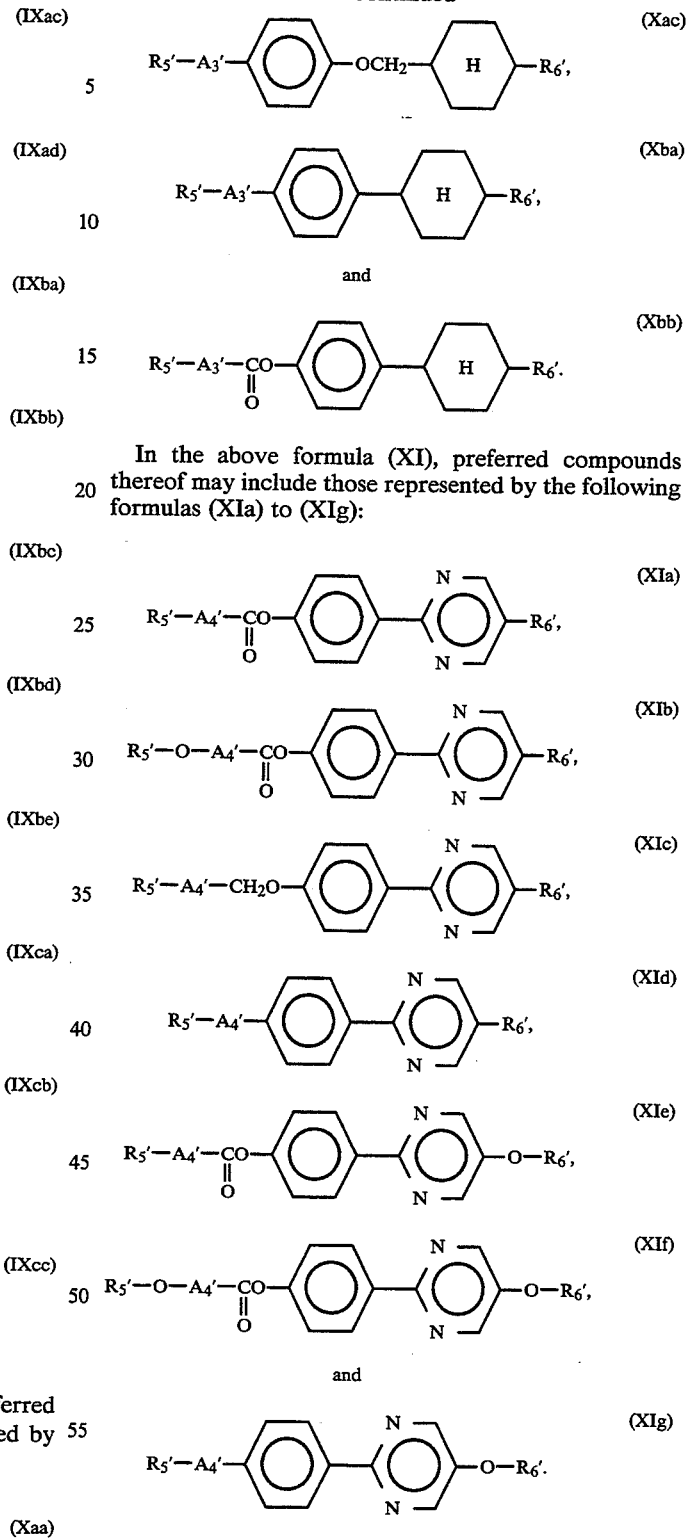

In the above formula (XI), preferred compounds thereof may include those represented by the following formulas (XIa) to (XIg):

In the above-mentioned formula (XII), more preferred compounds thereof may include those represented by the formula (XIIaa) to (XIIdb):

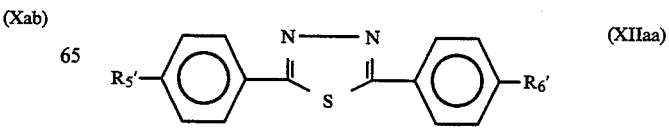

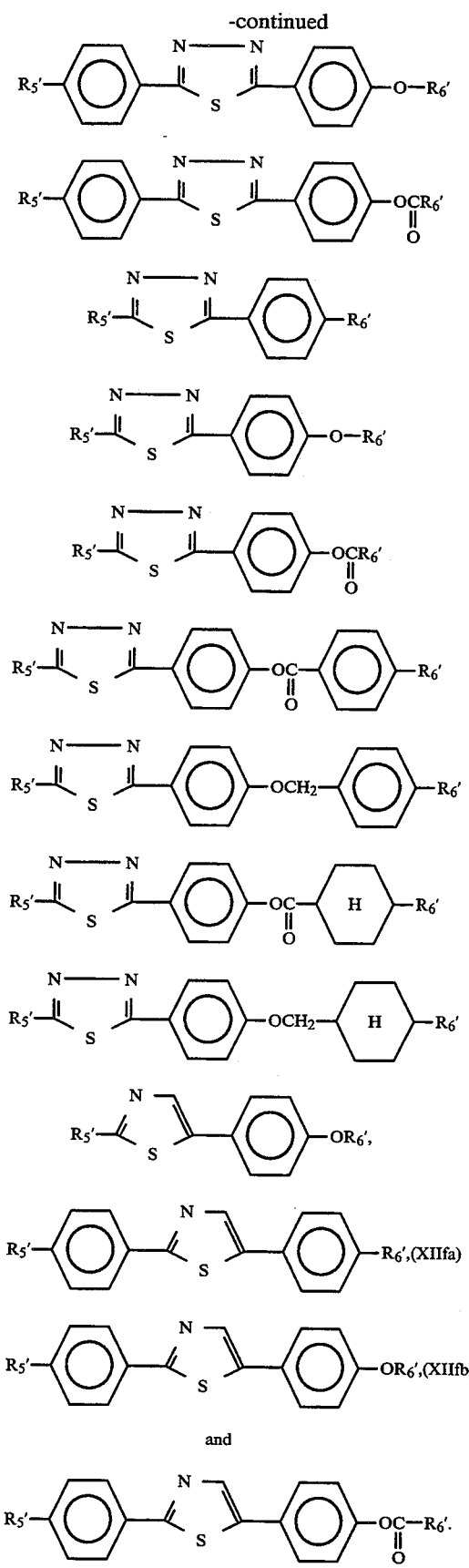

methylene groups other than those directly connected to $X_1'$ or $X_2'$ which can be replaced with at least one species of —O—,

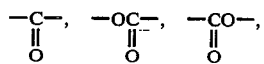

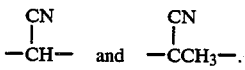

Further, preferred examples of $R_5'$ and $R_6'$ may respectively include those represented by the following groups (i) to (vi):

i) a linear alkyl group having 1–15 carbon atoms;

ii)
$$(CH_2)_{\overline{p}}CH-C_qH_{2q+1} \atop |\ CH_3}$$

wherein p denotes an integer of 0–5 and q denotes an integer of 2–11 (optically active or inactive);

iii)
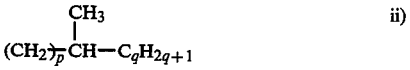

wherein r denotes an integer of 0–6, s denotes 0 or 1, and t denotes an integer of 1–14 (optically active or inactive);

iv)
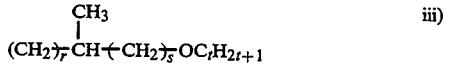

wherein w denotes an integer of 1–15 (optically active or inactive);

v)
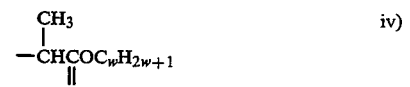

wherein A denotes an integer of 0–2 and B denotes an integer of 1–15 (optically active or inactive); and vi)
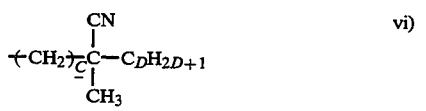

wherein C denotes an integer of 0–2 and D denotes an integer of 1–15 (optically active or inactive).

In formulating the liquid crystal composition according to the present invention, the liquid crystal composition may desirably contain 1–80 wt. %, preferably 1–60 wt. %, more preferably 1–40 wt. % of a mesomorphic compound represented by the formula Further, when two or more species of the mesomorphic compounds represented by the formula (I) are used, the liquid crystal composition may desirably contain 1–80 wt. %, preferably 1–60 wt. %, more preferably 1–40 wt. %, of the two or more species of the mesomorphic compounds represented by the formula (I).

In formulating the liquid crystal composition according to the present invention, the liquid crystal composition may desirably contain 0.1–60 wt. %, preferably 0.1–40 wt. %, more preferably 0.1–20 wt. % of an optically active compound represented by the formula (II).

Further, when two or more species of the optically active compounds represented by the formula (II) are used, the liquid crystal composition may desirably contain 0.1–60 wt. %, preferably 0.1–40 wt. %, more preferably 0.1–20 wt. %, of the two or more species of the optically active compounds represented by the formula (II).

In formulating the liquid crystal composition according to the present invention, the liquid crystal composition may desirably contain 0.1–40 wt. %, preferably 0.1–20 wt. %, more preferably 0.1–10 wt. % of an optically active compound represented by the formula (II), an appropriate amount of another mesomorphic compound having an optically active group and an appropriate amount of an optically inactive mesomorphic compound.

Further, when two or more species of the optically active compounds represented by the formula (II) are used, the liquid crystal composition may desirably contain 0.1–40 wt. %, preferably 0.1–20 wt. %, more preferably 0.1–10 wt. %, of the two or more species of the optically active compounds represented by the formula (II), and an appropriate amount of another mesomorphic compound having an optically active group and an appropriate amount of an optically inactive mesomorphic compound.

The liquid crystal device according to the present invention may preferably be prepared by heating the liquid crystal composition assuming a chiral smectic phase prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 10Å–1 micron, preferably 10–3000 Å, further preferably 10–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 μm, preferably 1 to 5 μm.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
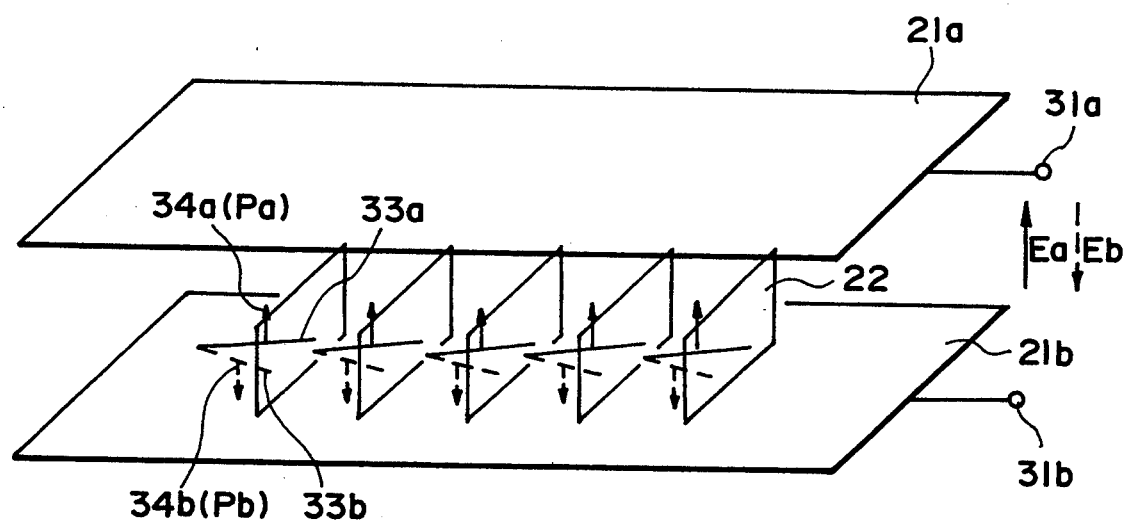

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
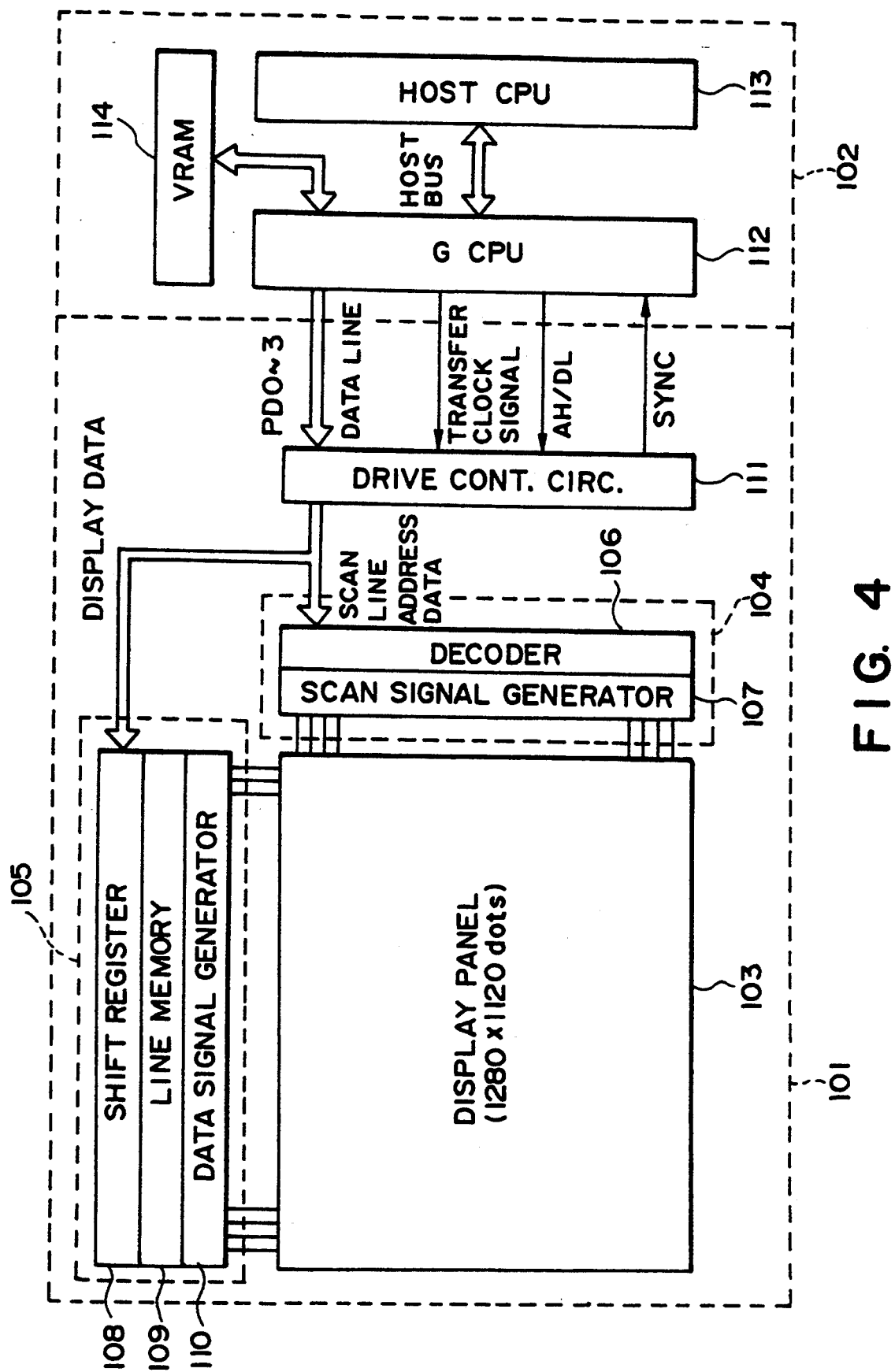
FIG. 4 is a block diagram showing a display apparatus comprising a liquid crystal device utilizing ferroelectricity of a liquid crystal composition and a graphic controller.
Figure 5:
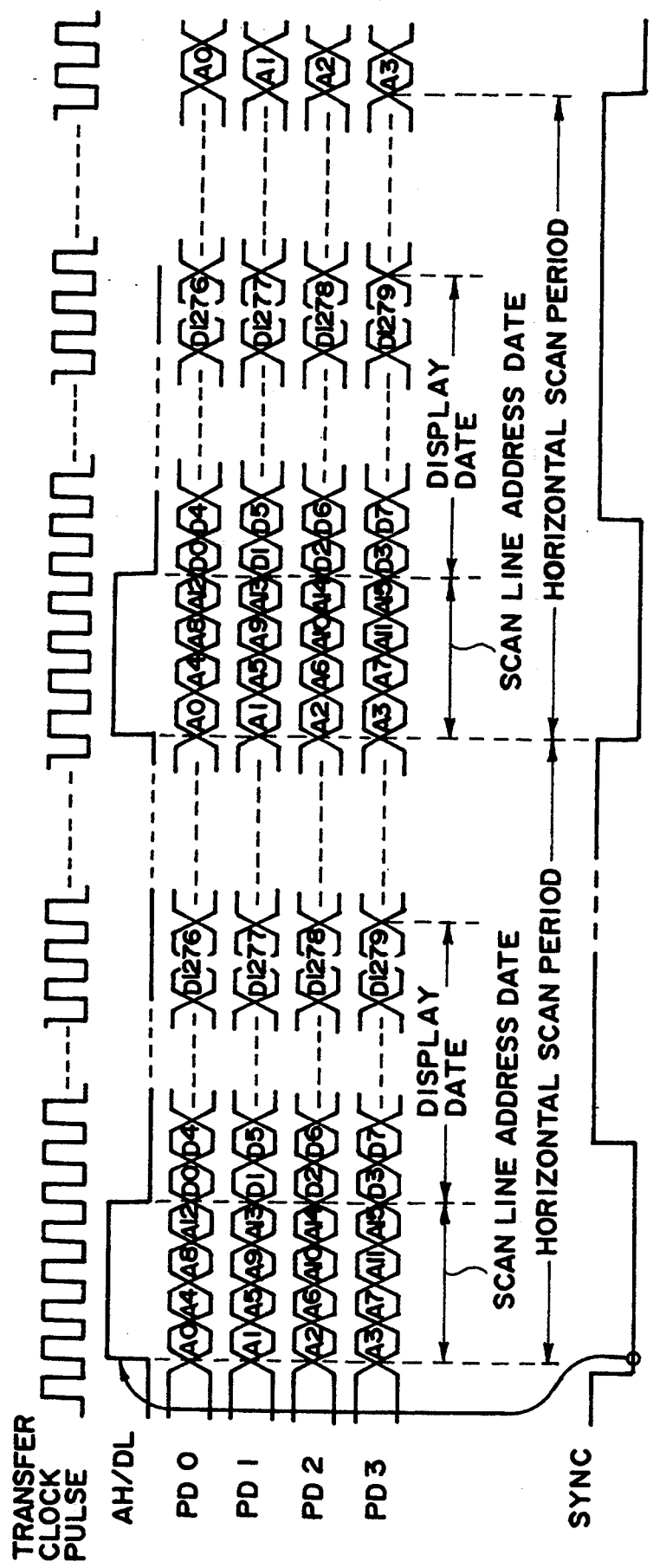
FIG. 5 is a time chart of image data communication showing time correlation between signal transfer and driving with respect to a liquid crystal display apparatus and a graphic controller.

Based on an arrangement appearing hereinbelow and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means shown in FIGS. 4 and 5. The graphic controller 102 principally comprises a CPU (central processing unit, herein referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

Hereinbelow, the present invention will be explained more specifically with reference to examples. It is however to be understood that the present invention is not restricted to these examples.

EXAMPLE 1

4-(5-undecylpyrimidine-2-yl)phenyl 2-fluorophenyl 2-octyl-1-indanone-6-carboxylate (Example Compound No. 65) was synthesized through the following reaction steps (1) and (2).

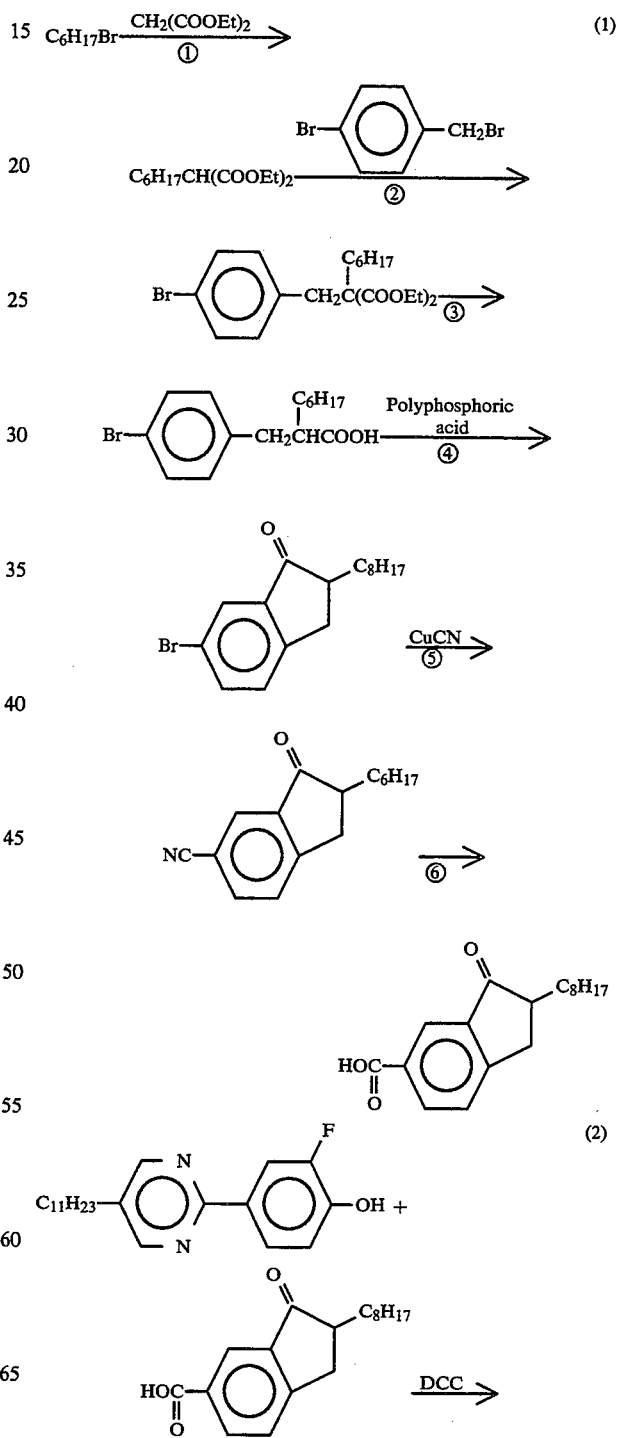

-continued

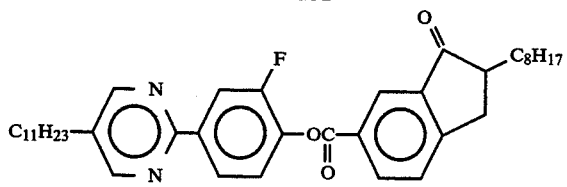

(1)

Production of 2-octyl-1-indanone-6-carboxylic acid

①

In a 10 liter-reaction vessel, 143 g (6.2 mol(M)) of metal sodium which had been cut small was added to 3.1 liters of anhydrous ethanol and dissolved therein. To the solution, 1025 g (6.4M) of diethyl malonate was added dropwise in 30 minutes at 40°–50° C. and 1200 g (6.2M) of n-octylbromide was further added thereto in 10 minutes at 40°–50° C., followed by heat-refluxing for 3 hours. After the reaction, about 2.5 liters of ethanol was distilled off from the reaction mixture. 2.5 liters of water was added to the residue and 2 liters of benzene was further added thereto to effect extraction. After the benzene layer was washed with saturated aqueous solution of common salt until the benzene layer showed neutrality, the resultant mixture was dried with anhydrous sodium sulfate, followed by distilling-off of benzene to obtain 1333 g of a crude product of diethyl 2-octylmalonate (Yield: 79%).

②

In a 10 liter-reaction vessel, 95.6 g (4.2 mol(M)) of metal sodium which had been cut small was added to 2.3 liters of anhydrous ethanol and dissolved therein. To the solution, 1130 g of diethyl 2-octylmalonate was added dropwise in 30 minutes at 40°–50° C. and 933 g (3.7M) of 4-bromobenzylbromide was further added thereto in 10 minutes at 40°–50° C., followed by heat-refluxing for 3 hours. After the reaction, about 1.5 liters of ethanol was distilled off from the reaction mixture. 1.5 liters of water was added to the residue and 1 liter of benzene was further added thereto to effect extraction. After the benzene layer was washed with saturated aqueous solution of common salt until the benzene layer showed neutrality, the resultant mixture was dried with anhydrous sodium sulfate, followed by distilling-off of benzene to obtain 1652 g of a crude product of diethyl 2-(4-bromobenzyl)-2-octylmalonate.

③

Then, in a 10 liter-reaction vessel, 1650 g of the above-prepared diethyl 2-(4-bromobenzyl)-2-noctyl malonate and 3.8 liters of methanol were placed. Under stirring, 1792 g (16M) of 50%-potassium hydroxide aqueous solution was added dropwise to the above mixture in 20 minutes, followed by heat-refluxing for 7 hours and then cooling. To the reaction mixture, 3500 g of 30%-sulfuric acid aqueous solution was added dropwise to acidify the reaction mixture. After cooling to room temperature, the acidified reaction mixture was subjected to extraction with 3 liters of ether. The ether layer was washed three times with 3 liters of saturated aqueous solution of common salt and dried with anhydrous sodium sulfate, followed by distilling-off of ether to obtain a residue. The residue was placed in a 3 liter-reaction vessel and stirred for 8 hour at 160° C. to obtain 1199 g of 2-(4-bromobenzyl)decanoic acid.

④

1190 g of the above-prepared 2-(4-bromobenzyl)-decanoic acid and 3750 g of polyphosphoric acid were placed in a 10 liter-reaction vessel and stirred for 6 hours at 80° C. After the reaction, the reaction mixture was poured into 5 liters of ice water to decompose the 2-(4-bromobenzyl)decanoic acid. The resultant reaction mixture was subjected to extraction with 3 liters of benzene. The benzene layer was washed two time with 3 liters of saturated aqueous solution of common salt and washed with 3 liters of 2% sodium hydroxide aqueous solution, followed by further washing with saturated aqueous solution of common salt until the benzene layer showed neutrality. The resultant benzene layer was dried with anhydrous sodium sulfate, followed by distilling-off of benzene and purification by silica gel column chromatography (eluent: hexane/chloroform=10/1) to obtain 317 g of 6-bromo-2-octyl-1-indanone.

⑤

Subsequently, 150 g ($4.7 \times 10^{-1}$M) of 6-bromo-2-octyl-1-indanone, 62.3 g ($7.0 \times 10^{-1}$M) of CuCN and 800 ml of dimethylformamide (DMF) were placed in a 2 liter-reaction vessel, followed by stirring for 6 hours at 160° C. After the reaction, the reaction mixture was cooled and poured into 3 liter of water and 100 ml of ethylenediamine was added, followed by extraction with ethyl acetate. The organic layer was washed with water, followed by drying with anhydrous magnesium sulfate and distilling-off of the solvent to obtain a crude product. The crude product was purified by silica gel column chromatography (eluent: n-hexane/-chloroform=1/1) to obtain 69.6 g of 6-cyano-2-octyl-1-indanone (Yield: 55%).

⑥

In a 500 ml-reaction vessel, 15.0 g ($5.58 \times 10^2$M) of the above-prepared 6-cyano-2-octyl-1-indanone, 15 g of potassium hydroxide, 225 ml of ethyleneglycol, and 75 ml of water were placed, followed by stirring for 6 hours at 130° C. After the reaction, the reaction mixture was poured in to 400 ml of water and acidified by 6N-hydrochloric acid to precipitate a crystal. The crystal was recovered by filtration and washed with water, followed by drying and recrystallization from ethanol to obtain 10.8 g of 2-octyl-1-indanone-6-carboxylic acid (Yield: 67%).

(2)

Production of 4-(5-undecylpyrimidine-2-yl)-2-fluorophenyl-2-octyl-1-indanone-6-carboxylate 0.42 g (1.45 mM) of 2-octyl-1-indanone-6-carboxylic acid, 0.42 g (1.45 mM) of 4-(5-undecylpyrimidine-2-yl)-2-fluorophenyl, 0.29 g (1.4 mM) of N,N'-dicyclohexyl-carbodiimide (DCC), 0.01 g of 4-dimethylaminopyridine and 10 ml of methylene chloride were placed in a flask, followed by stirring for 6 hours at room temperature. The resultant crystal was recovered by filtration. The filtrate was concentrated to obtain a crude product. The crude product was purified by silica gel column chromatography (eluent: toluene) and recrystallized from a mixture solvent (toluene/methanol) to obtain 0.62 g (1.0 mM) of 4-(5-undecylpyrimidine-2-yl)-2-fluorophenyl 2-octyl-1-indanone-6-carboxylate (Yield: 72%).

Phase transition temperature (°C.)

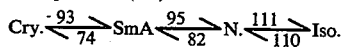

Herein, the respective symbols denote the following phase; Iso.: isotropic phase; Ch: cholesteric phase; N.: nematic phase; SmA: smectic A phase; SmC: smectic C phase; SmC*: chiral smectic C phase; Sm3: smectic phase other than SmA and SmC; and Cry.: crystal.

EXAMPLE 2

2-octyl-6-(5-decylpyrimidine-2-yl)-1-indanone (Ex. Comp. No. 141) was synthesized through the following reaction steps ① and ②.

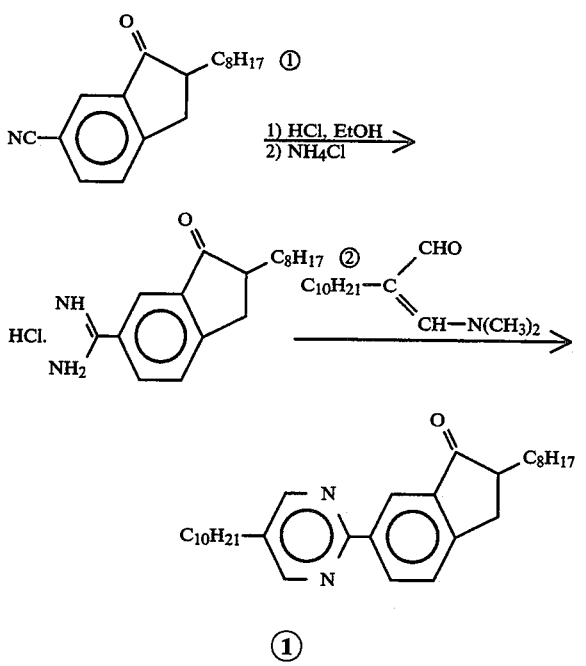

①

On an ice water bath, 8.0 g (29.7 mM) of 2-octyl-6-cyano-1-indanone, 2.82 g (61.2 mM) of ethanol and 85 ml of chloroform were placed in a flask. Hydrogen chloride (gas) was blowed into the above mixture solution until the mixture solution was saturated, followed by stirring overnight at room temperature. To the resultant mixture, a solution of 32.6 g of sodium hydroxide in 160 ml of water was added, followed by extraction with chloroform. The extracted solution was washed with saturated aqueous solution of common salt, followed by drying and distilling-off of solvent to obtain an imino ether.

Subsequently, 1.67 g (31.2 mM) of ammonium chloride and 32.5 ml of 75%-ethanol were added to the above-prepared imino ether, followed by refluxing for 1.5 hours. After the reaction, the reaction mixture was cooled on an ice water bath, and acetone was added thereto to precipitate a crystal. The crystal was recovered by filtration to obtain 6.1 g of 2-octyl-6-amidino-1-indanone hydrochloride (Yield: 63%).

②

1.0 g (3.1 mM) of 2-octyl-6-amidino-1-indanone hydrochloride, 0.38 g (7.0 mM) of sodium methylate, 0.78 g (3.26 mM) of α-decyl-β-dimethylaminoacrolein and 10 ml of methanol were placed in a 10 ml-round bottomed flask, followed by refluxing for 17 hours under stirring. After the reaction, the reaction mixture was cooled on an ice water bath to precipitate a crystal. The crystal was recovered by filtration and purified by silica gel column chromatography (eluent: toluene/ethyl acetate=100/1), followed by recrystallization from a mixture solvent (toluene/methanol) to obtain 0.59 g of 2-octyl-6-(5-decylpyrimidine-2-yl)-1-indanone (Yield: 41%, m.p.=83° C.).

EXAMPLE 3

2-octyl-6-[5-(4-octyl)phenyl-pyrimidine-2-yl]-1-indanone (Ex. Comp. No. 151) was synthesized through the following reaction step.

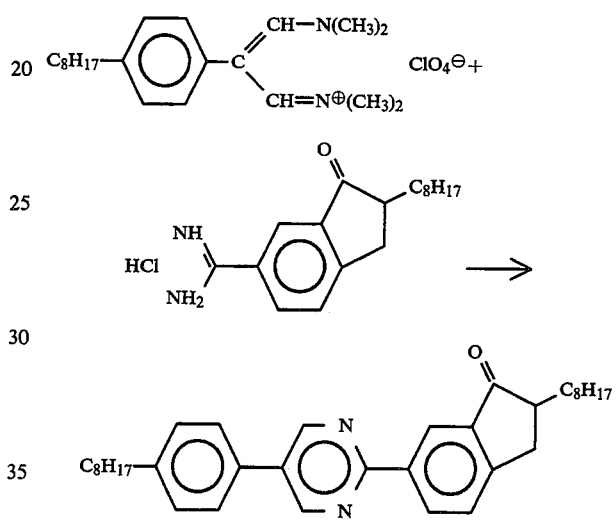

1.0 g (3.1 mM) of 2-octyl-6-amidino-1-indanone hydrochloride, 0.67 g (12.4 mM) of sodium methylate, 1.28 g (3.1 mM) of 3-dimethylamino-2-(4-octylphenyl)-N,N'-dimethylpropene-(2)-ammonium perchlorate and 30 ml of methanol were placed in a round bottomed flask and heat-refluxed for 4 hours under stirring. After the reaction, the reaction mixture was cooled to precipitate a crystal. The crystal was recovered by filtration, followed by purification by silica gel column chromatography (eluent: toluene/ethyl acetate=100/1) and recrystallization from mixture solvent (toluene/methanol) to obtain 0.98 g of 2-octyl-6-[5-(4-octyl)phenylpyrimidine-2-yl]-1-indanone (Yield: 62%).

Phase transition temperature (°C.)

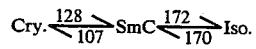

EXAMPLE 4

2-octyl-6-(5-decyloxypyrimidine-2-yl)-1-indanone (Ex. Comp. No. 145) was synthesized through the following reaction scheme.

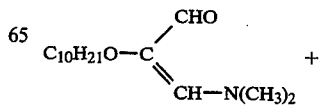

-continued

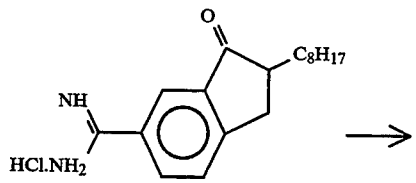

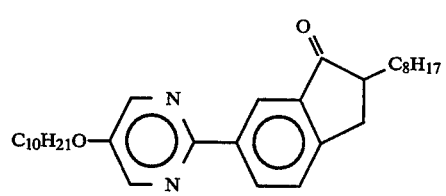

2-octyl-6-(5-decyloxypyrimidine-2-yl)-1-indanone was prepared in the same manner as in Example 2 except that α-decyloxy-β-dimethylaminoacrolein was used instead of α-decyl-β-dimethylaminoacrolein (Yield: 53%).

Phase transition temperature (°C.)

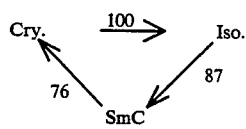

EXAMPLE 5

4-propylcyclohexyl-2-octyl-2-methyl-1-indanone-6-carboxylate (Ex. Comp. No. 138) was synthesized through the following reaction steps (1) and (2).

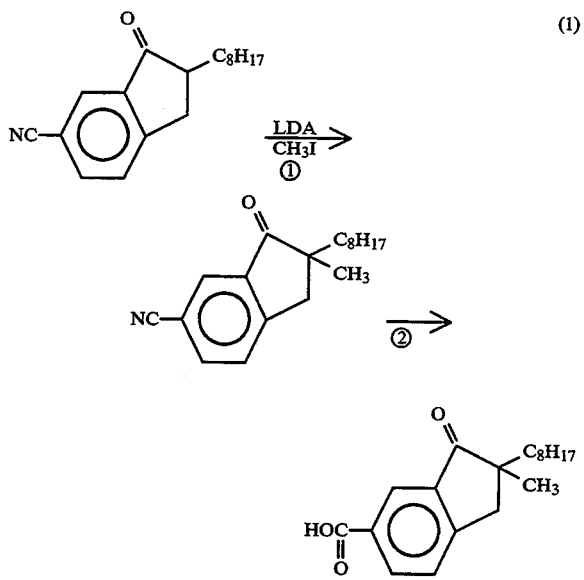

-continued

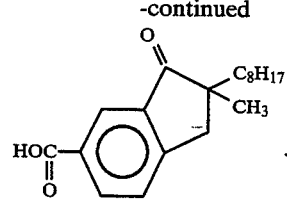

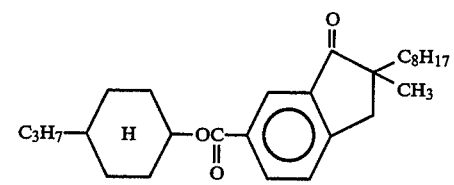

Production of 2-octyl-2-methyl-1-indanone-6-carboxylic acid.

①

In a 2 liter-reaction vessel, 1.6 g ($1.15 \times 10^{-1}$M) of diisopropylamine and 450 ml of dry THF were placed and cooled to $-10$ °C. Under stirring, 72.8 ml (1.5 M) of a solution of n-butyllithium in hexane was added dropwise to the above mixture in 10 minutes and cooled to $-70°$ C. A solution of 28.0g ($1.04 \times 10^{-1}$M) of 6-cyano-2-octyl-indanone in 150 ml of dry THF was then added dropwise in 30 minutes, followed by stirring for 2 hours while the reaction temperature was gradually restored to room temperature. After the reaction, the reaction mixture was cooled to $-20°$ C., and 28.0 g ($1.97 \times 10^{-1}$M) of methyl iodide was added dropwise thereto in 10 minutes. After the addition, the resultant mixture was stirred for 18 hours while the reaction temperature was gradually restored to room temperature. After the reaction, 1N-HCl was added dropwise to the reaction mixture under cooling to decompose the reaction mixture. The organic layer was successively washed with water, sodium hydrogencarbonate and water, followed by drying with anhydrous magnesium sulfate and distilling-off of the solvent to obtain a crude product. The crude product was purified by silica gel column chromatography (eluent: chloroform/n-hexane=1/1; 300 mesh silica gel: 50 times in weight) to obtain 15.2 g of 6-cyano-2-octyl-2-methyl-1-indanone (Yield: 52%).

②

In a 500 ml-reaction vessel, 14.7 g ($5.19 \times 10^{-2}$M) of 6-cyano-2-octyl-2-methyl-1-indanone, 15 g of KOH, 225 ml of ethylene glycol and 75 ml of water were placed and stirred for 4 hours at 130° C.

After the reaction, the reaction mixture was poured in to 400 ml of water and acidified by 6Nhydrochloric acid to precipitate a crystal. The crystal was recovered by filtration and washed with water, followed by drying and recrystallization from hexane to obtain 9.8 g of 2-octyl-2-methyl-1-indanone, 6-carboxylic acid (Yield: 63%).

(2)

Production of 4-propylcyclohexyl-2-octyl-2-methyl-1-indanone-6-carboxylate 0.3 g (1 mM) of 2-octyl-2-methyl-1-indanone-6-carboxylic acid, 0.14 g (1 mM) of 4-propylcyclohexanol, 0.21 g (1 mM) of DCC, 0.01 g of 4dimethylaminopyridine and 10 ml of methylene chloride were placed in a round-bottomed flask, followed by stirring for 6 hours at room temperature. The resultant crystal was recovered by filtration after the reaction. The filtrate was concentrated to obtain a crude product. The crude product was purified by silica gel column chromatography (eluent: toluene) and recrystallized from a mixture solvent (toluene/methanol) to obtain 0.32 g (0.75 mM) of 4-propylcyclohexyl 2-octyl-2-methyl-1-indanone-6carboxylate (Yield: 75%, m.p.=54° C.).

EXAMPLE 6

4-(5-decyl-1,3,4-thiadiazole-2-yl)phenyl 2-octyl-2-methyl-1-indanone-6-carboxylate (Ex. Comp. No. 69) was synthesized through the following reaction scheme.

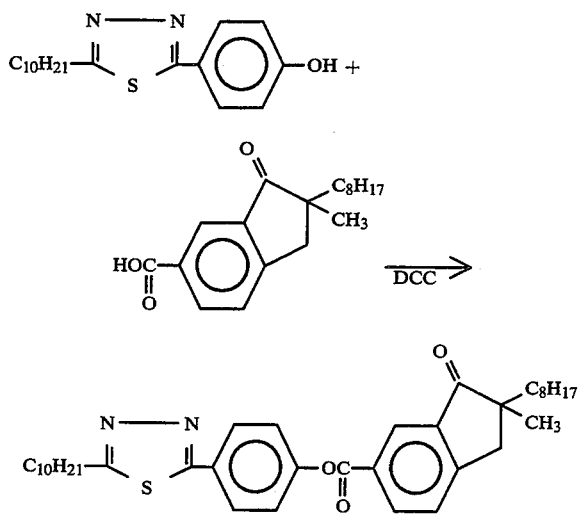

The above objective product was prepared in the same manner as in Example 5 except that 4-(5-decyl-1,3,4-thiadiazole-2-yl)phenol was used instead of 4-propylcyclohexanol (Yield: 77%, m.p.=109° C.).

EXAMPLE 7

2-hexyl-6-(5-decylpyrimidine-2-yl)-1-indanone (Ex. Comp. No. 6) was synthesized through the following reaction steps ① to ④.

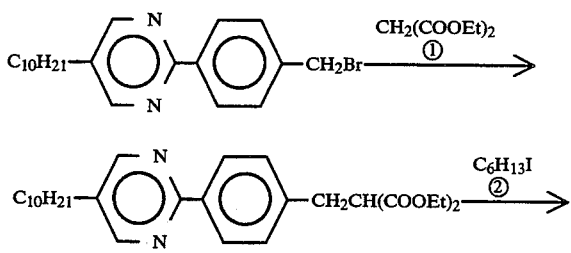

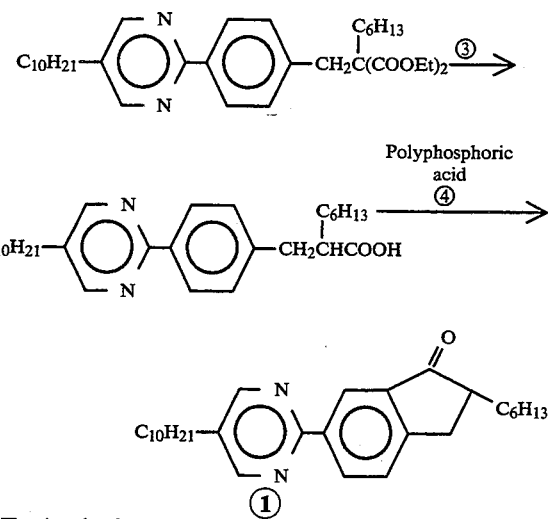

To 1 ml of DMF, 0.20 g (4.9 mM) of 60% sodium hydride and 0.79 g (4.9 mM) of diethyl malonate were added, followed by stirring for 30 minutes at room temperature. To the mixture, a mixture solution of 1.6 g (4.1 mM) of 2-(p-bromomethylphenyl)-5-decylpyrimidine and 2 ml of DMF was added, followed by stirring for 30 minutes at 50° C. After the reaction, the reaction mixture was subjected to extraction with ethyl acetate and washed with water, followed by drying with anhydrous sodium sulfate and distilling-off of the solvent to obtain a crude product. The crude product was purified by silica gel column chromatography (eluent: toluene-/ethyl acetate=15/1) to obtain 2.0 g of 2-[4-(5-decylpyrimidine-2-yl)benzyl]diethyl malonate.

②

To 1 ml of DMF, 0.1 g (2.5 mM) of 60% sodium hydride and 1.0 g (2.1 mM) of 2-[4-(5-decylpyrimidine-2-yl)benzyl]diethyl malonate were added, followed by stirring for 30 minutes at room temperature. To the mixture, a mixture solution of 0.5 g (2.35 mM) of hexyl iodide and 2 ml of DMF was added, followed by stirring for 3 hours at 90° C. After the reaction, the reaction mixture was subjected to extraction with ethyl acetate and washed with water, followed by drying with anhydrous sodium sulfate and distilling-off of the solvent to obtain a crude product. The crude product was purified by silica gel column chromatography (eluent: toluene-/ethyl acetate=20/1) to obtain 0.72 g (1.3 mM) of 2-hexyl-2-[4-(5-decylpyrimidine-2-yl)benzyl]diethyl malonate (Yield: 62%).

③

0.70 g (1.27 mM) of 2-hexyl-2-[4-(5-decylpyrimidine-2-yl)benzyl]diethyl malonate, 5 ml of methanol, 0.21 g (5.08 mM) of 95% sodium hydroxide were placed in a flask, followed by heat-refluxing for 7 hours. After the reaction, the reaction mixture was cooled and acidified with 6N-HCl, followed by extraction with ethyl acetate. After distilling-off of the solvent, the resultant residue was stirred for 3 hours at 180° C. to effect decarboxylation, whereby 0.43 g (0.95 mM) of 2-[4-(5-decylpyrimidine-2-yl)benzyl]octanoic acid was obtained (Yield: 75%). ④

0.4 g (0.88 mM) of 2-[4-(5-decylpyrimidine-2-yl)benzyl]octanoic acid and 1.3 g of polyphosphoric acid were placed in a flask, followed by stirring for 6 hours at 130°

C. After the reaction, 10 ml of water was added to the reaction mixture, followed by extraction with toluene. The extract was dried, followed by distilling-off of the solvent to obtain a crude product. The crude product was purified by silica gel column chromatography (eluent: toluene/ethyl acetate=100/1) and recrystallized from a mixture solvent (toluene/methanol) to obtain 0.25 g (0.57 mM) of 2-hexyl-6-(5-decylpyrimidine-2-yl)-1-indanone (Yield: 65%, m.p.=87° C.).

EXAMPLE 8

A liquid crystal composition A was prepared by mixing the following compounds including the compound (Ex. Comp. No. 141) prepared in Example 2 in the respectively indicated proportions.

| Structural formula | wt. parts |
|---|---|
| $C_6H_{13}$–[pyrimidine]–[phenyl]–$OC_{12}H_{25}$ | 4.22 |
| $C_8H_{17}$–[pyrimidine]–[phenyl]–$OC_9H_{19}$ | 8.44 |
| $C_8H_{17}$–[pyrimidine]–[phenyl]–$OC_{10}H_{21}$ | 8.44 |
| $C_9H_{19}$–[pyrimidine]–[phenyl]–$OC_8H_{17}$ | 4.22 |
| $C_{10}H_{21}O$–[phenyl]–CO–O–[phenyl]–$OCH_2CH(CH_3)C_2H_5$ | 16.88 |
| $C_6H_{13}$–[benzothiazole]–[phenyl]–$OC_8H_{17}$ | 21.11 |
| $C_5H_{11}$–[phenyl]–CH=N–N=CH–[phenyl]–$C_5H_{11}$ (thiadiazole) | 5.27 |
| $C_6H_{13}$–[phenyl]–[thiadiazole]–[phenyl]–$C_4H_9$ | 5.27 |
| $C_{11}H_{23}$–[pyrimidine]–[phenyl]–OC(O)–[thiophene]–$C_4H_9$ | 7.06 |
| $C_{11}H_{23}$–[pyrimidine]–[fluorophenyl]–OC(O)–[thiophene]–$C_4H_9$ | 3.54 |
| $C_{10}H_{21}$–[pyrimidine]–[phenyl]–$OCH_2CHFC_6H_{13}$ | 10.55 |

| Structural formula | wt. parts |
|---|---|
| -continued | |
| C10H21 pyridine-phenyl-indanone with C8H17, H | 5.0 |

The liquid crystal composition A showed the following phase transition series.

Phase transition temperature (°C.)

Cry. $\xrightarrow{-17.8}$ SmC* $\xrightarrow{62.6}$ SmA $\xrightarrow{73.0}$ Ch. $\xrightarrow{79.0}$ Iso.

EXAMPLE 9

Two 0.7 mm-thick glass plates were provided and respectively coated with an ITO film to form an electrode for voltage application, which was further coated with an insulating layer of vapor-deposited SiO$_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell.

Then, the liquid crystal composition A prepared in Example 8 was heated into an isotropic liquid, and injected into the above prepared cell under vacuum and, after sealing, was gradually cooled to 25° C. at a rate of 20° C./hour to prepare a ferroelectric liquid crystal device. The cell gap was found to be about 2 microns as measured by a Berek compensator.

Each of the ferroelectric liquid crystal devices was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

| | 10° C. | 30° C. | 40° C. |
|---|---|---|---|
| Response time ($\mu$sec) | 281 | 106 | 74 |
| Ps (nC/cm$^2$) | 14.4 | 10.3 | 8.7 |

EXAMPLE 10

A liquid crystal composition B was prepared by mixing the following compounds including a compound (Ex. Comp. No. 65) prepared in Example 1 in the respectively indicated proportions.

| Structural formula | wt. parts |
|---|---|
| C6H13—pyrimidine—phenyl—OC12H25 | 4.0 |
| C8H17—pyrimidine—phenyl—OC9H19 | 8.0 |
| C8H17—pyrimidine—phenyl—OC10H21 | 8.0 |
| C9H19—pyrimidine—phenyl—OC8H17 | 4.0 |

-continued

| Structural formula | wt. parts |
|---|---|
| 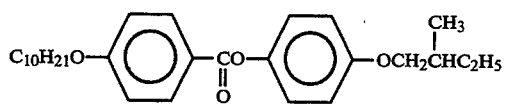 C$_{10}$H$_{21}$O—〇—CO—O—〇—OCH$_2$CHC$_2$H$_5$ (CH$_3$) | 26.0 |
| 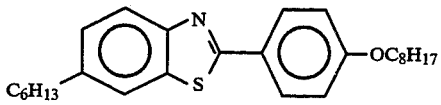 C$_6$H$_{13}$—benzothiazole—〇—OC$_8$H$_{17}$ | 20.0 |
| 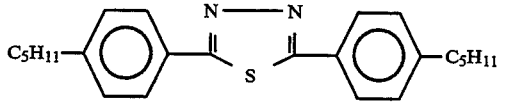 C$_5$H$_{11}$—〇—CH=N—N=CH—〇—C$_5$H$_{11}$ (thiadiazole) | 2.5 |
| 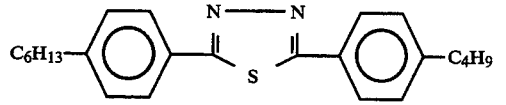 C$_6$H$_{13}$—〇—CH=N—N=CH—〇—C$_4$H$_9$ (thiadiazole) | 2.5 |
| 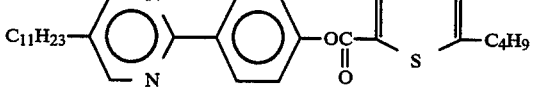 C$_{11}$H$_{23}$—pyrimidine—〇—O—CO—thiophene—C$_4$H$_9$ | 3.33 |
| 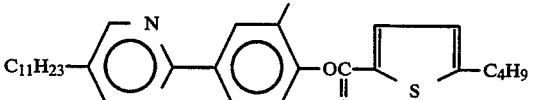 C$_{11}$H$_{23}$—pyrimidine—〇(F)—O—CO—thiophene—C$_4$H$_9$ | 1.7 |
| 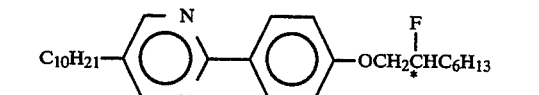 C$_{10}$H$_{21}$—pyrimidine—〇—OCH$_2$*CHC$_6$H$_{13}$ (F) | 10.0 |
| 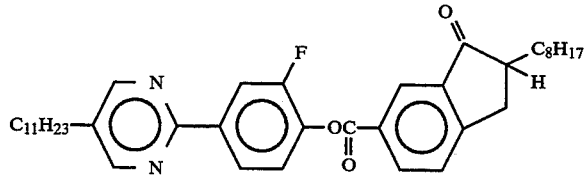 C$_{11}$H$_{23}$—pyrimidine—〇(F)—O—CO—indanone (C$_8$H$_{17}$, H) | 10.0 |

The liquid crystal composition B showed the following phase transition series.

Phase transition temperature (°C.)

Cry. $\xrightarrow{-10.8}$ SmC* $\xrightarrow{53.2}$ SmA $\xrightarrow{64.0}$ Ch. $\xrightarrow{75.2}$ Iso.

A ferroelectric liquid crystal device was prepared in the same manner as in Example 9 except for using the composition B. The ferroelectric liquid crystal device was subjected to measurement of Ps and response time in the same manner as in Example 9, whereby the following results were obtained.

| | 10° C. | 30° C. | 40° C. |
|---|---|---|---|
| Response time (μsec) | 512 | 268 | 169 |
| Ps (nC/cm$^2$) | 10.9 | 7.6 | 5.7 |

EXAMPLE 11

A liquid crystal composition C was prepared by mixing the following compounds in the respectively indicated proportions.

| Structural formula | wt. parts |
|---|---|
| 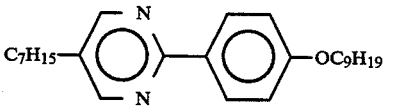 C$_7$H$_{15}$—pyrimidine—〇—OC$_9$H$_{19}$ | 12 |

-continued
| Structural formula | wt. parts |
|---|---|
| 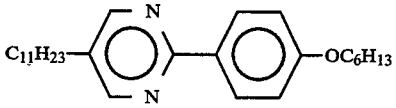 | 10 |
| 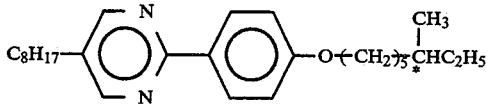 | 10 |
| 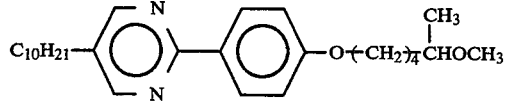 | 3 |
| 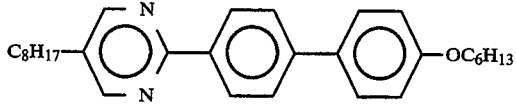 | 8 |
| 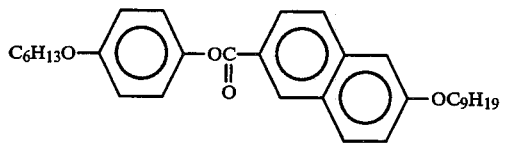 | 4 |
| 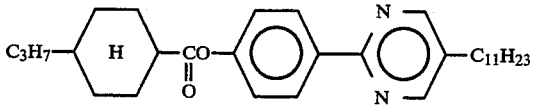 | 6 |
| 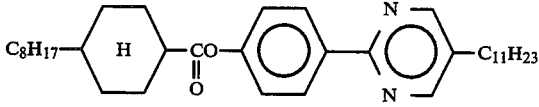 | 2 |
| 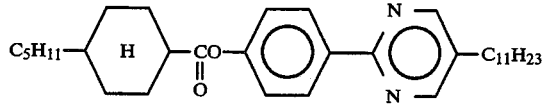 | 8 |
| 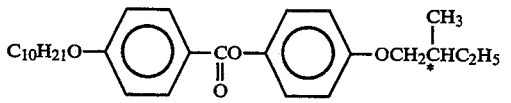 | 15 |
| 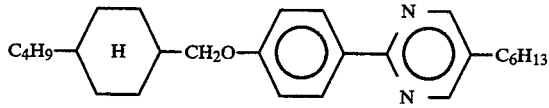 | 7 |
| 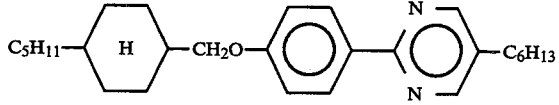 | 7 |
| 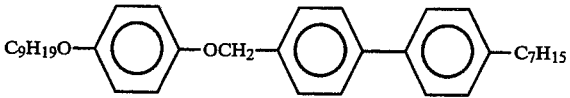 | 4 |
| 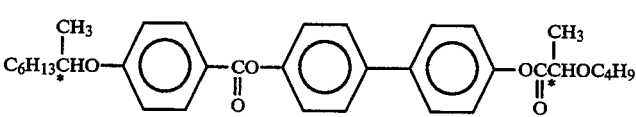 | 2 |

-continued

| Structural formula | wt. parts |
|---|---|
| $C_{12}H_{25}$—[pyrazine]—[phenyl]—OC(=O)CHClCH(CH$_3$)C$_2$H$_5$ (with * chiral centers) | 2 |

The liquid crystal composition C was further mixed with the following compounds in the proportions indicated below to provide a liquid crystal composition D.

| Ex. Comp. No. | Structural Formula | wt. parts |
|---|---|---|
| 5 | $C_{11}H_{23}O$—[cyclohexyl]—[phenyl]—[indanone with $C_{11}H_{23}$, $CH_3$ at 2-position] | 3 |
| 14 | $C_6H_{13}$—[thiophene]—[phenyl]—[indanone with $C_8H_{17}$, H at 2-position] | 3 |
| 63 | $C_{10}H_{21}$—[pyrazine]—[phenyl]—OC(=O)—[indanone with $C_{10}H_{21}$, H at 2-position] | 3 |
| Composition C | | 91 |

A ferroelectric liquid crystal device was prepared and subjected to measurement of response time in the same manner as in Example 9 except for injecting the composition C alone into the cell, whereby the following results were obtained.

| | 10° C. | 25° C. | 40° C. |
|---|---|---|---|
| Response time (μsec) | 640 | 318 | 176 |

COMPARATIVE EXAMPLE 1

A ferroelectric liquid crystal device was prepared and subjected to measurement of response time in the same manner as in Example 9 except for injecting the composition C prepared in Example 11 into the cell, whereby the following results were obtained.

| | 10° C. | 25° C. | 40° C. |
|---|---|---|---|
| Response time (μsec) | 784 | 373 | 197 |

EXAMPLE 12

A liquid crystal composition E was prepared by mixing the following Example Compounds instead of those of (5), (14) and (63) used in Example 15 in the indicated proportions with the liquid crystal composition C.

| Ex. Comp. No. | Structural Formula | wt. parts |
|---|---|---|
| 12 | $C_4H_9$—[pyridine]—[phenyl]—[indanone with $C_{12}H_{25}$, H at 2-position] | 3 |

-continued

| Ex. Comp. No. | Structural Formula | wt. parts |
|---|---|---|
| 51 | [benzothiazole-phenyl-indanone structure with C6H13, C8H17, CH3 substituents] | 3 |
| 139 | [phenyl-pyrimidine-indanone structure with C9H19, C10H21, CH3 substituents] | 3 |
| | Composition C | 91 |

A ferroelectric liquid crystal device was prepared in the same manner as in Example 9 except that the above liquid crystal composition E was used, and the device was subjected to measurement of optical response time. The results of the measurement are shown below.

|  | 10° C. | 25° C. | 40° C. |
|---|---|---|---|
| Response time (μsec) | 638 | 322 | 186 |

A ferroelectric liquid crystal device was prepared in the same manner as in Example 9 except that the above liquid crystal composition E was used, and the device was subjected to measurement of optical response time. The results of the measurement are shown below.

|  | 10° C. | 25° C. | 40° C. |
|---|---|---|---|
| Response time (μsec) | 598 | 295 | 162 |

EXAMPLE 13

A liquid crystal composition F was prepared by mixing the following Example Compounds instead of those of (5), (14) and (63) used in Example 11 in the indicated proportions with the liquid crystal composition C.

EXAMPLE 14

A liquid crystal composition G was prepared by mixing the following compounds in the indicated proportions.

| Ex. Comp. No. | Structural Formula | wt. parts |
|---|---|---|
| 23 | [fluorophenyl ester indanone structure with C10H21O, F, C2H5, H substituents] | 3 |
| 33 | [naphthalene-indanone structure with C10H21, C7H15, H substituents] | 2 |
| 83 | [phenyl-pyrimidine-indanone structure with CH3OCHCH2O—, CH3, C15H31, H substituents] | 2 |
| | Composition C | 93 |

| Structural formula | wt. parts |
|---|---|
| 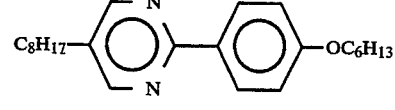 | 10 |
| 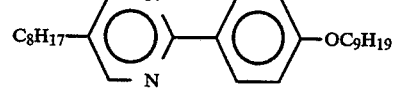 | 5 |
| 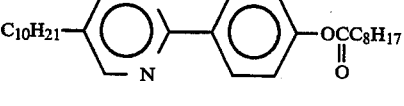 | 7 |
| 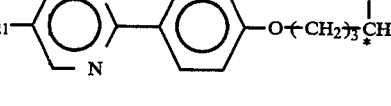 | 7 |
| 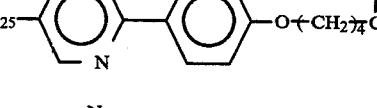 | 6 |
| 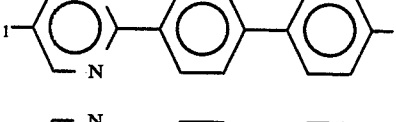 | 5 |
| 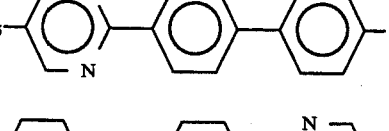 | 5 |
|  | 8 |
|  | 8 |
|  | 20 |
| 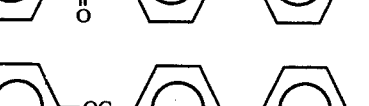 | 5 |
| 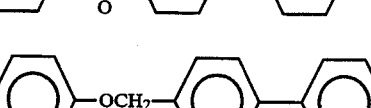 | 5 |
|  | 6 |

-continued

| Structural formula | wt. parts |
|---|---|
| 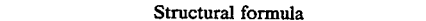 | 3 |

The liquid crystal composition G was further mixed with the following compounds in the proportions indicated below to provide a liquid crystal composition H.

| Ex. Comp. No. | Structural Formula | wt. parts |
|---|---|---|
| 98 | $CH_3$-[thiophene]-CO-O-[pyridine]-[indanone with $C_{11}H_{23}$, H] | 2 |
| 120 | $C_9H_{19}$-[phenyl]-[H cyclohexyl]-$OCH_2$-[indanone with $C_8H_{17}$, H] | 3 |
| 124 | $C_8H_{17}$-[thiophene]-CO-O-[phenyl]-[indanone with $C_6H_{12}CH=CH_2$, $CH_3$] | 2 |
| Composition G | | 93 |

A ferroelectric liquid crystal device was prepared in the same manner as in Example 9 except that the above liquid crystal composition H was used, and the device was subjected to measurement of optical response time. The results of the measurement are shown below.

| | 10° C. | 25° C. | 40° C. |
|---|---|---|---|
| Response time (μsec) | 515 | 264 | 140 |

COMPARATIVE EXAMPLE 2

A ferroelectric liquid crystal device was prepared and subjected to measurement of response time in the same manner as in Example 9 except for injecting the composition G prepared in Example 14 into the cell, whereby the following results were obtained.

| | 10° C. | 25° C. | 40° C. |
|---|---|---|---|
| Response time (μsec) | 653 | 317 | 159 |

EXAMPLE 15

A liquid crystal composition I was prepared by mixing the following Example Compounds instead of those of (98), (120) and (124) used in Example 14 in the indicated proportions with the liquid crystal composition G.

| Ex. Comp. No. | Structural Formula | wt. parts |
|---|---|---|
| 9 |  | 3 |

-continued

| Ex. Comp. No. | Structural Formula | wt. parts |
|---|---|---|
| 108 | [structure: CF$_3$, C$_6$H$_{13}$-phenyl-OCH$_2$-thiazole-N=CH-indanone with C$_5$H$_{11}$, CH$_3$] | 3 |
| 133 | [structure: C$_6$H$_{13}$CHF*CH$_2$O-phenyl-OC(=O)-indanone with C$_8$H$_{17}$, CH$_3$] | 3 |
| | Composition G | 91 |

A ferroelectric liquid crystal device was prepared in the same manner as in Example 9 except that the above cated proportions with the liquid crystal composition G.

| Ex. Comp. No. | Structural Formula | wt. parts |
|---|---|---|
| 20 | [structure: C$_6$H$_{13}$-benzoxazole-indanone with C$_6$H$_{13}$, C$_2$H$_5$] | 3 |
| 78 | [structure: C$_8$H$_{17}$-thiazole-N=CH-phenyl-CH$_2$O-phenyl-indanone with C$_{10}$H$_{21}$, H] | 3 |
| 128 | [structure: C$_6$H$_{13}$-cyclohexyl-OC(=O)-indanone with CH$_2$CH*(H)OC$_2$H$_5$, CH$_3$] | 3 |
| | Composition G | 91 | liquid crystal composition I was used, and the device was subjected to measurement of optical response time. The results of the measurement are shown below.

| | 10° C. | 25° C. | 40° C. |
|---|---|---|---|
| Response time (μsec) | 410 | 205 | 108 |

EXAMPLE 16

A liquid crystal composition J was prepared by mixing the following Example Compounds instead of those of (98), (120) and (124) used in Example 14 in the indi- A ferroelectric liquid crystal device was prepared in the same manner as in Example 9 except for using the composition J was used, and the device was subjected to measurement of optical response time. The results of the measurement are shown below.

| | 10° C. | 25° C. | 40° C. |
|---|---|---|---|
| Response time (μsec) | 480 | 242 | 127 |

EXAMPLE 17

A liquid crystal composition K was prepared by mixing the following compounds in the indicated proportions.

| Structural formula | wt. parts |
|---|---|
| 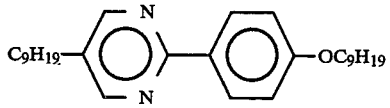 | 6 |
| 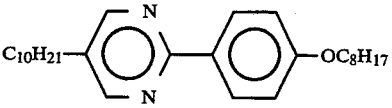 | 6 |
| 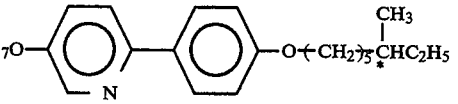 | 7 |
| 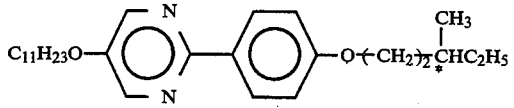 | 14 |
| 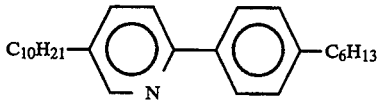 | 8 |
| 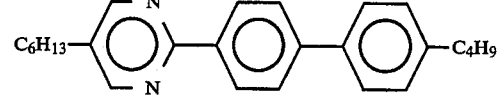 | 4 |
| 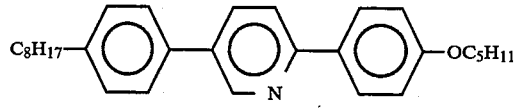 | 2 |
| 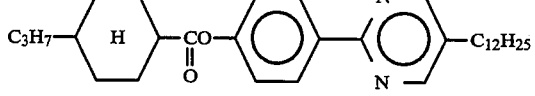 | 10 |
| 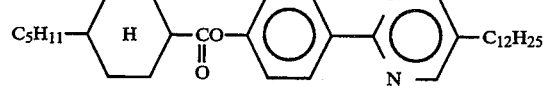 | 5 |
| 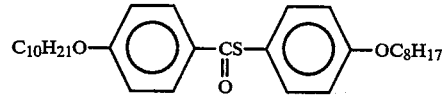 | 10 |
| 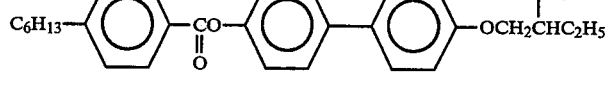 | 7 |
| 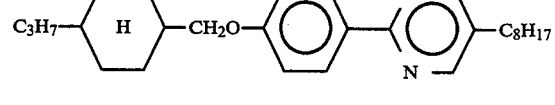 | 7 |
| 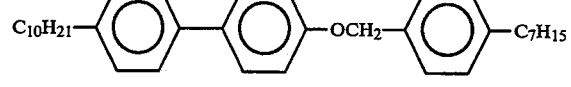 | 5 |

-continued

| Structural formula | wt. parts |
|---|---|
| 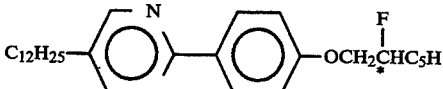 | 2 |
| | 2 |
| | 2 |
| | 3 |

The liquid crystal composition K was further mixed with the following compounds in the proportions indicated below to provide a liquid crystal composition L.

same manner as in Example 9 except for injecting the composition K prepared in Example 17 into the cell, whereby the following results were obtained.

| Ex. Comp. No. | Structural Formula | wt. parts |
|---|---|---|
| 27 | 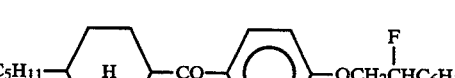 | 2 |
| 71 | | 2 |
| 107 | | 2 |
| | Composition K | 91 |

A ferroelectric liquid crystal device was prepared in the same manner as in Example 9 except that the above liquid crystal composition L was used, and the device was subjected to measurement of optical response time. The results of the measurement are shown below.

| | 10° C. | 25° C. | 40° C. |
|---|---|---|---|
| Response time ($\mu$sec) | 515 | 271 | 148 |

COMPARATIVE EXAMPLE 3

A ferroelectric liquid crystal device was prepared and subjected to measurement of response time in the

| | 10° C. | 25° C. | 40° C. |
|---|---|---|---|
| Response time ($\mu$sec) | 668 | 340 | 182 |

EXAMPLE 18

A liquid crystal composition M was prepared by mixing the following Example Compounds instead of those of (27), (71) and (107) used in Example 17 in the indicated proportions with the liquid crystal composition K.

| Ex. Comp. No. | Structural formula | wt. parts |
|---|---|---|
| 19 | [benzothiazole-indanone structure with $C_{10}H_{21}$, $C_3H_7$, $CH_3$ substituents] | 2 |
| 147 | [pyrimidine-indanone structure with $C_5H_{11}O$, $C_{10}H_{21}$, H substituents] | 3 |
| 156 | [pyrimidine-phenyl-indanone structure with $C_5H_{11}$, $C_9H_{19}$, H substituents] | 3 |
| Composition K | | 91 |

A ferroelectric liquid crystal device was prepared in the same manner as in Example 9 except that the above liquid crystal composition M was used, and the device was subjected to measurement of optical response time. The results of the measurement are shown below.

|  | 10° C. | 25° C. | 40° C. |
|---|---|---|---|
| Response time (μsec) | 503 | 265 | 143 |

EXAMPLE 19

A liquid crystal composition N was prepared by mixing the following Example Compounds instead of those of (27), (71) and (107) used in Example 17 in the indicated proportions with the liquid crystal composition K.

| Ex. Comp. No. | Structural formula | wt. parts |
|---|---|---|
| 47 | [thiophene-phenyl-indanone structure with $C_9H_{19}$, $C_{14}H_{29}$, H substituents] | 3 |
| 96 | [thiophene-pyrimidine-indanone structure with $C_7H_{15}$, $C_9H_{19}$, $CH_3$ substituents] | 3 |
| 109 | [cyclohexyl-thiadiazole-indanone structure with $C_{12}H_{25}$, H, $C_6H_{13}$, H substituents] | 3 |
| Composition K | | 91 |

A ferroelectric liquid crystal device was prepared in the same manner as in Example 9 except that the above liquid crystal composition N was used, and the device was subjected to measurement of optical response time. The results of the measurement are shown below.

|  | 10° C. | 25° C. | 40° C. |
|---|---|---|---|
| Response time (μsec) | 532 | 283 | 155 |

As apparent from the above Examples 11 to 19, the ferroelectric liquid crystal device containing the liquid crystal compositions D, E, F, H, I, J, L, M and N according to the present invention provided improved operation characteristic at a lower temperature, high speed responsiveness and a decreased temperature dependence of response speed.

EXAMPLE 20

A blank cell was prepared in the same manner as in Example 9 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition D prepared in Example 11. The liquid crystal device was subjected to measurement response time in the same manner as in Example 9. The results are shown below.

|  | 10° C. | 25° C. | 40° C. |
|---|---|---|---|
| Response time (μsec) | 632 | 311 | 170 |

EXAMPLE 21

A blank cell was prepared in the same manner as in Example 9 except for omitting the SiO$_2$ layer to form an alignment control layer composed of the polyimide resin layer alone on each electrode plate. A ferroelectric liquid crystal devices were prepared by filling such a blank cell with liquid crystal composition D prepared in Example 11. The liquid crystal device was subjected to measurement of response time in the same manner as in Example 9. The results are shown below.

|  | 10° C. | 25° C. | 40° C. |
|---|---|---|---|
| Response time (μsec) | 612 | 302 | 164 |

As is apparent from the above Examples 20 and 21, also in the case of a different device structure, the device containing the ferroelectric liquid crystal composition D according to the present invention provided an improved low-temperature operation characteristic and a decreased temperature dependence of response speed similarly as in Example 11.

EXAMPLE 22

Optically active 4-(4-decyloxyphenyl)phenyl 2-methyl-2-octyl-1-indanone-6-carboxylate (Ex. Comp. No. 211) was synthesized through the following reaction scheme.

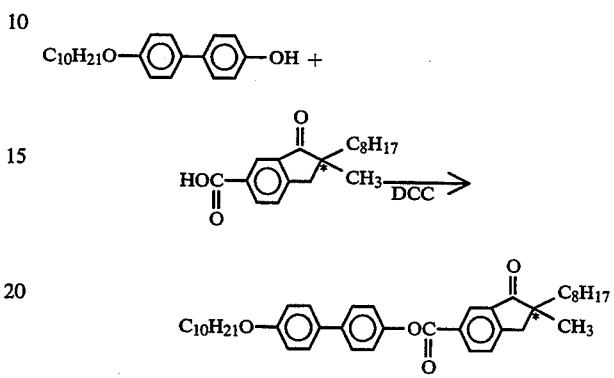

0.1 g (0.33 mM) of optically active 2-methyl-2-octyl-1-indanone-6-carboxylic acid, 0.12 g (0.36 mM) of 4-(4-decyloxyphenyl)phenol, 0.07 g (0.33 mM) of DCC, 0.01 g of 4-dimethylaminopyridine and 10 ml of dichloromethane were placed in a flask and stirred for 6 hours at room temperature to precipitate a crystal. The crystal was removed from the reaction mixture by filtration and the filtrate was concentrated to obtain a crude product. The crude product was purified by column chromatography (eluent: toluene) and recrystallized from a mixture solvent (toluene/ethanol) to obtain 0.15 g (0.25 mM) of optically active 4-(4-decyloxyphenyl)-phenyl 2-methyl-2-octyl-1-indanone-6-carboxylate (Yield: 76%).

Phase transition temperature (°C.)

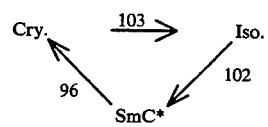

EXAMPLE 23

Optically active 4-(5-decylpyrimidine-2-yl)phenyl 2-methyl-2-octyl-1-indanone-6-carboxylate (Ex. Comp. No. 216) was synthesized through the following reaction scheme.

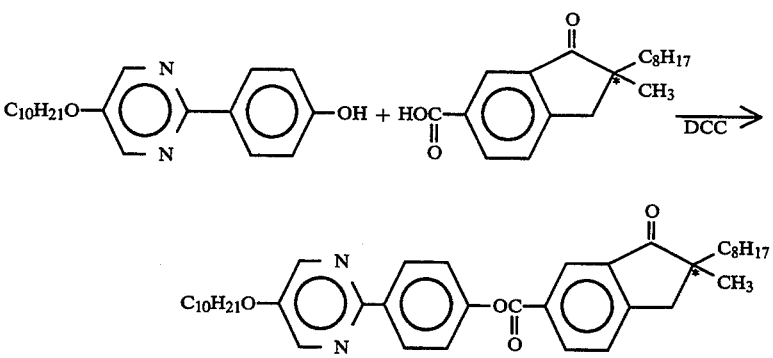

0.15 g (0.50 mM) of optically active 2-methyl-2-octyl-1-indanone-6-carboxylic acid, 0.16 g (0.52 mM) of 4-(5-decylpyrimidine-2-yl)phenol, 0.10 g (0.50 mM) of DCC, 0.02 g of 4-dimethylaminopyridine and 15 ml of dichloromethane were placed in a flask and stirred for 6 hours at room temperature to precipitate a crystal. The crystal was removed from the reaction mixture by filtration and the filtrate was concentrated to obtain a crude product. The crude product was purified by column chromatography (eluent: toluene) and recrystallized from a mixture solvent (toluene/ethanol) to obtain 0.25 g (0.42 mM) of optically active 4-(5-decylpyrimidine-2-yl)phenyl 2-methyl-2-octyl-1-indanone-6-carboxylate (Yield: 84%, m.p.=64° C.).

EXAMPLE 24

Optically active 4-[5-(4-octyloxyphenyl)pyrimidine-2-yl]phenyl 2-methyl-2-octyl-1-indanone-6-carboxylate (Ex. Comp. No. 278) was synthesized through the following reaction scheme.

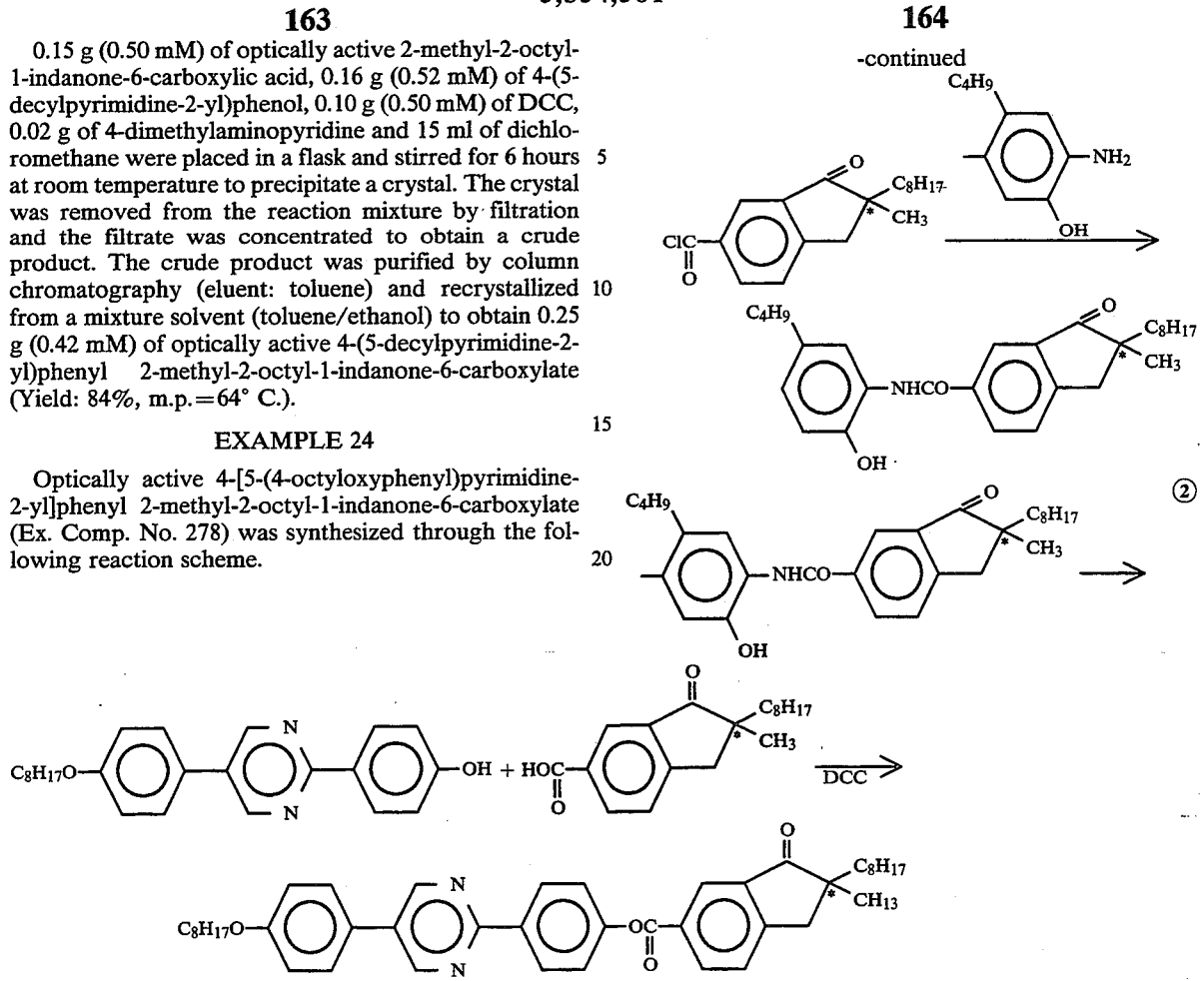

0.20 g (0.66 mM) of optically active 2-methyl-2-octyl-1-indanone-6-carboxylic acid, 0.25 g (0.66 mM) of 4-[5-(4-octyloxyphenyl)pyrimidine-2-yl]phenol, 0.13 g (0.66 mM) of DCC, 0.02 g of 4-dimethylaminopyridine and 20 ml of dichloromethane were placed in a flask and stirred for 6 hours at room temperature to precipitate a crystal. The crystal was removed from the reaction mixture by filtration and the filtrate was concentrated to obtain a crude product. The crude product was purified by column chromatography (eluent: toluene) and re-crystallized from a mixture solvent (toluene/ethanol) to obtain 0.31 g (0.47 mM) of optically active 4-[5-(4-octyloxyphenyl)pyrimidine-2-yl]phenyl 2-methyl-2-octyl-1-indanone-6-carboxylate (Yield: 71%).

Phase transition temperature (°C.)

$$Cry. \xrightarrow{108} Sm3 \underset{184}{\overset{186}{\rightleftarrows}} Iso.$$

EXAMPLE 25

2-(2-octyl-2-methyl-1-indanone-6-yl)-5-butylbenzoxazole (Ex. Comp. No. 204) was synthesized through the following reaction steps ① and ②.

0.5 g (1.66 mM) of optically active 2-methyl-2-octyl-1-indanone-6-carboxylic acid was modified into an acid chloride by using thionyl chloride. The acid chloride was dissolved in 5 ml of dioxane. To the solution, 0.26 g (1.6 mM) of 2-amino-4-butyl phenol and 0.5 ml of pyridine were successively added, followed by stirring for 30 minutes at 80° C. After the reaction, water was added to the reaction mixture, followed by extraction with benzene. The organic layer was dried with anhydrous sodium sulfate, followed by distilling-off of the solvent to obtain a crude product. The crude product was purified by silica gel column chromatography (eluent: toluene/ethyl acetate=20/1) to obtain 0.65 g (1.45 mM) of an amide compound (Yield: 91%).

②

To 0.3 g (0.67 mM) of the above-prepared amide compound, 2 ml of o-dichlorobenzene and 0.012 g of (0.063 mM) of p-toluenesulfonic acid monohydrate were added, followed by 3 hours at 160° C. After the reaction, the reaction mixture was purified by silica gel column chromatography (eluent: toluene) and recrystallized from a mixture solvent (toluene/ethanol) to obtain 0.25 g (0.58 mM) of optically active 2-(2-octyl-2-methyl-1-indanone-6-yl)-5-butylbenzoxazole (Yield: 87%, m.p.=93° C.).

EXAMPLE 26

Optically active 2-(2-octyl-2-methyl-1-indanone-6-yl)-5-hexyl benzoxazole (Ex. Comp. No. 279) was prepared in the same manner as in Example 25 (Yield: 82%. m.p.=61° C.).

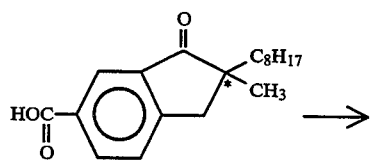

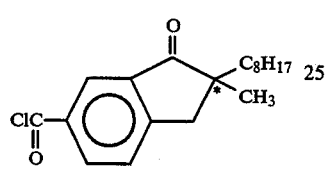

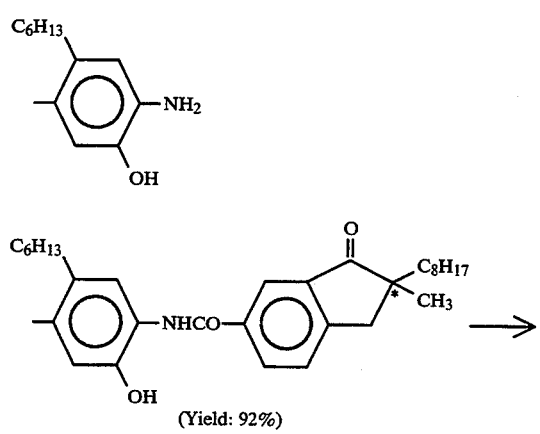

(Yield: 92%)

EXAMPLE 27

Optically active 2-methyl-2-octyl-6-[5-(4-octylphenyl)pyrimidine-2-yl]-1-indanone (Ex. Comp. No. 241) was synthesized through the following reaction steps (1) to (4).

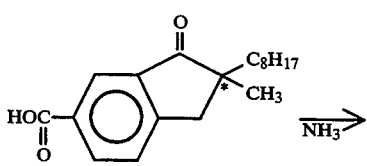

(1)

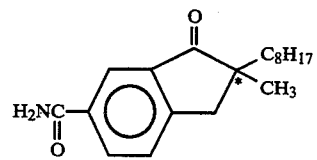

(2)

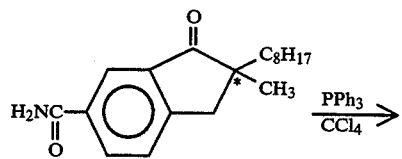

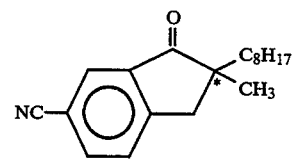

(3)

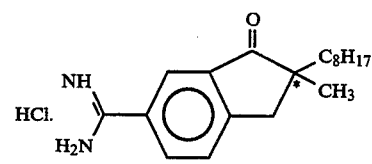

(4)

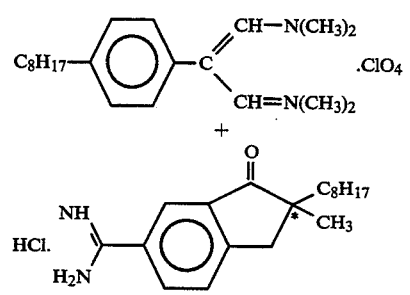

+

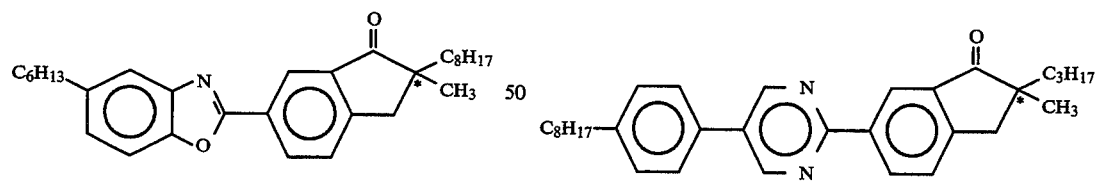

(1)

Production of 2-methyl-2-octyl-1-indanone-6-carboxylic acid amide 1.50 g (4.96 mM) of optically active 2-methyl-2-octyl-1-indanone-6-carboxylic acid was modified into an acid chloride by using 1.8 ml of thionyl chloride. To the acid chloride, 12 ml of ammonia water (28%) and 18 ml of THF were added, followed by stirring for 30 minutes on an ice water bath. After the reaction, 200 ml of water was added to the reaction mixture to precipitate a crystal. The crystal was recovered by filtration and recrystallized from methanol to obtain 1.39 g (4.6 mM) of 2-methyl-2-octyl-1-indanone-6-carboxylic acid amide (Yield: 93%).

(2)

Production of 2-methyl-2-octyl-6-cyano-1-indanone 1.36 g (4.51 mM) of the above-prepared 2-methyl-2-octyl-1-indanone-6-carboxylic acid amide, 2.37 g (9.04 mM) of triphenylphosphine, 7.2 ml of carbon tetrachloride and 7.2 ml of dry THF were mixed and stirred for 9 hours at 50° C. After the reaction, the solvent was removed from the reaction mixture by distillation, followed by purification by silica gel column chromatography (eluent: toluene) to obtain 0.78 g (2.9 mM) of 2-methyl-2-octyl-6-cyano-1-indanone (Yield: 64%).

(3)

Production of 2-methyl-2-octyl-6-amidino-1-indanone hydrochloride

On an ice water bath, 0.78 g (2.9 mM) of 2-methyl-2-octyl-6-indanone, 0.35 g (7.6 mM) of ethanol and 10 ml of chloroform were placed in a flask. Hydrogen chloride (gas) was blowed into the above mixture solution until the mixture solution was saturated, followed by stirring overnight at room temperature. To the resultant mixture, a solution of 4.0 g of sodium hydroxide in 20 ml of water was added, followed by extraction with chloroform. The extracted solution was washed with saturated aqueous solution of common salt, followed by drying and distilling-off of solvent to obtain an imino ether.

Subsequently, 0.20 g (3.74 mM) of ammonium chloride and 4.0 ml of 75%-ethanol were added to the above-prepared imino ether, followed by refluxing for 1.5 hours. After the reaction, the reaction mixture was cooled on an ice water bath, and acetone was added thereto to precipitate a crystal. The crystal was recovered by filtration to obtain 0.65 g of 2-methyl-2-octyl-6-amidino-1-indanone hydrochloride (Yield: 66%).

(4)

Production of optically active 2-methyl-2-octyl-6-[5-(4-octylphenyl)pyrimidine-2-yl]-1-indanone 0.25 g (0.74 mM) of 2-methyl-2-octyl-6-amidino-1-indanone hydrochloride, 0.16 g (2.96 mM) of sodium methylate, 0.31 g (0.75 mM) of 3-dimethylamino-2-(4-octylphenyl)-N,N'-dimethylpropane-(2)-ammonium perchlorate and 7 ml of methanol were placed in a round bottomed flask and heat-refluxed for 21 hours under stirring. After the reaction, the reaction mixture was cooled to precipitate a crystal. The crystal was recovered by filtration, followed by purification by silica gel column chromatography (eluent: toluene-/ethyl acetate=100/1) and recrystallization from mixture solvent (toluene/methanol) to obtain 0.22 g of 2-methyl-2-octyl-6-[5-(4-octylphenyl)pyrimidine-2-yl]-1-indanone (Yield: 57%).

Phase transition temperature (°C.)

$$Cry. \underset{75.1}{\overset{90.2}{\rightleftarrows}} Sm3 \underset{103.0}{\overset{109.7}{\rightleftarrows}} Iso.$$

EXAMPLE 28

A liquid crystal composition $A_1$ was prepared by mixing the following compounds in the respectively indicated proportions.

| Structural formula | wt. parts |
|---|---|
| $C_8H_{17}$—pyrimidine—phenyl—$OC_6H_{13}$ | 48.57 |
| $C_8H_{17}$—pyrimidine—phenyl—$OC_9H_{19}$ | 24.29 |
| $C_{10}H_{21}$—pyrimidine—phenyl—$OC_8H_{17}$ | 12.14 |
| $C_{11}H_{23}$—pyrimidine—phenyl—OC(=O)—cyclohexyl(H)—$C_3H_7$ | 3.75 |
| $C_{11}H_{23}$—pyrimidine—phenyl—OC(=O)—cyclohexyl(H)—$C_4H_9$ | 3.75 |

-continued

| Structural formula | wt. parts |
|---|---|
| C$_{11}$H$_{13}$-[pyrimidine ring with N,N]-[phenyl]-OC(=O)-[cyclohexyl H]-C$_5$H$_{11}$ | 7.50 |

The liquid crystal composition A$_1$ showed the following phase transition series.

Phase transition temperature (°C.)

$$Cry. \xrightarrow{10.3} SmC \xrightarrow{57.1} SmA \xrightarrow{62.8} N. \xrightarrow{78.2} Iso.$$

The liquid crystal composition A$_1$ was further mixed with optically active 4-(4-decyloxyphenyl)phenyl-methyl-2-octyl-1-indanone-6-carboxylate (Ex. Comp. No. 211) prepared in Example 22 in the proportions indicated below to provide liquid crystal compositions B$_1$, C$_1$ and D$_1$, respectively.

|  | Composition A$_1$ (wt. parts) | Ex. Comp. No. 211 (wt. parts) |
|---|---|---|
| Composition B$_1$ | 99.5 | 0.5 |
| Composition C$_1$ | 99.0 | 1.0 |
| Composition D$_1$ | 98.5 | 1.5 |

The above-prepared liquid crystal compositions B$_1$, C$_1$ and D$_1$ showed the following phase transition series, respectively.

| Composition | Phase transition temperature (°C.) |
|---|---|
| B$_1$ | $Cry \xrightarrow{7.3} SmC^* \xrightarrow{55.4} SmA \xrightarrow{60.2} Ch. \xrightarrow{75.8} Iso.$ |
| C$_1$ | $Cry \xrightarrow{7.1} SmC^* \xrightarrow{55.2} SmA \xrightarrow{60.0} Ch. \xrightarrow{75.6} Iso.$ |
| D$_1$ | $Cry \xrightarrow{7.0} SmC^* \xrightarrow{55.0} SmA \xrightarrow{59.6} Ch. \xrightarrow{75.5} Iso.$ |

Then, two glass plates which had not been subjected to alignment treatment were applied to each other to form a blank cell having a cell gap of 300 microns.

Each of the liquid crystal compositions B$_1$, C$_1$ and D$_1$ was injected into the above-prepared cell and subjected to magnetic field-alignment treatment, whereby a liquid crystal device was prepared.

The liquid crystal device was subjected to measurement of a helical pitch at chiral smectic C phase (SmC* pitch). Herein, a gap (or distance) between striped patterns (each adjacent two lines) corresponding to a helical pitch appearing at chiral smectic C phase is directly measured by a polarizing microscope to obtain an SmC* pitch.

Each of the liquid crystal compositions B$_1$, C$_1$ and D$_1$ provided the following SmC* pitch.

| Composition | SmC* pitch (m) at 30° C. |
|---|---|
| B$_1$ | 14.8 |
| C$_1$ | 5.3 |
| D$_1$ | 3.6 |

EXAMPLE 29

Liquid crystal compositions E$_1$ and F$_1$ were prepared by mixing optically active 2-methyl-2-octyl-6-[5-(4-octylphenyl)pyrimidine-2-yl]-1-indanone (Ex. Comp. No. 241) prepared in Example 27 with the liquid crystal composition A prepared in Example 28 in the indicated proportions, respectively.

|  | Composition A$_1$ (wt. parts) | Ex. Comp. No. 241 (wt. parts) |
|---|---|---|
| Composition E$_1$ | 99.7 | 0.3 |
| Composition F$_1$ | 99.4 | 0.6 |

The liquid crystal compositions E$_1$ and F$_1$ showed the following phase transition series.

| Composition | Phase transition temperature (°C.) |
|---|---|
| E$_1$ | $Cry \xrightarrow{7.4} SmC^* \xrightarrow{55.5} SmA \xrightarrow{60.9} Ch. \xrightarrow{76.1} Iso.$ |
| F$_1$ | $Cry \xrightarrow{7.2} SmC^* \xrightarrow{55.3} SmA \xrightarrow{60.3} Ch. \xrightarrow{75.5} Iso.$ |

Each of the liquid crystal compositions E$_1$ and F$_1$ was injected into a blank cell and subjected to measurement of an SmC* pitch in the same manner as in Example 28, whereby the following results were obtained.

| Composition | SmC* pitch (m) at 30° C. |
|---|---|
| E$_1$ | 22.6 |
| F$_1$ | 6.9 |

COMPARATIVE EXAMPLE 4

A liquid crystal composition F$_2$ was prepared by mixing an optically active compound shown below with the liquid crystal composition A$_1$ in the indicated proportions.

| <Composition F₁.> | |
|---|---|
| Composition A₁ | 90 (wt. parts) |
| 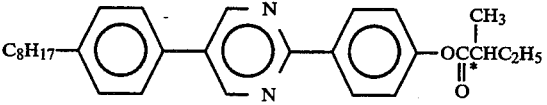 | 10 (wt. parts) |
| Phase transition temperature (°C.) | |
| Cry. $\xleftrightarrow{12.0}$ SmC* $\xleftrightarrow{62.0}$ SmA $\xleftrightarrow{68.0}$ Ch. $\xleftrightarrow{85.0}$ Iso. | |

The liquid crystal composition F₂ provided an SmC* pitch of 18 μm at 30° C.

EXAMPLE 30

A liquid crystal composition G₁ was prepared by mixing the following compounds in the respectively indicated proportions.

| Structural formula | wt. parts |
|---|---|
| 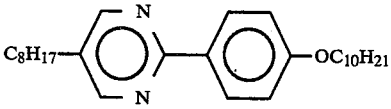 C₈H₁₇—[pyrimidine]—[phenyl]—OC₁₀H₂₁ | 20 |
| 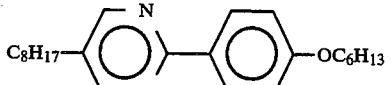 C₈H₁₇—[pyrimidine]—[phenyl]—OC₆H₁₃ | 10 |
| 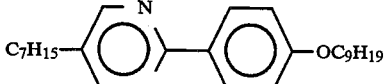 C₇H₁₅—[pyrimidine]—[phenyl]—OC₉H₁₉ | 10 |
| 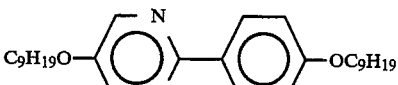 C₉H₁₉O—[pyrimidine]—[phenyl]—OC₉H₁₉ | 10 |
| 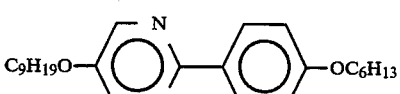 C₉H₁₉O—[pyrimidine]—[phenyl]—OC₆H₁₃ | 10 |
| 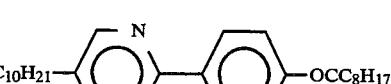 C₁₀H₂₁—[pyrimidine]—[phenyl]—OCC₈H₁₇ (C=O) | 10 |
| 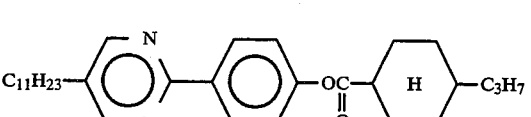 C₁₁H₂₃—[pyrimidine]—[phenyl]—OC(=O)—[cyclohexyl H]—C₃H₇ | 15 |
| 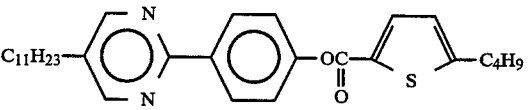 C₁₁H₂₃—[pyrimidine]—[phenyl]—OC(=O)—[thiophene S]—C₄H₉ | 10 |
| 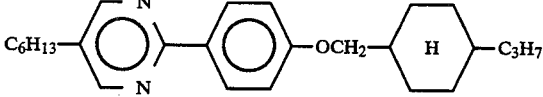 C₆H₁₃—[pyrimidine]—[phenyl]—OCH₂—[cyclohexyl H]—C₃H₇ | 5 |

The liquid crystal composition $G_1$ showed the following phase transition series.

Phase transition temperature (°C.)

$$Cry. \xleftrightarrow{3.4} SmC \xleftrightarrow{69.1} N. \xleftrightarrow{87.0} Iso.$$

The liquid crystal composition $G_1$ was further mixed with optically active 2-methyl-2-octyl-6-[5-(4-octylphenyl)pyrimidine-2-yl]-1-indanone (Ex. Comp. No. 241) prepared in Example 27 in the proportions indicated below to provide liquid crystal compositions $H_1$, $I_1$ and $J_1$, respectively.

|  | Composition $G_1$ (wt. parts) | Ex. Comp. No. 241 (wt. parts) |
|---|---|---|
| Composition $H_1$ | 99.7 | 0.3 |
| Composition $I_1$ | 99.4 | 0.6 |
| Composition $J_1$ | 99.0 | 1.0 |

The above-prepared liquid crystal compositions $H_1$, $I_1$ and $J_1$ showed the following phase transition series, respectively.

| Composition | Phase transition temperature (°C.) |
|---|---|
| $H_1$ | $Cry. \xleftrightarrow{3.4} SmC^* \xleftrightarrow{70.1} Ch. \xleftrightarrow{87.9} Iso.$ |
| $I_1$ | $Cry. \xleftrightarrow{3.4} SmC^* \xleftrightarrow{70.6} Ch. \xleftrightarrow{88.0} Iso.$ |
| $B_1$ | $Cry. \xleftrightarrow{3.5} SmC^* \xleftrightarrow{71.1} Ch. \xleftrightarrow{88.2} Iso.$ |

Each of the liquid crystal compositions $H_1$, $I_1$ and $J_1$ provided the following SmC* pitch.

| Composition | SmC* pitch (m) at 30° C. |
|---|---|
| $H_1$ | 17.1 |
| $I_1$ | 6.1 |
| $J_1$ | 4.0 |

COMPARATIVE EXAMPLE 5

A liquid crystal composition $J_2$ was prepared by mixing an optically active compound shown below with the liquid crystal composition $G_1$ in the indicated proportions.

<Composition $J_2$>

| | |
|---|---|
| Composition $G_1$ | 90 (wt. parts) |
| 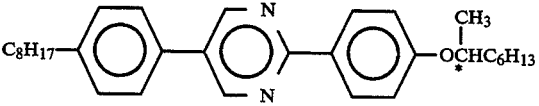 | 10 (wt. parts) |

Phase transition temperature (°C.)

$$Cry. \xleftrightarrow{5.0} SmC^* \xleftrightarrow{75.0} Ch. \xleftrightarrow{92.0} Iso.$$

The liquid crystal composition $J_2$ provided an SmC* pitch of 20 μm at 30° C.

As apparent from the above Examples 28 to 30 and Comparative Examples 4 and 5, the optically active compound according to the present invention is effective for providing an improved (or shortened) SmC* pitch. Moreover, the optically active compound does not substantially change phase transition temperatures of a (base) liquid crystal composition ($A_1$ or $G_1$) due to the low content of the optically active compound.

EXAMPLE 31

A liquid crystal composition $K_1$ was prepared by mixing the following compounds in the respectively indicated proportions.

| Structural formula | wt. parts |
|---|---|
| $C_6H_{13}O$—⟨phenyl⟩—⟨pyrimidine⟩—$C_8H_{17}$ | 51.57 |
| $C_9H_{19}O$—⟨phenyl⟩—⟨pyrimidine⟩—$C_8H_{17}$ | 25.79 |
| $C_8H_{17}O$—⟨phenyl⟩—⟨pyrimidine⟩—$C_{10}H_{21}$ | 12.89 |

| Structural formula | wt. parts |
| --- | --- |
| C₃H₁₇—[H]—CO—O—[phenyl]—[pyrimidine N,N]—C₁₁H₂₃ | 1.19 |
| C₄H₉—[H]—CO—O—[phenyl]—[pyrimidine N,N]—C₁₁H₂₃ | 1.19 |
| C₅H₁₁—[H]—CO—O—[phenyl]—[pyrimidine N,N]—C₁₁H₂₃ | 2.37 |
| C₁₂H₂₅—[pyrimidine N,N]—[phenyl]—OCH₂C*HC₆H₁₃ (F) | 2.50 |
| C₁₀H₂₁—[pyrimidine N,N]—[phenyl]—OCH₂C*HC₆H₁₃ (F) | 2.50 |

The liquid crystal composition K₁ showed the following phase transition series.

Phase transition temperature (°C.)

The liquid crystal composition K₁ was further mixed with optically active 2-methyl-2-octyl-6-[5-(4-octyl-phenyl)pyrimidine-2-yl]-1-indanone (Ex. Comp. No. 241) prepared in Example 27 in the proportions indicated below to provide liquid crystal compositions L₁, M₁ and N₁, respectively.

|  | Composition K₁ (wt. parts) | Ex. Comp. No. 241 (wt. parts) |
| --- | --- | --- |
| Composition L₁ | 99.0 | 1.0 |
| Composition M₁ | 97.0 | 3.0 |
| Composition N₁ | 95.0 | 5.0 |

The above-prepared liquid crystal compositions L₁, M₁ and N₁ showed the following phase transition series, respectively.

| Composition | Phase transition temperature (°C.) |
| --- | --- |
| L₁ | Cry. ←8.2→ SmC* ←48.5→ SmA ←63.3→ Ch. ←69.2→ Iso. |
| M₁ | Cry. ←7.5→ SmC* ←48.5→ SmA ←64.2→ Ch. ←68.9→ Iso. |
| N₁ | Cry. ←7.1→ SmC* ←48.6→ SmA ←64.5→ Ch. ←68.6→ Iso. |

EXAMPLE 32

Four liquid crystal devices were prepared in the same manner as in Example 9 except for using the liquid crystal compositions K₁, L₁, M₁ and N₁ prepared in Example 31. Each of the liquid crystal devices were subjected to measurement of Ps in the same manner as in Example 9. The results are shown below.

| Composition | Ps (nC/cm²) | | |
| --- | --- | --- | --- |
|  | 10° C. | 30° C. | 40° C. |
| K₁ | 3.5 | 2.4 | 1.8 |
| L₁ | 3.3 | 2.4 | 1.8 |
| M₁ | 3.5 | 2.3 | 1.7 |
| N₁ | 3.7 | 2.5 | 1.9 |

EXAMPLE 33

A liquid crystal composition O₁ was prepared by mixing the following compounds in the respectively indicated proportions.

| Structural formula | wt. parts |
| --- | --- |
| C₆H₁₃—[pyrimidine N,N]—[phenyl]—OC₁₂H₂₅ | 4.0 |

-continued

| Structural formula | wt. parts |
|---|---|
| C$_8$H$_{17}$—[pyrimidine]—[phenyl]—OC$_9$H$_{19}$ | 8.0 |
| C$_8$H$_{17}$—[pyrimidine]—[phenyl]—C$_{10}$H$_{21}$ | 8.0 |
| C$_9$H$_{19}$—[pyrimidine]—[phenyl]—OC$_8$H$_{17}$ | 4.0 |
| C$_{10}$H$_{21}$O—[phenyl]—CO·O—[phenyl]—OCH$_2$CH(CH$_3$)C$_2$H$_5$ | 26.0 |
| C$_6$H$_{13}$—[benzothiazole]—[phenyl]—OC$_8$H$_{17}$ | 20.0 |
| C$_5$H$_{11}$—[phenyl]—[thiadiazole]—[phenyl]—C$_5$H$_{11}$ | 5.0 |
| C$_6$H$_{13}$—[phenyl]—[thiadiazole]—[phenyl]—C$_4$H$_9$ | 5.0 |
| C$_{11}$H$_{23}$—[pyrimidine]—[phenyl]—OC(O)—[thiophene]—C$_4$H$_9$ | 6.7 |
| C$_{11}$H$_{23}$—[pyrimidine]—[F-phenyl]—OC(O)—[thiophene]—C$_4$H$_9$ | 3.3 |
| C$_{10}$H$_{21}$—[pyrimidine]—[F-phenyl]—OCH$_2$C*H C$_6$H$_{13}$ | 10.0 |

The liquid crystal composition O$_1$ showed the following phase transition series.

Phase transition temperature (°C.)

Cry. $\underset{\longleftarrow}{\overset{-13.7}{\longrightarrow}}$ SmC* $\underset{\longleftarrow}{\overset{56.0}{\longrightarrow}}$ SmA $\underset{\longleftarrow}{\overset{72.4}{\longrightarrow}}$ Ch. $\underset{\longleftarrow}{\overset{77.8}{\longrightarrow}}$ Iso.

The liquid crystal composition O$_1$ was further mixed with optically active 2-methyl-2-octyl-6-[5-(4-octylphenyl)pyrimidine-2-yl]-1-indanone (Ex. Comp. No. 241) prepared in Example 27 in the proportions indicated below to provide liquid crystal compositions P$_1$ and Q$_1$, respectively.

|  | Composition O$_1$ (wt. parts) | Ex. Comp. No. 241 (wt. parts) |
|---|---|---|
| Composition P$_1$ | 99.5 | 0.5 |
| Composition Q$_1$ | 99.0 | 1.0 |

The above-prepared liquid crystal compositions P$_1$ and Q$_1$ showed the following phase transition series, respectively.

| Composition | Phase transition temperature (°C.) |
|---|---|
| P$_1$ | Cry. $\underset{\longleftarrow}{\overset{-12.8}{\longrightarrow}}$ SmC* $\underset{\longleftarrow}{\overset{54.9}{\longrightarrow}}$ SmA $\underset{\longleftarrow}{\overset{71.7}{\longrightarrow}}$ Ch. $\underset{\longleftarrow}{\overset{76.6}{\longrightarrow}}$ Iso. |
| Q$_1$ | Cry. $\underset{\longleftarrow}{\overset{-12.5}{\longrightarrow}}$ SmC* $\underset{\longleftarrow}{\overset{55.5}{\longrightarrow}}$ SmA $\underset{\longleftarrow}{\overset{71.8}{\longrightarrow}}$ Ch. $\underset{\longleftarrow}{\overset{76.4}{\longrightarrow}}$ Iso. |

Three liquid crystal devices were prepared in the same manner as in Example 9 except for using the liquid crystal compositions O$_1$, P$_1$ and Q$_1$ prepared in Example 33. Each of the liquid crystal devices were subjected to measurement of Ps in the same manner as in Example 9. The results are shown below.

| Composition | Ps (nC/cm$^2$) | | |
|---|---|---|---|
|  | 10° C. | 30° C. | 40° C. |
| O$_1$ | 9.9 | 7.3 | 5.4 |
| P$_1$ | 10.0 | 7.6 | 5.5 |
| Q$_1$ | 10.0 | 7.6 | 5.8 |

EXAMPLE 34

SmC* pitches of the liquid crystal compositions prepared in Examples 31 and 33 were measured in the same manner as in Example 9. The results are shown below.

| Composition | SmC* pitch (m) at 30° C. |
|---|---|
| K$_1$ | 16.7 |
| L$_1$ | 2.5 |
| M$_1$ | 1.8 |
| N$_1$ | <1.0 |
| O$_1$ | 20.0 |
| P$_1$ | 11.7 |
| Q$_1$ | 7.1 |

As apparent from the results of the above Examples 31 to 34, an SmC* pitch of the (base) liquid crystal composition (K$_1$ or O$_1$) is shortened without markedly changing phase transition temperatures and spontaneous polarization of the liquid crystal composition by mixing the optically active compound of the present invention in a small amount.

EXAMPLE 35

A liquid crystal composition $R_1$ was prepared by mixing the following compounds in the indicated proportions.

| Structural formula | wt. parts |
|---|---|
| 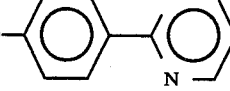 | 50.0 |
| 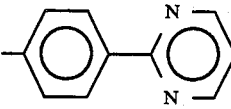 | 12.5 |
| 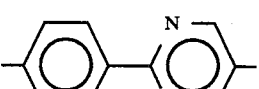 | 12.5 |
| 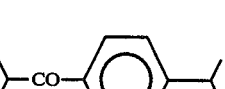 | 5.0 |
|  | 5.0 |
|  | 5.0 |
| 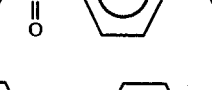 | 10.0 |

The liquid crystal composition $R_1$ was further mixed with optically active 2-(2-octyl-2-methyl-1-indanone-6-yl)-5-hexylbenzoxazole (Ex. Comp. No. 279) prepared in Example 26 in the proportions indicated below to provide a liquid crystal composition $S_1$.

|  | Composition $R_1$ | Ex. Comp. No. 279 |
|---|---|---|
| Composition $S_1$ | 99 (wt. parts) | 1.0 (wt. parts) |

Then, two liquid crystal devices were prepared in the same manner as in Example 9 except for using the liquid crystal compositions $R_1$ and $S_1$, and were subjected to observation of an alignment state. In the device using the composition $R_1$, liquid crystal molecules showed an ununiform alignment states (i.e., showed a poor uniaxial alignment characteristic at cholesteric phase and smectic A phase). On the other hand, in the device using the composition $S_1$, liquid crystal molecules showed a monodomain with a good and uniform alignment characteristic.

Further, the above two liquid crystal devices were subjected to measurement of Ch pitch according to a Wedge Cell Method of Cano as shown in "Oyobutsuri", 43, p. 125 (1974) by Matsumura and Iwayanagi.

The results are shown below.

| Composition | Ch pitch ($\mu$m) |
|---|---|
| $R_1$ | 3 or below |
| $S_1$ | 20 or above |

As apparent from the above results, the optically active compound according to the present invention is effective in controlling a Ch pitch and the liquid crystal composition (S) according to the present invention provides a good alignment characteristic.

EXAMPLE 36

A liquid crystal composition $T_1$ was prepared by mixing the following Example Compounds instead of those of (5), (14) and (63) used in Example 11 in the indicated proportions with the liquid crystal composition C.

| Ex. Comp. No. | Structural formula | wt. parts |
|---|---|---|
| 163 | 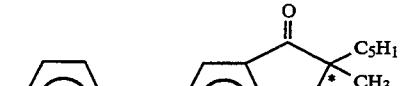 | 2 |
| 173 |  | 2 |
| 180 | 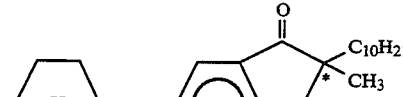 | 2 |

-continued

| Ex. Comp. No. | Structural formula | wt. parts |
|---|---|---|
| | Composition C | 94 |

A ferroelectric liquid crystal device was prepared in the same manner as in Example 9 except that the above liquid crystal composition $T_1$ was used, and the device was subjected to measurement of optical response time. The results of the measurement are shown below.

| | 10° C. | 25° C. | 40° C. |
|---|---|---|---|
| Response time (μsec) | 563 | 290 | 156 |

EXAMPLE 37

A liquid crystal composition $U_1$ was prepared by mixing the following Example Compounds instead of those of (5), (14) and (63) used in Example 11 in the indicated proportions with the liquid crystal composition C.

A ferroelectric liquid crystal device was prepared in the same manner as in Example 9 except that the above liquid crystal composition $U_1$ was used, and the device was subjected to measurement of optical response time. The results of the measurement are shown below.

| | 10° C. | 25° C. | 40° C. |
|---|---|---|---|
| Response time (μsec) | 543 | 280 | 151 |

EXAMPLE 38

A liquid crystal composition $V_1$ was prepared by mixing the following Example Compounds instead of those (98), (120) and (124) used in Example 14 in the indicated proportions with the liquid crystal composition G.

| Ex. Comp. No. | Structural formula | wt. parts |
|---|---|---|
| 171 | $C_8H_{17}S$—⟨phenyl⟩—$OCH_2$—⟨indanone with $C_8H_{17}$, $CH_3$⟩ | 3 |
| 198 | $C_9H_{19}O$—⟨pyrimidine⟩—⟨indanone with $C_9H_{19}$, $CH_3$⟩ | 1 |
| 221 | $C_6H_{13}$—⟨cyclohexyl H⟩—⟨phenyl⟩—$OCO$—⟨indanone with $C_5H_{11}$, $CH_3$⟩ | 2 |
| | Composition C | 94 |

| Ex. Comp. No. | Structural formula | wt. parts |
|---|---|---|
| 166 | $C_5H_{11}$—⟨phenyl⟩—$CO$—O—⟨indanone with $C_5H_{11}$, $CH_3$⟩ | 3 |
| 234 | $C_6H_{13}$—⟨benzoxazole⟩—⟨phenyl⟩—$CO$—O—⟨indanone with $C_9H_{19}$, $CH_3$⟩ | 3 |

| Ex. Comp. No. | Structural formula | wt. parts |
|---|---|---|
| 260 | [structure: $C_4H_9$—phenyl—pyrimidine—phenyl—COO—indanone with $C_9H_{19}$, $CH_3$ at *] | 2 |
| | Composition G | 92 |

A ferroelectric liquid crystal device was prepared in the same manner as in Example 9 except that the above liquid crystal composition $V_1$ was used, and the device was subjected to measurement of optical response time. The results of the measurement are shown below.

| | 10° C. | 25° C. | 40° C. |
|---|---|---|---|
| Response time (μsec) | 461 | 241 | 124 |

EXAMPLE 39

A liquid crystal composition $W_1$ was prepared by mixing the following Example Compounds instead of those of (98), (120) and (124) used in Example 14 in the indicated proportions with the liquid crystal composition G.

A ferroelectric liquid crystal device was prepared in the same manner as in Example 9 except that the above liquid crystal composition $W_1$ was used, and the device was subjected to measurement of optical response time and observation of switching states. In the device, a monodomain with a good and uniform. The results of the measurement are shown below.

| | 10° C. | 25° C. | 40° C. |
|---|---|---|---|
| Response time (μsec) | 451 | 239 | 122 |

EXAMPLE 40

A liquid crystal composition $X_1$ was prepared by mixing the following Example Compounds instead of those of (27), (71) and (107) used in Example 17 in the

| Ex. Comp. No. | Structural formula | wt. parts |
|---|---|---|
| 187 | [structure: $C_9H_{19}O$—naphthyl—OCO—indanone with $C_6H_{13}$, $CH_3$ at *] | 3 |
| 249 | [structure: $C_5H_{11}$—cyclohexyl—OCO—pyridine—indanone with $C_8H_{17}$, $CH_3$ at *] | 3 |
| 288 | [structure: $C_8H_{17}$—cyclohexyl—pyrimidine—indanone with $C_{11}H_{23}$, $CH_3$ at *] | 3 |
| | Composition G | 91 | indicated proportions with the liquid crystal composition K.

| Ex. Comp. No. | Structural formula | wt. parts |
|---|---|---|
| 189 | [structure: $C_8H_{17}$—indanyl—phenyl—OCO—indanone with $C_{10}H_{21}$, $CH_3$ at *] | 2 |

| Ex. Comp. No. | Structural formula | wt. parts |
|---|---|---|
| 210 | [structure: $C_8H_{17}$–phenyl–phenyl(F)–O–C(=O)–O–indanone with $C_{12}H_{25}$, $CH_3$ (chiral)] | 3 |
| | Composition K | 95 |

A ferroelectric liquid crystal device was prepared in the same manner as in Example 9 except that the above liquid crystal composition $X_1$ was used, and the device was subjected to measurement of optical response time. The results of the measurement are shown below.

| | 10° C. | 25° C. | 40° C. |
|---|---|---|---|
| Response time (μsec) | 470 | 246 | 139 |

EXAMPLE 41

A liquid crystal composition $Y_1$ was prepared by mixing the following Example Compounds instead of those of (27), (71) and (107) used in Example 17 in the indicated proportions with the liquid crystal composition K.

As apparent from the above Examples 36 to 41, the ferroelectric liquid crystal device containing the liquid crystal compositions $T_1$, $U_1$, $V_1$, $W_1$, $X_1$ and $Y_1$ according to the present invention provided improved operation characteristic at a lower temperature, high speed responsiveness and a decreased temperature dependence of response speed.

EXAMPLE 42

A blank cell was prepared in the same manner as in Example 9 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition $T_1$ prepared in Example 36. The liquid crystal device was

| Ex. Comp. No. | Structural formula | wt. parts |
|---|---|---|
| 168 | [structure: $C_9H_{19}C(=O)O$–phenyl–C(=O)O–indanone with $C_6H_{13}$, $CH_3$ (chiral)] | 3 |
| 192 | [structure: $C_7H_{15}$–thiazole–N–indanone with $C_4H_9$, $CH_3$ (chiral)] | 3 |
| 263 | [structure: $C_7H_{15}$–pyrimidine–phenyl–phenyl–O–C(=O)–indanone with $C_6H_{13}$, $CH_3$ (chiral)] | 2 |
| | Composition K | 92 |

A ferroelectric liquid crystal device was prepared in the same manner as in Example 9 except that the above liquid crystal composition $Y_1$ was used, and the device was subjected to measurement of optical response time. The results of the measurement are shown below.

| | 10° C. | 25° C. | 40° C. |
|---|---|---|---|
| Response time (μsec) | 478 | 248 | 139 |

Further, when the device was driven, a clear switching action was observed, and good bistability was shown after the termination of the voltage application.

subjected to measurement response time in the same manner as in Example 9. The results are shown below.

| | 10° C. | 25° C. | 40° C. |
|---|---|---|---|
| Response time (μsec) | 560 | 285 | 153 |

EXAMPLE 43

A blank cell was prepared in the same manner as in Example 9 except for omitting the $SiO_2$ layer to form an alignment control layer composed of the polyimide resin layer alone on each electrode plate. A ferroelectric liquid crystal devices were prepared by filling such a blank cell with liquid crystal composition T₁ prepared in Example 36. The liquid crystal device was subjected to measurement of response time in the same manner as in Example 9. The results are shown below.

|  | 10° C. | 25° C. | 40° C. |
| --- | --- | --- | --- |
| Response time (μsec) | 541 | 270 | 147 |

As is apparent from the above Examples 42 and 43, also in the case of a different device structure, the device containing the ferroelectric liquid crystal composition T₁ according to the present invention provided an improved low-temperature operation characteristic and a decreased temperature dependence of response speed similarly as in Example 36.

EXAMPLE 44

The liquid crystal device prepared by using the liquid crystal composition N₁ prepared in Example 31 was heated so that the liquid crystal composition N₁ showed an isotropic liquid state. Then, the liquid crystal device was gradually cooled to 30° C. while an alternating current signal (±20 V, 10 Hz) was applied.

The liquid crystal device was subjected to a microscope observation and a measurement of a transmitted light intensity (or transmittance) on condition that a bipolar pulse including a pulse A and a pulse B shown in FIG. 6 was set so as to have a pulse width of 100 μs and an applied voltage was changed from 0 V to 30 V. When the applied voltage was gradually increased, a reverse domain in stripes was observed in the direction of a layer of liquid crystal molecules. As the applied voltage was increased, the reverse domain grew larger. When the applied voltage reached 18 V, an entire display area was reversed to provide a striped reverse domain (FIG. 7).

As apparent from the above results, a liquid crystal device including a liquid crystal composition containing an optically active compound according to the present invention is usable for a gradation display.

As described hereinabove, according to the present invention, there is provided a mesomorphic compound of the formula (I) which can effectively be applied to a liquid crystal device utilizing ferroelectricity when the compound per se assumes a chiral smectic phase. Further, there is also provided a liquid crystal composition containing the compound and assuming a chiral smectic phase, whereby a liquid crystal device comprising the composition can be operated by utilizing ferroelectricity of the composition. The present invention provides a liquid crystal device using such a composition which shows a good switching characteristic, an improved low-temperature operation characteristic and a decreased temperature-dependence of response speed.

The present invention provides an optically active compound of the formula (II) which is effective in controlling a cholesteric pitch and a chiral smectic C pitch. A liquid crystal composition containing the optically active compound is usable for a liquid crystal device which can effect a gradation display.

The present invention further provides a display apparatus and a display method which employ the above-mentioned devices as a display unit, whereby good display characteristics can be obtained in combination with a light source, a drive circuit, etc.

What is claimed is:

1. A mesomorphic compound represented by the following formula (I):

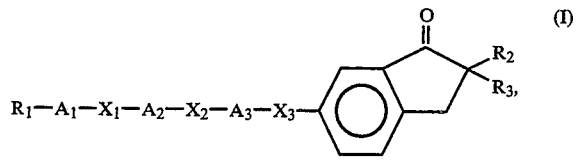

wherein

R₁, R₂ and R₃ independently denote hydrogen, halogen,

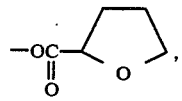

or a linear or branched alkyl group having 1-18 carbon atoms capable of including one or non-neighboring two or more —CH₂— groups which can be replaced with —O—, —S—,

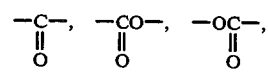

—CH=CH— or —C≡C— said linear or branched alkyl group being capable of including hydrogen which can be replaced with fluorine, with the proviso that R₂ and R₃ cannot be hydrogen simultaneously;

X₁, X₂ and X₃ independently denote a single bond,

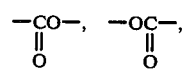

—CH₂O— or —OCH₂—;

A₂ and A₃ independently denote a single bond,

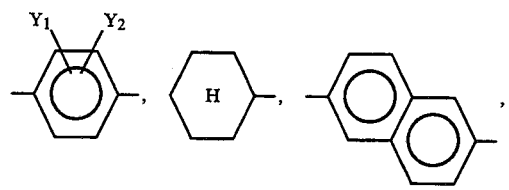

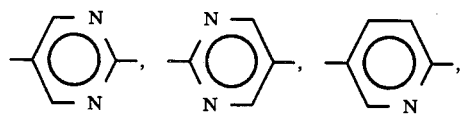

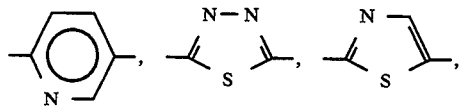

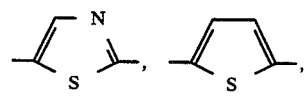

-continued

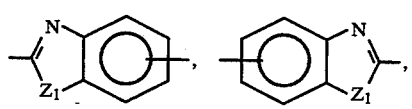

wherein $Y_1$ and $Y_2$ independently denote H, F, Cl, Br, $CH_3$, $CF_3$ or CN, and $Z_1$ denotes O or S; and $A_1$ denotes

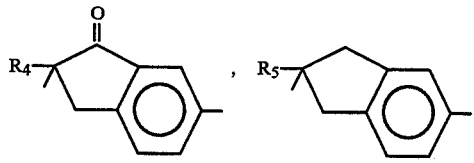

or $A_2$, wherein $R_4$ and $R_5$ independently denote hydrogen, or a linear or branched alkyl group having 1-18 carbon atoms, with the proviso that $A_1$ cannot be a single bond.

2. An optically active compound represented by the following formula (II):

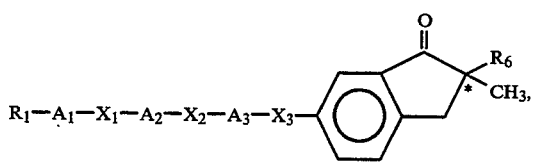 (II)

wherein $R_1$ denotes hydrogen, halogen, —CN,

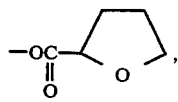

or a linear or branched alkyl group having 1-18 carbon atoms capable of including one or non-neighboring two or more —$CH_2$— groups which can be replaced with —O—, —S—,

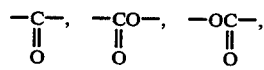

—CH=CH— or —C≡C—, said linear or branched alkyl group being capable of including hydrogen which can be replaced with fluorine;

$R_6$ denotes a linear alkyl group having 2-16 carbon atoms;

$X_1$, $X_2$ and $X_3$ independently denote a single bond,

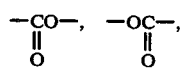

—$CH_2O$— or —$OCH_2$—;

$A_2$ and $A_3$ independently denote a single bond,

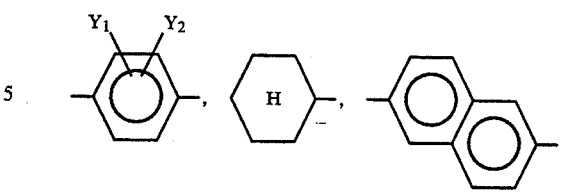

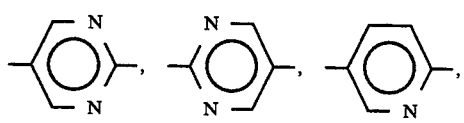

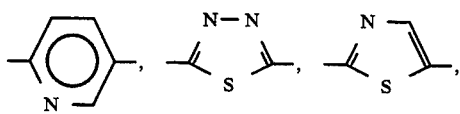

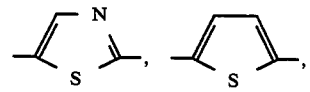

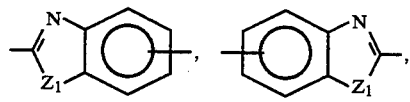

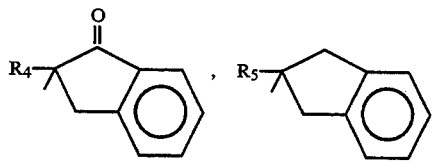

wherein $Y_1$ and $Y_2$ independently denote H, F, Cl, Br, $CH_3$, $CF_3$ or CN, and $Z_1$ denotes O or S; $A_1$ denotes

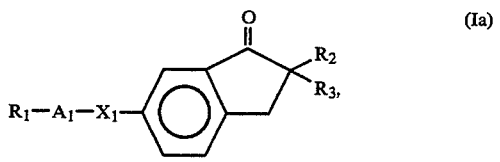

or $A_2$, wherein $R_4$ and $R_5$ independently denote hydrogen, or a linear or branched alkyl group having 1-18 carbon atoms; and \* denotes a location of an optically active center.

3. A mesomorphic compound according to claim 1, which is represented by any one of the following formula (Ia) to (Id):

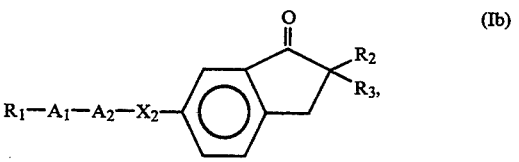 (Ia)

(Ib)

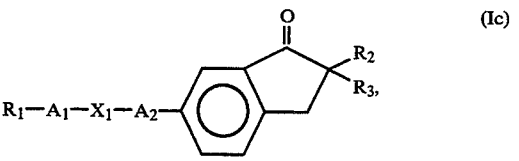 (Ic)

-continued
and

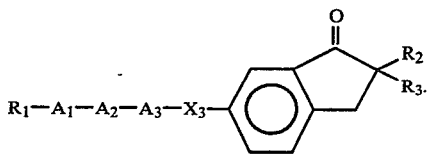

4. An optically active compound according to claim 2, which is represented by any one of the following formulas (IIa) to (IId):

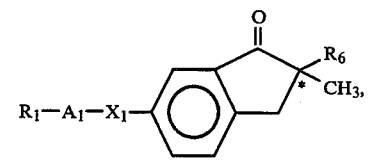

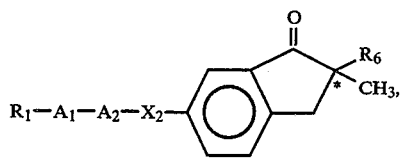

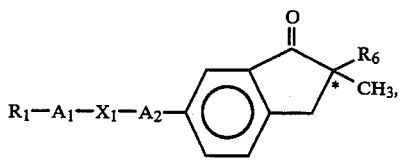

and

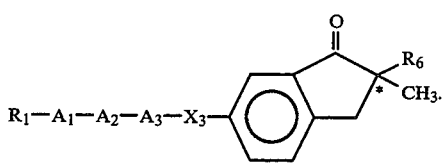

wherein
$R_1$ denotes hydrogen, halogen, —CN,

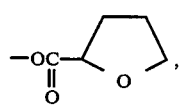

or a linear or branched alkyl group having 1-18 carbon atoms capable of including one or non-neighboring two or more —$CH_2$— groups which can be replaced with —O—, —S—, $$-\underset{\underset{O}{\|}}{C}-,\quad -\underset{\underset{O}{\|}}{CO}-,\quad -\underset{\underset{O}{\|}}{OC}-,$$

—CH=CH— or —C≡C—, said linear or branched alkyl group being capable of including hydrogen which can be replaced with fluorine:
$R_6$ denotes a linear alkyl group having 2-16 carbon atoms;
$X_1$, $X_2$ and $X_3$ independently denote a single bond, $$-\underset{\underset{O}{\|}}{CO}-,\quad -\underset{\underset{O}{\|}}{OC}-,$$

—$CH_2O$— or —$OCH_2$—;

$A_2$ and $A_3$ independently denote a single bond,

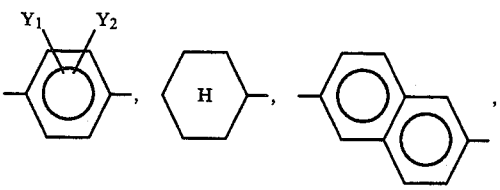

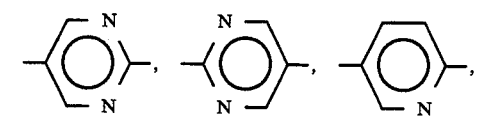

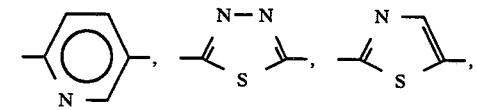

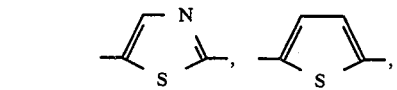

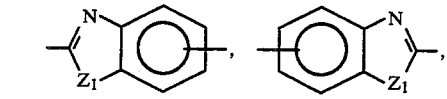

wherein $Y_1$ and $Y_2$ independently denote H, F, Cl, Br, $CH_3$, $CF_3$ or CN, and $Z_1$ denotes O or S;
$A_1$ denotes

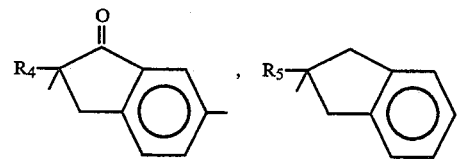

or $A_2$, wherein $R_4$ and $R_5$ independently denote hydrogen, or a linear or branched alkyl group having 1-18 carbon atoms; and
* denotes a location of an optically active center.

5. A mesomorphic compound according to claim 1, which is represented by any one of the following formulas (Iaa) to (Idc):

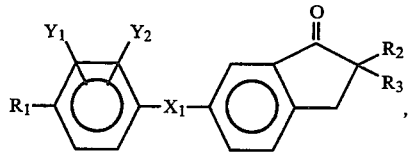

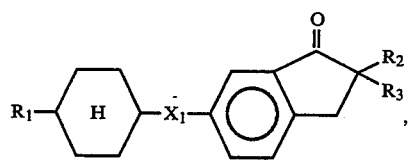 (Iab)
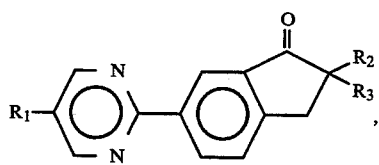 (Iac)
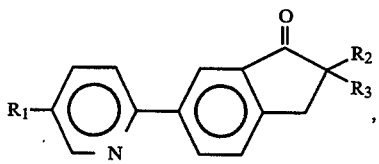 (Iad)
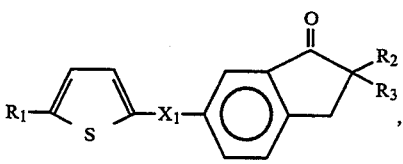 (Iae)
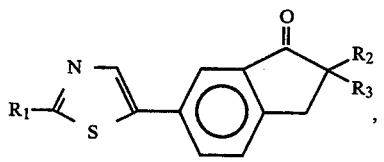 (Iaf)
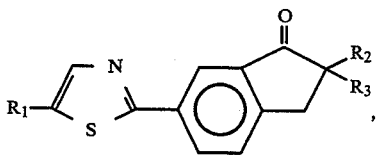 (Iag)
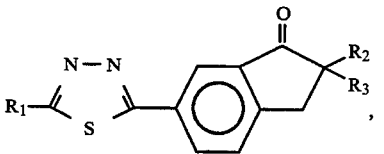 (Iah)
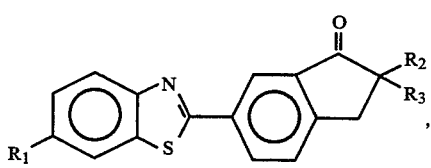 (Iai)
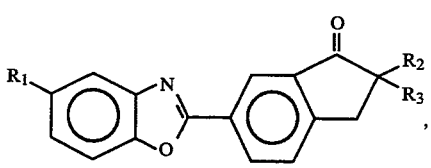 (Iaj)
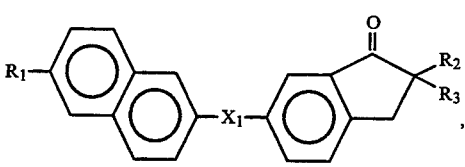 (Iak)
-continued

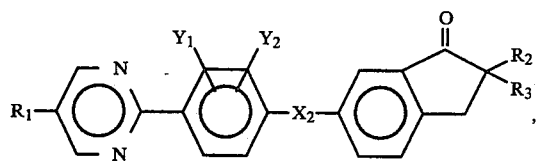
(Iba)
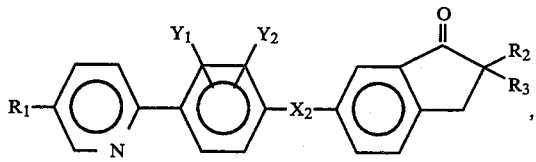
(Ibb)
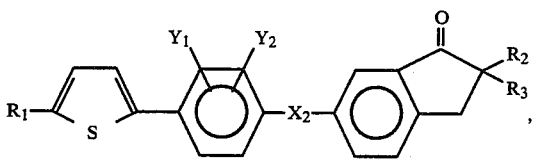
(Ibc)
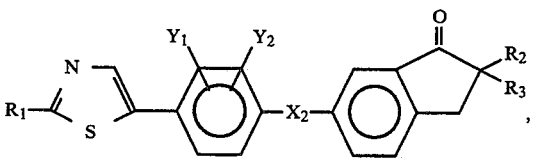
(Ibd)
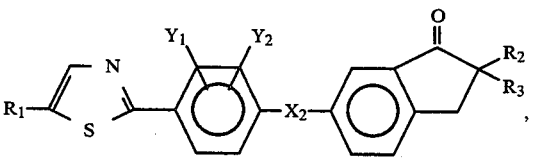
(Ibe)
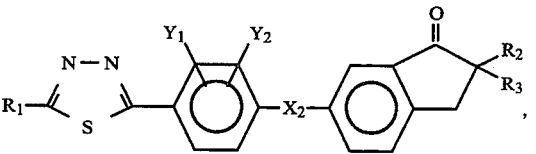
(Ibf)
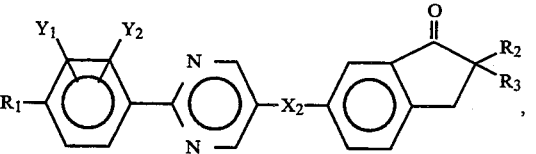
(Ibg)
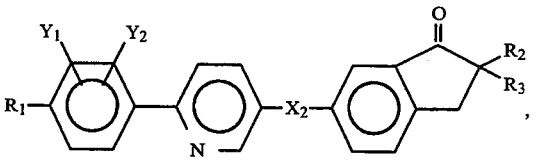
(Ibh)
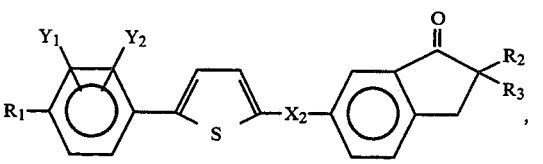
(Ibi)

-continued
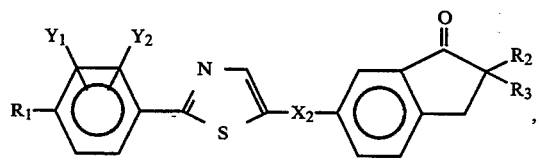
(Ibj)
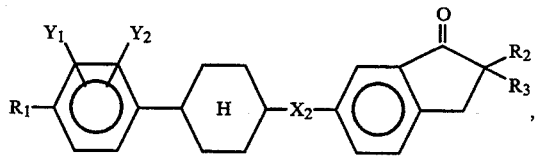
(Ibk)
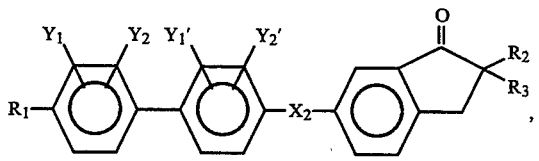
(Ibl)
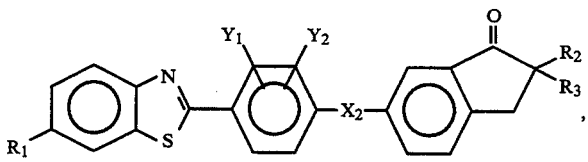
(Ibm)
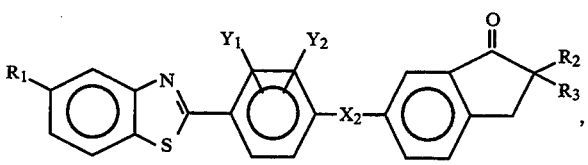
(Ibn)
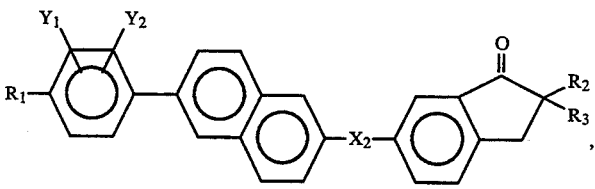
(Ibo)
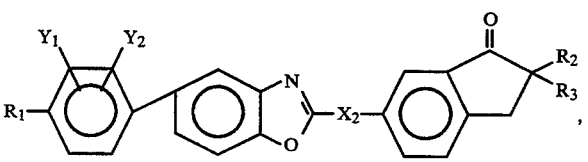
(Ibp)
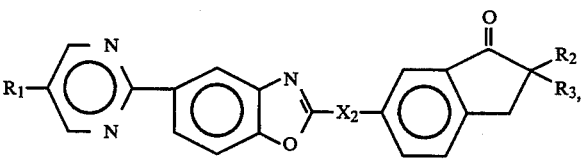
(Ibq)
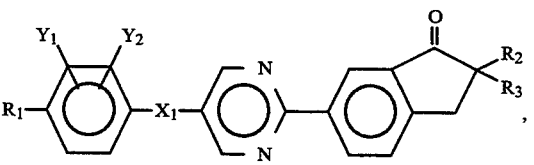
(Ica)
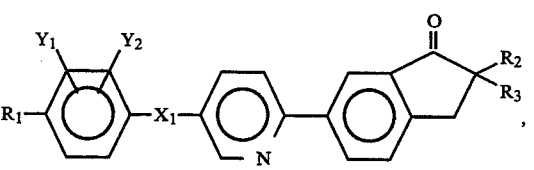
(Icb)

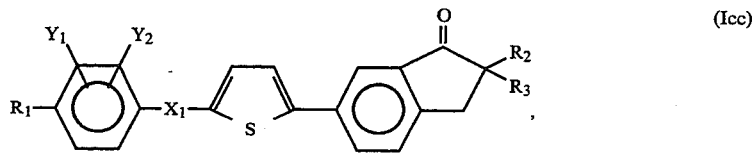
(Icc)
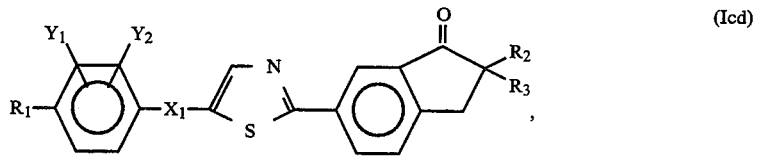
(Icd)
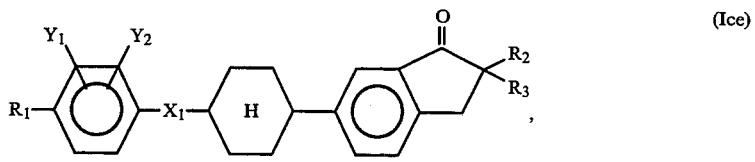
(Ice)
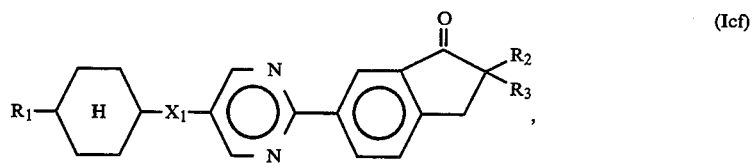
(Icf)
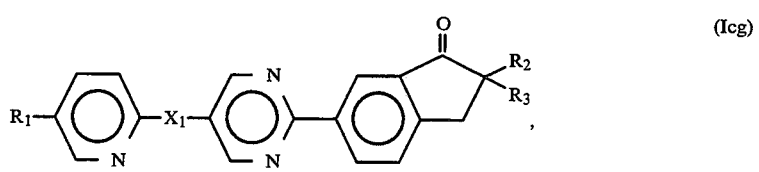
(Icg)
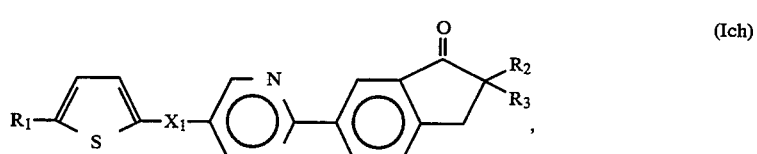
(Ich)
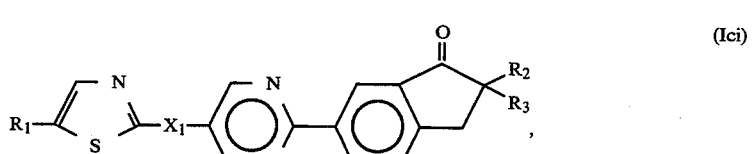
(Ici)
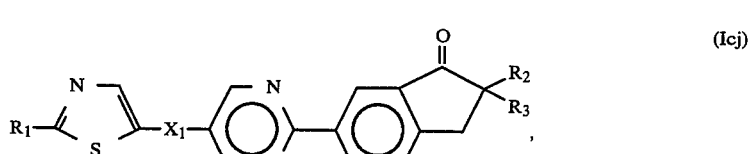
(Icj)
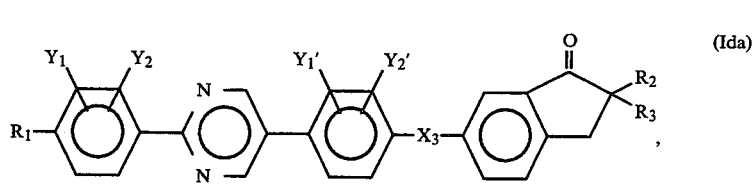
(Ida)

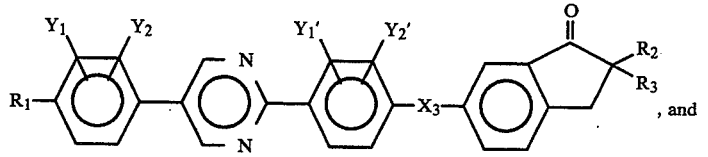
(Idb)
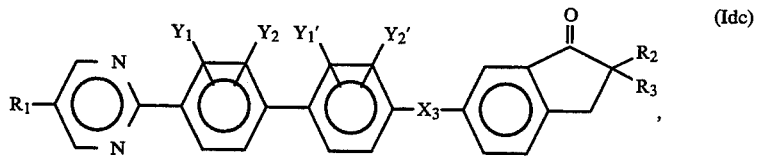
(Idc)
wherein $Y_1'$ and $Y_2'$ independently denote H, F, Cl, Br, $CH_3$, $CF_3$ or CN, and $Z_1$ denotes O or S.
6. An optically active compound according to claim 2, which is represented by any one of the following formulas (IIaa) to (IIdc):
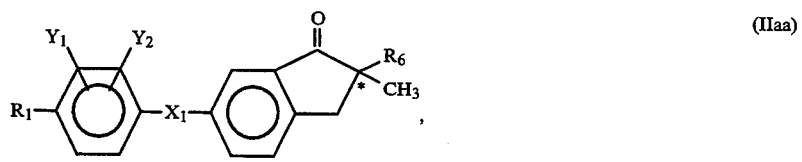
(IIaa)
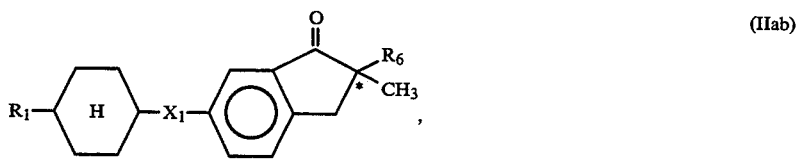
(IIab)
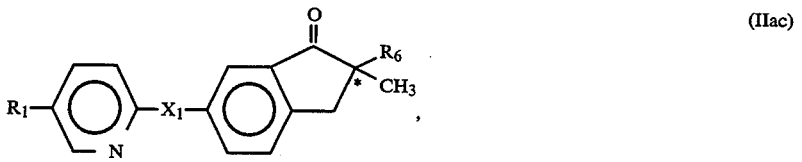
(IIac)
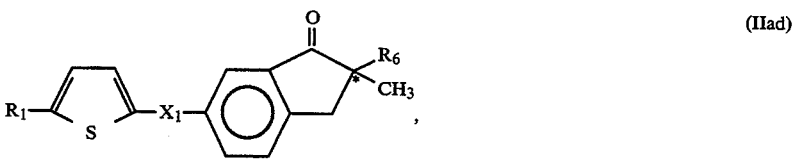
(IIad)
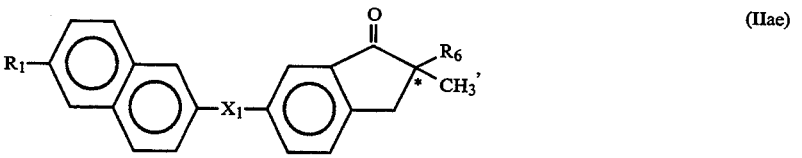
(IIae)
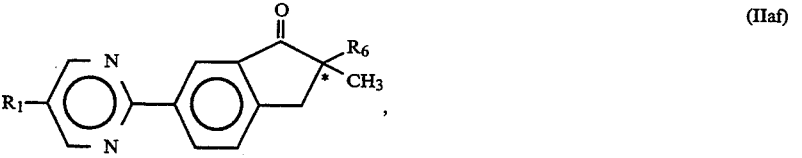
(IIaf)
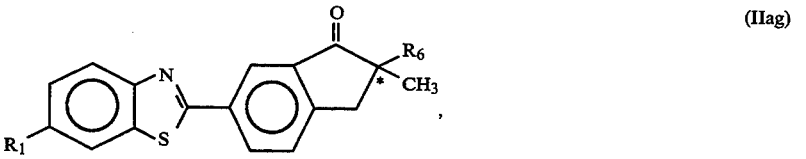
(IIag)

-continued
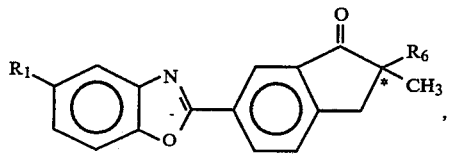 (IIah)
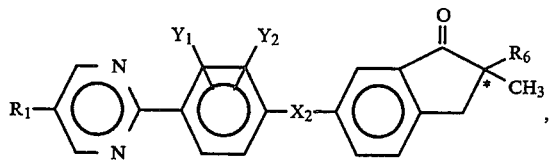 (IIba)
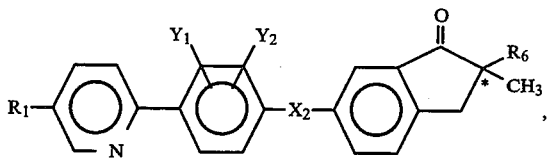 (IIbb)
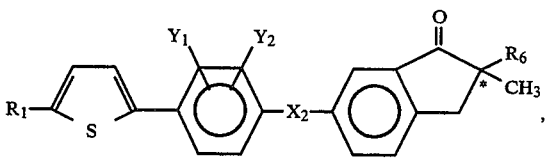 (IIbc)
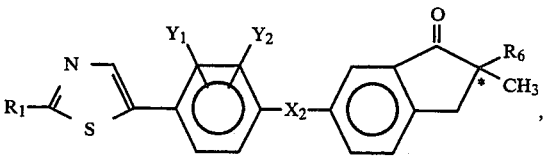 (IIbd)
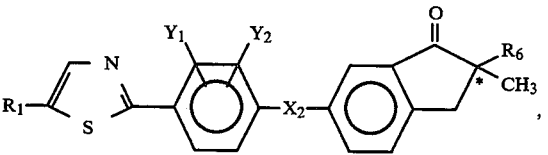 (IIbe)
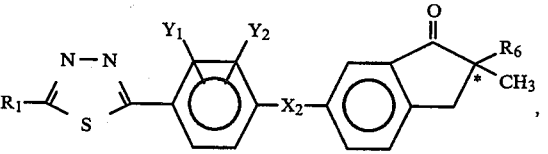 (IIbf)
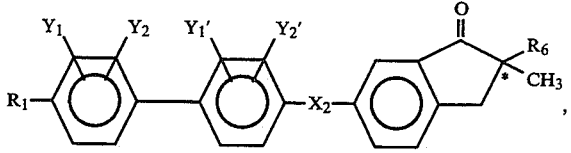 (IIbg)
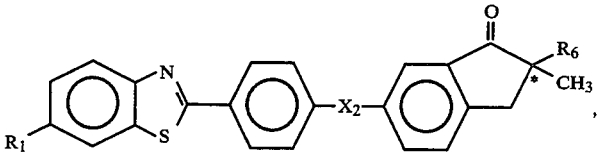 (IIbh)
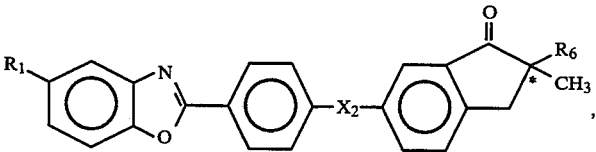 (IIbi)

-continued
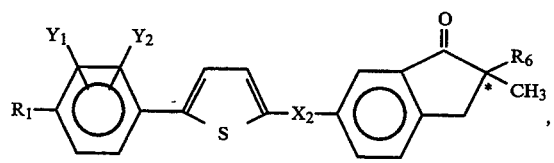
(IIbj)
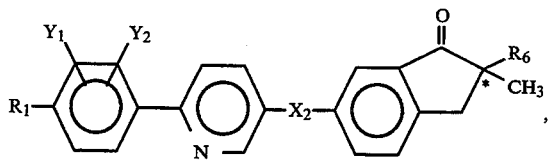
(IIbk)
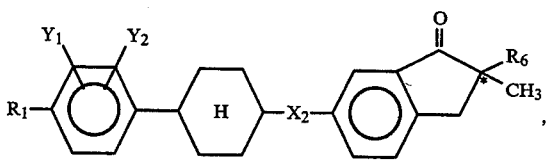
(IIbl)
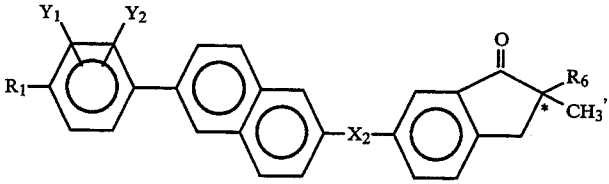
(IIbm)
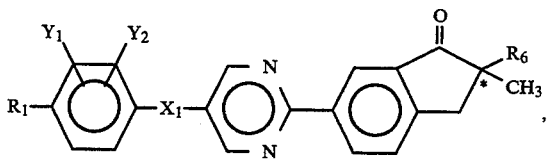
(IIca)
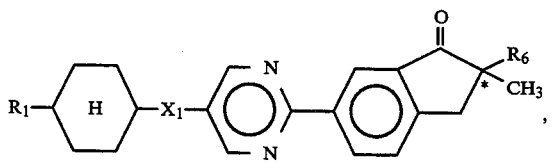
(IIcb)
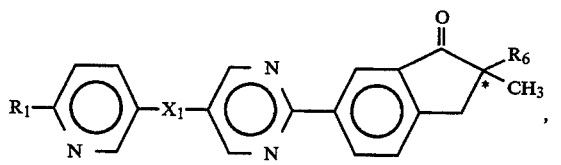
(IIcc)
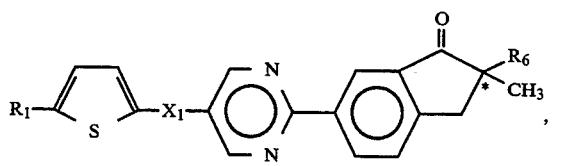
(IIcd)
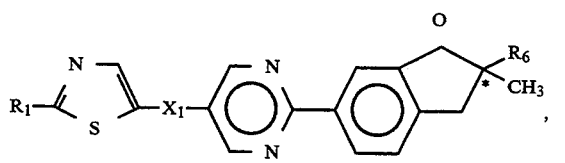
(IIce)

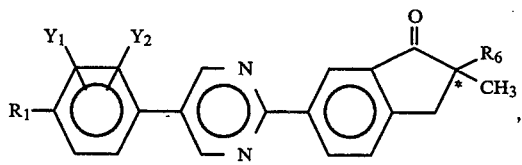
(IIcf)

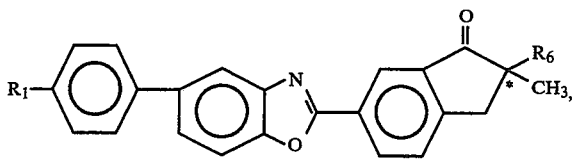
(IIcg)

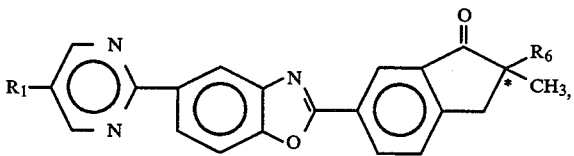
(IIch)

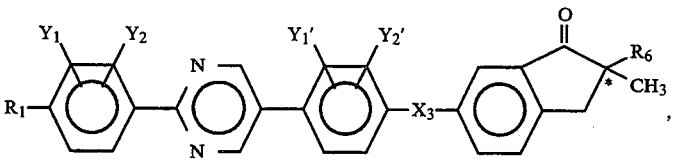
(IIda)

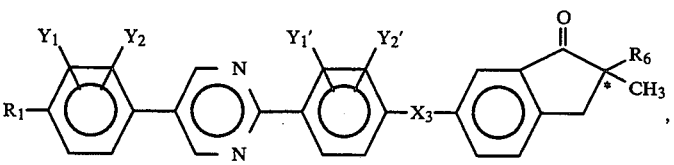
(IIdb)

and

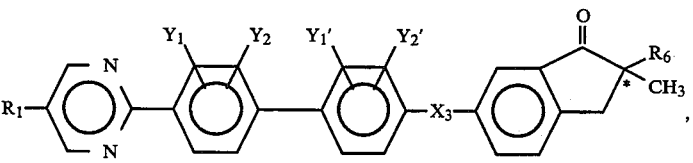
(IIdc)

wherein $Y_1'$ and $Y_2'$ independently denote H, F, Cl, Br, $CH_3$, $CF_3$ or CN, and $Z_1$ denotes O or S.

7. A mesomorphic compound according to claim 1, wherein $R_1$ and $R_3$ in the formula (I) is independently one of the following groups (i) to (vii) and $R_2$ in the formula (I) is any of the following groups (i) to (v):

(i) n—$C_aH_{2a+1}$—$X_4$—,

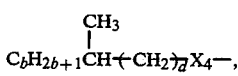 (i)

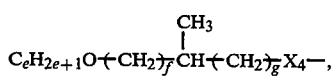 (ii)

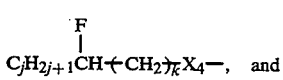 (iii)

$C_hF_{2h+1}$—$(CH_2)_i$—$X_4$—, (iv)

$C_jH_{2j+1}$CH(F)—$(CH_2)_k$—$X_4$—, and (v)

H—, and (vi)

F—, (vii)

wherein a is an integer of 1–16; d, g and i are an integer of 0–7; b, e and h are an integer of 1–8, f and k are 0 or 1, j is an integer of 1–15; and $X_4$ denotes a single bond, —O—, —OC(=O)— or —C(=O)O—.

8. A mesomorphic compound according to claim 1, wherein $R_3$ in the formula (I) is hydrogen or a linear alkyl group having 1–5 carbon atoms.

9. A mesomorphic compound according to claim 1, which is an optically active compound.

10. A mesomorphic compound according to claim 1, which is an optically inactive compound.

11. An optically active compound according to claim 2, wherein $R_1$ in the formula (II) is represented by any one of the following groups (i) to (vii):

(i) $n-C_aH_{2a+1}-X_4-$, $$n-C_bH_{2a+1}-X_4-, \quad (i)$$

$$C_bH_{2b+1}\overset{CH_3}{\underset{|}{CH}}(CH_2)_dX_4-, \quad (ii)$$

$$C_eH_{2e+1}O(CH_2)_f\overset{CH_3}{\underset{|}{CH}}(CH_2)_gX_4-, \quad (iii)$$

$$C_hF_{2h+1}(CH_2)_iX_4-, \quad (iv)$$

$$C_jH_{2j+1}\overset{F}{\underset{|}{CH}}(CH_2)_kX_4-, \text{ and} \quad (v)$$

$$H-, \text{ and} \quad (vi)$$

$$F-, \quad (vii)$$

(vi) H—, and
(vii) F—,
wherein a is an integer of 1–16; d, g and i are an integer of 0–7; b, e and h are an integer of 1–8, f and k are 0 or 1, j is an integer of 1–15; and $X_4$ denotes a single bond, —O—, $$-\underset{\underset{O}{\|}}{OC}- \text{ or } -\underset{\underset{O}{\|}}{CO}-.$$

12. A liquid crystal composition comprising at least two compounds, at least one of which is a mesomorphic compound of the formula (I) according to claim 1.

13. A liquid crystal composition according to claim 12, which comprises 1–80 wt. % of a mesomorphic compound of the formula (I).

14. A liquid crystal composition according to claim 12, which comprises 1–60 wt. % of a mesomorphic compound of the formula (I).

15. A liquid crystal composition according to claim 12, which comprises 1–40 wt. % of a mesomorphic compound of the formula (I).

16. A liquid crystal composition according to claim 12, which has a chiral smectic phase.

17. A liquid crystal composition comprising at least two compounds, at least one of which is an optically active compound of the formula (II) according to claim 2.

18. A liquid crystal composition according to claim 17, which comprises 0.1–60 wt. % of an optically active compound of the formula (II).

19. A liquid crystal composition according to claim 17, which comprises 0.1–40 wt. % of an optically active compound of the formula (II).

20. A liquid crystal composition according to claim 17, which comprises 0.1–20 wt. % of an optically active compound of the formula (II).

21. A liquid crystal composition according to claim 17, which has a chiral smectic phase.

22. A liquid crystal device, comprising a pair of electrode plates and a liquid crystal composition according to claim 12 disposed between the electrode plates.

23. A liquid crystal device according to claim 22, which further comprises an insulating alignment control layer.

24. A liquid crystal device according to claim 23, wherein the insulating alignment control layer has been subjected to rubbing.

25. A liquid crystal device according to claim 22, wherein the liquid crystal composition is disposed in a thickness suppressing formation of a helical structure of liquid crystal molecules between the electrode plates.

26. A liquid crystal device, comprising a pair of electrode plates and a liquid crystal composition according to claim 17 disposed between the electrode plates.

27. A liquid crystal device according to claim 26, which further comprises an insulating alignment control layer.

28. A liquid crystal device according to claim 27, wherein the insulating alignment control layer has been subjected to rubbing.

29. A liquid crystal device according to claim 26, wherein the liquid crystal composition is disposed in a thickness suppressing formation of a helical structure of liquid crystal molecules between the electrode plates.

30. A display apparatus comprising a liquid crystal device according to claim 22, and voltage application means for driving the liquid crystal device.

31. A display apparatus according to claim 30, which further comprises a drive circuit.

32. A display apparatus according to claim 30, which further comprises a light source.

33. A display apparatus comprising a liquid crystal device according to claim 26, and voltage application means for driving the liquid crystal device.

34. A display apparatus according to claim 33, which further comprises a drive circuit.

35. A display apparatus according to claim 33, which further comprises a light source.

36. A liquid crystal composition comprising: at least one optically active compound of the formula (II) according to claim 2, another mesomorphic compound, and an optically inactive compound.

37. A liquid crystal composition according to claim 36, which comprises 0.1–40 wt. % of an optically active compound of the formula (II).

38. A liquid crystal composition according to claim 36, which comprises 0.1–20 wt. % of an optically active compound of the formula (II).

39. A liquid crystal composition according to claim 36, which comprises 0.1–10 wt. % of an optically active compound of the formula (II).

40. A liquid crystal composition according to claim 36, which has a chiral smectic phase.

41. A liquid crystal device, comprising a pair of electrode plates and a liquid crystal composition according to claim 36 disposed between the electrode plates.

42. A liquid crystal device according to claim 41, which further comprises an insulating alignment control layer.

43. A liquid crystal device according to claim 42, wherein the insulating alignment control layer has been subjected to rubbing.

44. A liquid crystal device according to claim 41, wherein the liquid crystal composition is disposed in a thickness providing a helical structure of liquid crystal molecules between the electrode plates.

45. A display apparatus comprising a liquid crystal device according to claim 41, and voltage application means for driving the liquid crystal device.

46. A display apparatus according to claim 45, which further comprises a drive circuit.

47. A display apparatus according to claim 45, which further comprises a light source.

48. A display method, comprising:

providing a liquid crystal composition comprising at least two compounds, at least one of which is a mesomorphic compound of the formula (I) according to claim 1; and switching the alignment direction of liquid crystal molecules by applying voltages to the liquid crystal composition to effect display.

49. A display method, comprising:

providing a liquid crystal composition comprising at least two compounds, at least one of which is an optically active compound of the formula (II) according to claim 2; and switching the alignment direction of liquid crystal molecules by applying voltages to the liquid crystal composition to effect display.

50. A display method, comprising:

providing a liquid crystal composition comprising at least two compounds, at least one of which is a mesomorphic compound of the formula (I) according to claim 3; and switching the alignment direction of liquid crystal molecules by applying voltages to the liquid crystal composition to effect display.

51. A display method, comprising:

providing a liquid crystal composition comprising at least two compounds, at least one of which is an optically active compound of the formula (II) according to claim 4; and switching the alignment direction of liquid crystal molecules by applying voltages to the liquid crystal composition to effect display.

52. A display method, comprising:

providing a liquid crystal composition comprising at least two compounds, at least one of which is a mesomorphic compound of the formula (I) according to claim 5; and switching the alignment direction of liquid crystal molecules by applying voltages to the liquid crystal composition to effect display.

53. A display method, comprising:

providing a liquid crystal composition comprising at least two compounds, at least one of which is an optically active compound of the formula (II) according to claim 6; and switching the alignment direction of liquid crystal molecules by applying voltages to the liquid crystal composition to effect display.

54. A display method, comprising:

providing a liquid crystal composition comprising at least two compounds, at least one of which is a mesomorphic compound of the formula (I) according to claim 7; and switching the alignment direction of liquid crystal molecules by applying voltages to the liquid crystal composition to effect display.

55. A display method according to claim 48, wherein $R_3$ in the formula (I) is hydrogen or a linear alkyl group having 1-5 carbon atoms.

56. A display method according to claim 48, wherein the mesomorphic compound of the formula (I) is an optically active compound.

57. A display method according to claim 48, wherein the mesomorphic compound of the formula (I) is an optically inactive compound.

58. A display method according to claim 48, wherein the liquid crystal composition comprises 1-80 wt. % of a mesomorphic compound of the formula (I).

59. A display method according to claim 48, wherein the liquid crystal composition comprises 1-60 wt. % of a mesomorphic compound of the formula (I).

60. A display method according to claim 48, wherein the liquid crystal composition comprises 1-40 wt. % of a mesomorphic compound of the formula (I).

61. A display method according to claim 48, wherein the liquid crystal composition has a chiral smectic phase.

62. A display method, comprising:

providing a liquid crystal composition comprising at least two compounds, at least one of which is an optically active compound of the formula (II) according to claim 11; and switching the alignment direction of liquid crystal molecules by applying voltages to the liquid crystal composition to effect display.

63. A display method according to claim 49, wherein the liquid crystal composition comprises 0.1-60 wt. % of an optically active compound of the formula (II).

64. A display method according to claim 49, wherein the liquid crystal composition comprises 0.1-40 wt. % of an optically active compound of the formula (II).

65. A display method according to claim 49, wherein the liquid crystal composition comprises 0.1-20 wt. % of an optically active compound of the formula (II).

66. A display method according to claim 49, wherein the liquid crystal composition has a chiral smectic phase.

67. A display method, comprising:

providing a liquid crystal device comprising a pair of electrode plates and a liquid crystal composition disposed therebetween comprising at least two compounds, at least one of which is a mesomorphic compound of the formula (I) according to claim 1; and switching the alignment direction of liquid crystal molecules by applying voltages to the liquid crystal composition disposed between the electrode plates to effect display.

68. A liquid crystal device according to claim 67, which further comprises an insulating alignment control layer.

69. A liquid crystal device according to claim 68, wherein the insulating alignment control layer has been subjected to rubbing.

70. A display method, comprising:

providing a liquid crystal device comprising a pair of electrode plates and a liquid crystal composition disposed therebetween comprising at least two compounds, at least one of which is an optically active compound of the formula (II) according to claim 2; and switching the alignment direction of liquid crystal molecules by applying voltages to the liquid crystal composition disposed between the electrode plates to effect display.

71. A liquid crystal device according to claim 70, which further comprises an insulating alignment control layer.

72. A liquid crystal device according to claim 1, wherein the insulating alignment control layer has been subjected to rubbing.

* * * * *

UNITED STATES PATENT AND TRADEMARK OFFICE
CERTIFICATE OF CORRECTION

PATENT NO. : 5,354,501
DATED : October 11, 1994
INVENTOR(S) : SHINICHI NAKAMURA, ET AL.

It is certified that error appears in the above-identified patent and that said Letters Patent is hereby corrected as shown below:

ON THE TITLE PAGE

At [57] ABSTRACT, line 9 "a" (first occurrence) should be deleted.

COLUMN 2

Line 52, "abovementioned" should read --above-mentioned--.

COLUMN 4

Line 27, "premittivity" should read --permittivity--.

COLUMN 10

Line 10, "  " should read --   --.

COLUMN 19

Line 45, "(i) $n\text{-}C_aH_{2a+1}\text{-}X_f\text{-}$," should be deleted.
Line 64, "(vi) H--, and" should be deleted.
Line 65, "(vii) F--," should be deleted.

COLUMN 21

Line 22, "  " should read --   --.

UNITED STATES PATENT AND TRADEMARK OFFICE
CERTIFICATE OF CORRECTION

PATENT NO. : 5,354,501
DATED : October 11, 1994
INVENTOR(S) : SHINICHI NAKAMURA, ET AL.

Page 2 of 9

It is certified that error appears in the above-identified patent and that said Letters Patent is hereby corrected as shown below:

COLUMN 30

Line 1, "(i) n—$C_aH_{2a+1}$—$X_4$—," should be deleted.
Line 20, "(vi) H—, and" should be deleted.
Line 21, "(vii) F—," should be deleted.
Line 31, "abovementioned" should read --above-mentioned--.

COLUMN 31

Line 59, insert --<u>Scheme B</u> (case where $X_1$, $X_2$ and $X_3$ are a single bond)--.

COLUMN 33

Line 10, "$Z_1$," should read --$X_1$,--.
Line 14, "single,bond" should read --single bond--.

COLUMN 34

Line 2, "abovemen-" should read --above-men- --.

COLUMN 41

Formula (26), "CO" should read --OC--.
 ‖           ‖
 O           O
Formula (31), "$-(CH_2)_6-$" should read -- $-(CH_2)_3-$ --.

COLUMN 45

Formula (49), "$C_{14}H_{29}O$" should read --$C_{14}H_{29}$--.

UNITED STATES PATENT AND TRADEMARK OFFICE
CERTIFICATE OF CORRECTION

PATENT NO. : 5,354,501

DATED : October 11, 1994

INVENTOR(S) : SHINICHI NAKAMURA, ET AL.

It is certified that error appears in the above-identified patent and that said Letters Patent is hereby corrected as shown below:

COLUMN 65

Formula (127), "$C_6H_{11}$" should read --$C_5H_{11}$--.
Formula (131), "$C_6H_{17}$" should read --$C_8H_{17}$--.

COLUMN 99

Formula (285), "$C_6H_{13}$" should read --$C_6H_{13}O$--.

COLUMN 104

Line 49, "proviso" should read --the proviso--.

COLUMN 105

Line 47, "proviso" should read --the proviso--.
Line 48, "1:" should read --1;--.

COLUMN 107

Line 63, "proviso" should read --the proviso--.

COLUMN 109

Line 19, "proviso" should read --the proviso--.

COLUMN 110

Line 7, "114 15." should read --1-15.--.

COLUMN 115

Line 18, "follwoing" should read --following--.

UNITED STATES PATENT AND TRADEMARK OFFICE
CERTIFICATE OF CORRECTION

PATENT NO. : 5,354,501
DATED : October 11, 1994
INVENTOR(S) : SHINICHI NAKAMURA, ET AL.

It is certified that error appears in the above-identified patent and that said Letters Patent is hereby corrected as shown below:

COLUMN 116

Line 24, "$(CH_2)_r$" should read -- $(CH_2)_r$ --.

COLUMN 117

Line 1, "proviso" should read --the proviso--.

COLUMN 118

Line 59, "— —" should read -- -O- --.

COLUMN 119

Line 48, "and" should read --to--.

COLUMN 122

Line 62, "(XIIdb):" should read --(XIIfc):--.

COLUMN 124

Line 19, "$(CH_2)_p$" should read -- $(CH_2)_p$ --.
Line 26, "$(CH_2)_r$" should read -- $(CH_2)_r$ --.
Line 59, "formula" should read --formula (I).--.

COLUMN 128

Line 23, "$C_6H_{17}$" should read --$C_8H_{17}$--.

Line 28, "$C_6H_{17}$" should read --$C_8H_{17}$--.

UNITED STATES PATENT AND TRADEMARK OFFICE
CERTIFICATE OF CORRECTION

PATENT NO. : 5,354,501
DATED : October 11, 1994
INVENTOR(S) : SHINICHI NAKAMURA, ET AL.

It is certified that error appears in the above-identified patent and that said Letters Patent is hereby corrected as shown below:

COLUMN 129

Line 55, "2-noctyl" should read -- 2-n-octyl --.

COLUMN 130

Line 1, "8 hour" should read --8 hours--.
Line 12, "time" should read --times--.
Line 20, "hexane/chlor-" should read --hexane/chloro- --.
Line 30, "3 liter" should read --3 liters--.

COLUMN 135

Line 19, "6carboxylate" should read --6-carboxylate--.

COLUMN 139

Line 29, "15 second" should read --15 seconds--.

COLUMN 141

Line 23, "3.33" should read --3.3--.

COLUMN 146

Line 56, "Example 15" should read --Example 11--.

COLUMN 162

Line 58, "$C_{10}H_{21}O$" should read --$C_{10}H_{21}$--.
Line 65, "$C_{10}H_{21}O$" should read --$C_{10}H_{21}$--.

UNITED STATES PATENT AND TRADEMARK OFFICE
CERTIFICATE OF CORRECTION

PATENT NO. : 5,354,501
DATED : October 11, 1994
INVENTOR(S) : SHINICHI NAKAMURA, ET AL.

It is certified that error appears in the above-identified patent and that said Letters Patent is hereby corrected as shown below:

COLUMN 169

Line 19, "-methyl" should read --2-methyl--.
Line 63, "corresonding" should read --corresponding--.

COLUMN 170

Line 11, "pitch (m)" should read --pitch ($\mu$m)--.
Line 59, "pitch (m)" should read --pitch ($\mu$m)--.

COLUMN 171

Line 2, "<Composition $F_1$>" should read --<Composition $F_2$>--.

COLUMN 173

Line 48, "$B_1$" should read --$J_1$--.

COLUMN 174

Line 5, "pitch (m)" should read --pitch ($\mu$m)--.

COLUMN 175

Line 35, "SmC" should read --SmC*--.

COLUMN 178

Line 54, "pitch (m)" should read --pitch ($\mu$m)--.

COLUMN 179

Line 26, "$C_3H_{17}$" should read --$C_3H_7$--.

UNITED STATES PATENT AND TRADEMARK OFFICE
CERTIFICATE OF CORRECTION

PATENT NO. : 5,354,501
DATED : October 11, 1994
INVENTOR(S) : SHINICHI NAKAMURA, ET AL.

It is certified that error appears in the above-identified patent and that said Letters Patent is hereby corrected as shown below:

COLUMN 180

Line 15, "an" should be deleted.
Line 16, "ununiform" should read --nonuniform--.

COLUMN 184

Line 18, "with a" should read --was formed which was--.

COLUMN 185

Line 21, "139" should read --138--.

COLUMN 187

Line 2, "devices were" should read --device was--.

COLUMN 188

Line 16, "gen," should read --gen, -CN,--.

COLUMN 190

Line 35, "," (both occurrences) should read -- , --.

COLUMN 192

Line 3, "fluorine:" should read --fluorine;--.

UNITED STATES PATENT AND TRADEMARK OFFICE
CERTIFICATE OF CORRECTION

PATENT NO. : 5,354,501
DATED : October 11, 1994
INVENTOR(S) : SHINICHI NAKAMURA, ET AL.

It is certified that error appears in the above-identified patent and that said Letters Patent is hereby corrected as shown below:

COLUMN 193

Formula (Iak), "$X_1$" should read --$X_2$--.

COLUMN 205

Formula (IIce), "  " should read -- 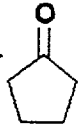 --.

COLUMN 207

Line 46, "CN, and $Z_1$ denotes O or S." should read --CN.--.
Line 51, "(1) n—$C_aH_{2a+1}$—$X_4$—," should be deleted.

COLUMN 208

Line 47, "(vi) H—, and" should be deleted.
Line 48, "(vii) F—" should be deleted.

COLUMN 209

Line 1, "(i) n—$C_aH_{2a+1}$—$X_4$—," should be deleted.
Line 20, "(vi) H—, and" should be deleted.
Line 21, "(vii) F—," should be deleted.

UNITED STATES PATENT AND TRADEMARK OFFICE
CERTIFICATE OF CORRECTION

PATENT NO. : 5,354,501

DATED : October 11, 1994

INVENTOR(S) : SHINICHI NAKAMURA, ET AL.

It is certified that error appears in the above-identified patent and that said Letters Patent is hereby corrected as shown below:

COLUMN 212

Line 64, "claim 1," should read --claim 71,--.

Signed and Sealed this

Eleventh Day of July, 1995

*Attest:*

BRUCE LEHMAN

*Attesting Officer*     *Commissioner of Patents and Trademarks*